(12) United States Patent
Strasser et al.

(10) Patent No.: US 12,186,064 B2
(45) Date of Patent: Jan. 7, 2025

(54) SYSTEMS AND METHODS FOR MULTIVARIATE STROKE DETECTION

(71) Applicant: Kandu Health, Inc., Campbell, CA (US)

(72) Inventors: Michael Strasser, Corte Madera, CA (US); Syed Hossainy, Hayward, CA (US); Sangshik Park, San Francisco, CA (US); Kirsten Carroll, San Francisco, CA (US)

(73) Assignee: Kandu Health, Inc., Campbell, CA (US)

( * ) Notice: Subject to any disclaimer, the term of this patent is extended or adjusted under 35 U.S.C. 154(b) by 0 days.

(21) Appl. No.: 17/818,281

(22) Filed: Aug. 8, 2022

(65) Prior Publication Data

US 2023/0072213 A1 Mar. 9, 2023

Related U.S. Application Data

(63) Continuation of application No. 17/407,852, filed on Aug. 20, 2021, now Pat. No. 11,504,020, which is a
(Continued)

(51) Int. Cl.
*A61B 5/00* (2006.01)
*A61B 5/024* (2006.01)
(Continued)

(52) U.S. Cl.
CPC .......... *A61B 5/0295* (2013.01); *A61B 5/0008* (2013.01); *A61B 5/0022* (2013.01);
(Continued)

(58) Field of Classification Search
None
See application file for complete search history.

(56) References Cited

U.S. PATENT DOCUMENTS

| | | | | |
|---|---|---|---|---|
| 4,926,867 A | * | 5/1990 | Kanda | A61B 5/14552 600/334 |
| 5,131,391 A | * | 7/1992 | Sakai | A61B 5/1491 600/334 |

(Continued)

FOREIGN PATENT DOCUMENTS

| | | |
|---|---|---|
| AU | 2006268156 | 4/2012 |
| CN | 101002673 | 7/2007 |

(Continued)

OTHER PUBLICATIONS

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

(Continued)

*Primary Examiner* — James M Kish
*Assistant Examiner* — James Moss
(74) *Attorney, Agent, or Firm* — Knobbe, Martens, Olson & Bear, LLP

(57) ABSTRACT

A system for detecting an anomalous event in a person includes a body in contact with a skin surface of a person; a heat source for heating the skin surface to a target temperature; a skin temperature sensor for measuring a temperature of the skin surface in contact with the heat source; a blood volume sensor for measuring a blood volume of the skin surface; and a hardware processor communicatively coupled to the heat source, the blood volume sensor, the skin temperature sensor, and an environmental temperature sensor. The hardware processor is configured to receive a baseline blood volume signal, output a heating signal to the heat source to initiate a heating cycle, receive a second blood volume signal from the blood volume sensor, compare the second blood volume signal to (Continued)

the baseline blood volume signal, and determine whether an anomalous biologic event has occurred.

17 Claims, 56 Drawing Sheets

Related U.S. Application Data continuation of application No. 17/070,832, filed on Oct. 14, 2020, now Pat. No. 11,134,859.

(60) Provisional application No. 63/053,265, filed on Jul. 17, 2020, provisional application No. 62/915,269, filed on Oct. 15, 2019.

(51) Int. Cl.
*A61B 5/0295* (2006.01)
*A61B 5/11* (2006.01)
*A61B 5/145* (2006.01)

(52) U.S. Cl.
CPC ............ *A61B 5/02405* (2013.01); *A61B 5/11* (2013.01); *A61B 5/14542* (2013.01); *A61B 5/681* (2013.01); *A61B 5/6831* (2013.01); *A61B 2562/0271* (2013.01)

(56) References Cited

U.S. PATENT DOCUMENTS

| | | | |
|---|---|---|---|
| 5,299,570 A * | 4/1994 | Hatschek | A61B 5/14552 600/323 |
| 5,638,818 A | 6/1997 | Diab et al. | |
| 6,024,575 A | 2/2000 | Ulrich | |
| 6,334,065 B1 | 12/2001 | Al Ali et al. | |
| 6,400,971 B1 | 6/2002 | Firanov et al. | |
| 6,605,038 B1 | 8/2003 | Teller et al. | |
| 6,887,199 B2 | 5/2005 | Bridger et al. | |
| 7,215,991 B2 | 5/2007 | Besson et al. | |
| 7,379,790 B2 | 5/2008 | Toth et al. | |
| 7,608,083 B2 | 10/2009 | Lee et al. | |
| 7,850,642 B2 | 12/2010 | Moll et al. | |
| 7,884,727 B2 | 2/2011 | Tran | |
| 7,955,316 B2 | 6/2011 | Weitzner et al. | |
| 7,963,288 B2 | 6/2011 | Rosenberg et al. | |
| 8,021,326 B2 | 9/2011 | Moll et al. | |
| 8,083,753 B2 | 12/2011 | Solar et al. | |
| 8,108,036 B2 | 1/2012 | Tran | |
| 8,108,069 B2 | 1/2012 | Stahler et al. | |
| 8,131,379 B2 | 3/2012 | Hauck | |
| 8,165,684 B2 | 4/2012 | Putz et al. | |
| 8,190,238 B2 | 5/2012 | Moll et al. | |
| 8,343,096 B2 | 1/2013 | Kirschenman et al. | |
| 8,377,077 B2 | 2/2013 | Reis | |
| 8,390,438 B2 | 3/2013 | Olson et al. | |
| 8,467,853 B2 | 6/2013 | Hunter et al. | |
| 8,498,691 B2 | 7/2013 | Moll et al. | |
| 8,529,582 B2 | 9/2013 | Devengenzo et al. | |
| 8,551,084 B2 | 10/2013 | Hauck et al. | |
| 8,671,817 B1 | 3/2014 | Bogusky | |
| 8,684,962 B2 | 4/2014 | Kirschenman et al. | |
| 8,694,157 B2 | 4/2014 | Wenderow et al. | |
| 8,894,610 B2 | 5/2014 | Macnamara et al. | |
| 8,840,628 B2 | 9/2014 | Green et al. | |
| 9,066,740 B2 | 6/2015 | Carlson et al. | |
| 9,168,356 B2 | 10/2015 | Wenderow et al. | |
| 9,186,046 B2 | 11/2015 | Ramamurthy et al. | |
| 9,220,568 B2 | 12/2015 | Bromander et al. | |
| 9,241,768 B2 | 1/2016 | Sandhu et al. | |
| 9,295,527 B2 | 3/2016 | Kirschenman et al. | |
| 9,314,306 B2 | 4/2016 | Yu | |
| 9,314,310 B2 | 4/2016 | Kirschenman et al. | |
| 9,314,594 B2 | 4/2016 | Kirschenman | |
| 9,320,573 B2 | 4/2016 | Sandhu et al. | |
| 9,396,642 B2 | 7/2016 | He et al. | |
| 9,408,669 B2 | 8/2016 | Kokish et al. | |
| 9,439,736 B2 | 9/2016 | Olson | |
| 9,452,276 B2 | 9/2016 | Duindam et al. | |
| 9,498,291 B2 | 11/2016 | Balaji et al. | |
| 9,545,497 B2 | 1/2017 | Wenderow et al. | |
| 9,549,783 B2 | 1/2017 | Zirps | |
| 9,572,481 B2 | 2/2017 | Duindam et al. | |
| 9,603,573 B2 | 3/2017 | Leininger et al. | |
| 9,706,269 B2 | 7/2017 | Wan et al. | |
| 9,724,042 B1 | 8/2017 | Lodato et al. | |
| 9,764,114 B2 | 9/2017 | Murphy et al. | |
| 9,782,130 B2 | 10/2017 | Hauck et al. | |
| 9,782,564 B2 | 10/2017 | Zirps et al. | |
| 9,814,425 B2 | 11/2017 | Tran | |
| 9,820,656 B2 | 11/2017 | Olivier | |
| 9,820,669 B2 | 11/2017 | Bonmassar et al. | |
| 9,825,455 B2 | 11/2017 | Sandhu et al. | |
| 9,833,293 B2 | 12/2017 | Wenderow et al. | |
| 9,839,481 B2 | 12/2017 | Blumenkranz et al. | |
| 9,855,101 B2 | 1/2018 | Wenderow et al. | |
| 9,936,916 B2 | 4/2018 | Sahin | |
| 10,070,799 B2 | 9/2018 | Ang et al. | |
| 10,080,524 B1 * | 9/2018 | Xi | A61B 5/6833 |
| 10,123,843 B2 | 11/2018 | Wong et al. | |
| 10,201,314 B2 | 2/2019 | Frederick et al. | |
| 10,231,788 B2 | 3/2019 | Olson et al. | |
| 10,258,285 B2 | 4/2019 | Hauck et al. | |
| 10,299,867 B2 | 5/2019 | Wenderow et al. | |
| 10,368,951 B2 | 8/2019 | Moll et al. | |
| 10,398,381 B1 | 9/2019 | Heneghan et al. | |
| 10,405,791 B2 | 9/2019 | Yang | |
| 10,426,557 B2 | 10/2019 | Amiri et al. | |
| 10,448,840 B2 | 10/2019 | LeBoeuf et al. | |
| 10,448,843 B1 | 10/2019 | Peeters | |
| 10,456,059 B2 | 10/2019 | Kesinger et al. | |
| 10,466,783 B2 | 11/2019 | Newberry | |
| 10,478,065 B2 | 11/2019 | Behar et al. | |
| 10,478,127 B2 | 11/2019 | Sampson | |
| 10,485,478 B1 | 11/2019 | Mirov et al. | |
| 10,534,900 B2 | 1/2020 | Cheong et al. | |
| 10,537,262 B2 | 1/2020 | Cheatham et al. | |
| 10,549,071 B2 | 2/2020 | Falb et al. | |
| 10,556,092 B2 | 2/2020 | Yu et al. | |
| 10,568,539 B2 | 2/2020 | Kowshik et al. | |
| 10,568,700 B2 | 2/2020 | Donhowe et al. | |
| 10,687,903 B2 | 6/2020 | Lewis et al. | |
| 10,695,533 B2 | 6/2020 | Deboeuf et al. | |
| 10,695,536 B2 | 6/2020 | Weitzner et al. | |
| 10,709,510 B2 | 7/2020 | Kottenstette | |
| 10,765,303 B2 | 9/2020 | Graetzel et al. | |
| 10,799,305 B2 | 10/2020 | Murphy et al. | |
| 10,814,102 B2 | 10/2020 | Laby et al. | |
| 10,835,329 B2 | 11/2020 | Wenderow et al. | |
| 10,874,468 B2 | 12/2020 | Wallace et al. | |
| 10,885,759 B1 | 1/2021 | Lee et al. | |
| 10,898,082 B2 | 1/2021 | Sandgaard | |
| 10,898,122 B2 | 1/2021 | Torres | |
| 10,900,771 B2 | 1/2021 | Kottenstette et al. | |
| 10,912,624 B2 | 2/2021 | Prentakis et al. | |
| 10,912,924 B2 | 2/2021 | Park et al. | |
| 10,918,289 B1 | 2/2021 | Wasson et al. | |
| 10,945,664 B1 * | 3/2021 | Webb | A61B 5/0059 |
| 10,973,414 B2 | 4/2021 | Moon et al. | |
| 10,987,491 B2 | 4/2021 | Wenderow et al. | |
| 10,993,657 B1 | 5/2021 | Miller et al. | |
| 11,020,014 B2 | 6/2021 | Gupta et al. | |
| 11,051,706 B1 | 7/2021 | Nadeau et al. | |
| 11,064,892 B2 | 7/2021 | Tzvieli et al. | |
| 11,116,448 B1 | 9/2021 | Trapero et al. | |
| 11,134,859 B2 * | 10/2021 | Strasser | A61B 5/681 |
| 11,141,129 B1 | 10/2021 | Trapero et al. | |
| 11,160,459 B2 | 11/2021 | Gross et al. | |
| 11,207,025 B1 | 12/2021 | Trapero et al. | |
| 11,232,866 B1 | 1/2022 | Peters | |
| 11,504,020 B2 * | 11/2022 | Strasser | A61B 5/681 |
| 2005/0165276 A1 | 7/2005 | Belson et al. | |
| 2006/0200026 A1 | 9/2006 | Wallace et al. | |
| 2007/0225614 A1 | 9/2007 | Naghavi et al. | |
| 2008/0027464 A1 | 1/2008 | Moll et al. | |

(56) References Cited

U.S. PATENT DOCUMENTS

| | | |
|---|---|---|
| 2008/0294058 A1 | 11/2008 | Shklarski |
| 2009/0171332 A1 | 7/2009 | Bonneau |
| 2009/0254083 A1 | 10/2009 | Wallace et al. |
| 2009/0264785 A1 | 10/2009 | Causevic et al. |
| 2010/0280363 A1 | 11/2010 | Skarda et al. |
| 2010/0331916 A1 | 12/2010 | Parramon et al. |
| 2011/0015484 A1 | 1/2011 | Alvarez et al. |
| 2011/0178418 A1 | 7/2011 | Avidor et al. |
| 2011/0238010 A1 | 9/2011 | Kirschenman et al. |
| 2012/0316458 A1 | 12/2012 | Rahman |
| 2013/0317388 A1* | 11/2013 | Bieberich ............... A61B 5/01 600/549 |
| 2014/0118931 A1 | 5/2014 | Hata |
| 2014/0121555 A1 | 5/2014 | Scott et al. |
| 2014/0275852 A1 | 9/2014 | Hong et al. |
| 2014/0276123 A1 | 9/2014 | Yang et al. |
| 2014/0276167 A1 | 9/2014 | Dasgupta et al. |
| 2014/0350645 A1 | 11/2014 | Diller et al. |
| 2015/0005738 A1 | 1/2015 | Blacker |
| 2015/0018723 A1 | 1/2015 | Lee et al. |
| 2015/0088002 A1 | 3/2015 | Podhajsky |
| 2015/0157220 A1 | 6/2015 | Fish et al. |
| 2015/0157252 A1 | 6/2015 | Sabesan |
| 2015/0269825 A1 | 9/2015 | Tran |
| 2015/0335288 A1 | 11/2015 | Toth et al. |
| 2015/0366518 A1 | 12/2015 | Sampson |
| 2016/0151010 A1 | 6/2016 | Erez |
| 2016/0332025 A1* | 11/2016 | Repka ............... G06F 3/014 |
| 2017/0007167 A1* | 1/2017 | Kostic ............... A61B 5/4064 |
| 2017/0021172 A1 | 1/2017 | Perez et al. |
| 2017/0027653 A1 | 2/2017 | Kirschenman |
| 2017/0095670 A1 | 4/2017 | Ghaffari et al. |
| 2017/0195637 A1 | 7/2017 | Kusens et al. |
| 2017/0224224 A1 | 8/2017 | Yu |
| 2017/0281054 A1 | 10/2017 | Stever et al. |
| 2017/0348060 A1 | 12/2017 | Blacker |
| 2018/0153477 A1 | 6/2018 | Nagale et al. |
| 2018/0168508 A1 | 6/2018 | Biel et al. |
| 2018/0169508 A1 | 6/2018 | Billardello et al. |
| 2018/0185104 A1 | 7/2018 | Olson et al. |
| 2018/0220919 A1 | 8/2018 | Wershing et al. |
| 2018/0256101 A1* | 9/2018 | Li ............... A61N 1/36031 |
| 2018/0279965 A1 | 10/2018 | Pandit et al. |
| 2018/0279995 A1 | 10/2018 | Doyle et al. |
| 2018/0289340 A1 | 10/2018 | Trindade Rodrigues et al. |
| 2018/0307362 A1 | 10/2018 | Komala et al. |
| 2019/0008360 A1 | 1/2019 | Peh et al. |
| 2019/0029606 A1* | 1/2019 | Sheth ............... A61B 5/7275 |
| 2019/0209026 A1 | 7/2019 | Han et al. |
| 2019/0240475 A1 | 8/2019 | Lawson et al. |
| 2019/0320925 A1 | 10/2019 | Juhasz et al. |
| 2019/0336227 A1 | 11/2019 | Murphy et al. |
| 2019/0365485 A1 | 12/2019 | Kottenstette et al. |
| 2019/0388016 A1* | 12/2019 | Lewis ............... A61B 5/441 |
| 2020/0000412 A1* | 1/2020 | LeBoeuf ............ A61B 5/02055 |
| 2020/0050248 A1* | 2/2020 | Smith ............... H05B 1/0227 |
| 2020/0085528 A1 | 3/2020 | Olson et al. |
| 2020/0100693 A1 | 4/2020 | Velo |
| 2020/0113452 A1 | 4/2020 | Martinez |
| 2020/0129740 A1 | 4/2020 | Kottenstette et al. |
| 2020/0143654 A1 | 5/2020 | Howard et al. |
| 2020/0170521 A1 | 6/2020 | Gupta et al. |
| 2020/0258365 A1 | 8/2020 | Ten et al. |
| 2021/0022816 A1 | 1/2021 | DeBuys et al. |
| 2021/0057112 A1 | 2/2021 | Mansi et al. |
| 2021/0093406 A1 | 4/2021 | Blacker et al. |
| 2021/0106238 A1* | 4/2021 | Strasser ............... A61B 5/0008 |
| 2021/0151179 A1 | 5/2021 | Borthakur et al. |
| 2021/0169417 A1 | 6/2021 | Burton |
| 2021/0251497 A1 | 8/2021 | Schulhauser et al. |
| 2021/0275034 A1 | 9/2021 | Frank et al. |
| 2021/0330207 A1 | 10/2021 | Richards et al. |
| 2021/0361177 A1 | 11/2021 | Shah et al. |
| 2021/0378582 A1 | 12/2021 | Day et al. |
| 2021/0391084 A1 | 12/2021 | Adams et al. |
| 2022/0015654 A1 | 1/2022 | Groppo |
| 2022/0022754 A1 | 1/2022 | Noked |
| 2022/0044539 A1 | 2/2022 | Leurs et al. |
| 2022/0096317 A1* | 3/2022 | Smith ............... A61F 7/007 |
| 2022/0386878 A1* | 12/2022 | Li ............... G01J 5/064 |
| 2023/0072403 A1 | 3/2023 | Strasser et al. |
| 2023/0122218 A1 | 4/2023 | Nielsen et al. |

FOREIGN PATENT DOCUMENTS

| | | |
|---|---|---|
| CN | 106691414 | 5/2017 |
| CN | 107233085 | 10/2017 |
| CN | 107811624 | 3/2018 |
| CN | 208404565 | 1/2019 |
| CN | 109730779 A | 5/2019 |
| CN | 109821137 A | 5/2019 |
| CN | 110151310 A | 8/2019 |
| CN | 110726907 | 1/2020 |
| EP | 1 776 057 | 11/2009 |
| EP | 2 124 705 | 5/2019 |
| IN | 201821025060 | 7/2020 |
| JP | S58-124433 | 7/1983 |
| JP | S63-130045 | 6/1988 |
| JP | H04-170934 | 6/1992 |
| JP | 2005-160984 | 6/2005 |
| JP | 2008-113876 | 5/2008 |
| RU | 2304926 C2 | 8/2007 |
| WO | WO 2000/18290 | 4/2000 |
| WO | WO 2007/102134 | 9/2007 |
| WO | WO 2009/020862 | 2/2009 |
| WO | WO 2013/103885 | 7/2013 |
| WO | WO 2016/191307 | 12/2016 |
| WO | WO 2017/165532 | 9/2017 |
| WO | WO 2017/220010 | 12/2017 |
| WO | WO 2018/015308 | 1/2018 |
| WO | WO 2019/222641 | 11/2019 |
| WO | WO 2020/061240 | 3/2020 |
| WO | WO 2020/130923 | 6/2020 |
| WO | WO 2020/130924 | 6/2020 |
| WO | WO 2021/011551 | 7/2020 |
| WO | WO 2020/167749 | 8/2020 |
| WO | WO 2020/257351 | 12/2020 |
| WO | WO 2021/011533 | 1/2021 |
| WO | WO 2021/015990 | 1/2021 |

OTHER PUBLICATIONS

Korpelainen et al., 1995, Asymmetrical skin temperature in ischemic stroke, Stroke, 26(9):1543-1547.

International Search Report and Written Opinion dated Feb. 12, 2021 in application No. PCT/US2020/055604.

Fleming et al., Jan. 2007, A Comparison of Signal Processing Techniques for the Extraction of Breathing Rate From the Photoplethysmogram, International Journal of Biological and Medical Sciences 2:4.

Iida et al., Aug. 1, 2006, Noninvasive Low-Frequency Ultrasound Energy Causes Vasodilation in Humans, Journal of the American College of Cardiology, 48(3):532-537.

Nilsson et al., 2000, Monitoring of Respiratory Rate in Postoperative Care Using a New Photoplethysmographic Technique, J Clin Monit. 16:309-315.

Pimental et al., Aug. 2017, Toward a robust estimation of respiratory rate from pulse oximeters, IEEE Transactions on Biomedical Engineering, 64(8):1914-1923.

Tarvainen et al., Feb. 2002, An advanced detrending method with application to HRV analysis, IEEE Trans Biomed Eng., 49(2):172-175.

* cited by examiner

Left and Right In Sync

Left and Right Not in Sync

Left and Right Not in Sync

Rotating Clockwise In Sync

Rotating Clockwise Not In Sync

Rotating Anti-Clockwise In Sync

Rotating Anti-Clockwise Not Sync

Rotating Clockwise In Sync

Rotating Clockwise Not In Sync

Rotating Anti-Clockwise In Sync

Rotating Anti-Clockwise Not Sync

SYSTEMS AND METHODS FOR MULTIVARIATE STROKE DETECTION

INCORPORATION BY REFERENCE

This application is a continuation of U.S. patent application Ser. No. 17/407,852, filed Aug. 20, 2021, which is a continuation of U.S. patent application Ser. No. 17/070,832, filed on Oct. 14, 2020, now U.S. Pat. No. 11,134,859, which claims priority to U.S. Provisional Patent Application No. 62/915,269, filed on Oct. 15, 2019, and to U.S. Provisional Patent Application No. 63/053,265, filed on Jul. 17, 2020. Each of the patent applications are hereby incorporated by reference herein in their entireties, forming part of the present disclosure. Any feature, structure, material, method, or step that is described and/or illustrated in any embodiment in the foregoing patent applications can be used with or instead of any feature, structure, material, method, or step that is described in the following paragraphs of this specification and/or illustrated in the accompanying drawings.

TECHNICAL FIELD

This disclosure relates generally to the field of disease detection and, more specifically, to stroke detection.

BACKGROUND

A stroke results from the death of brain tissue due to disruptions of blood flow to the brain. An ischemic stroke happens when there is a blockage of blood flow to the brain, usually as the result of a blood clot. Hemorrhagic stroke happens when there is a rupture of a blood vessel in the brain, resulting in bleeding into the brain tissue and surrounding space.

There are many physiologic symptoms of stroke onset that vary depending on the location of the affected tissue. Early symptoms of an evolving stroke may be able to reduce or even resolve if the interruption of blood flow is resolved quickly, before the tissue has died. One category of symptoms is disrupted vision, including blurred, dimming often likened to a curtain falling) or even complete loss of vision. Stroke patients often also experience eye deviation or difficult with eye tracking.

Just as a stroke can affect the part of the brain that is associated with sight, it can also affect the parts of the brain that have to do with speech, comprehension and communication. Patients suffering from a stroke may exhibit slurred speech or garbled speech that renders them incomprehensible.

Another common symptom of stroke is weakness on one side of the body. This can manifest or partial or total paralysis of the side of the face, one arm, one leg, or the entire side of one's body.

Ischemic stroke is the most common type of stroke and is often painless when experienced, but hemorrhagic strokes are very painful, often being described as sudden onset of "the worst headache of one's life". Often, many people's headaches are accompanied with a feeling of dizziness, nausea, and vomiting. Smell and taste can also be impacted during the onset of a stroke.

Anything that affects the brain, from trauma to stroke, has the potential for cognitive disablement. A feeling of confusion, or a constant second-guessing of ones' actions, can sometimes appear days before a stroke occurs.

Another common symptom of a stroke is the sudden onset of fatigue.

Stroke symptoms can vary in duration and occur with or without pain, which can make stroke detection difficult. Further, strokes can occur during sleep, making detection even more difficult. If a stroke does occur while the person is sleeping, it may not wake a person up right away. As a result, when patients wake up symptomatic, it is unclear whether the stroke just started or whether it has already been occurring during sleep.

If a stroke is detected and patients seek care quickly, there are many evidence-based interventions that can dramatically reduce the death and disability resultant from the disease. In severe ischemic strokes, every minute of delay to flow restoration is equated to the loss of a week of Disability Adjusted Life Years (DALYs). Despite these treatments being available, fewer than 20% of patients receive them. Even among patients that do receive intervention, outcomes are often suboptimal because of the delays to intervention. Stroke detection is difficult because stroke frequently doesn't hurt, mimics other health events, and is heterogeneous in its presentation. Improvements in detection of and care-seeking for stroke onset could dramatically reduce the death and disability associated with the disease.

Like stroke, COVID-19 is proving to have heterogeneous symptoms, many of which resemble those of neurologic disorders. Recent publications have shown early evidence of encephalopathies, inflammatory CNS syndromes, ischemic strokes, and peripheral neurological disorders in patients being treated for COVID-19. (Zubair, JAMA Neurology, 2020) With most COVID-19 patients being managed remotely, and a significant percentage of inpatients requiring invasive ventilation, monitoring for the obvious symptoms of neurological disruption may be difficult. As such, improvements in remote monitoring and care for COVID-19 patients could dramatically reduce the death and disability associated with the disease.

SUMMARY

One aspect of the present disclosure is directed to a wearable system for detecting an anomalous biologic event in a person. The system includes a body having a first surface opposite a second surface in contact with a skin surface of a person; a thermal stimulus source such as a heat source or a Peltier cooler in communication with the skin surface, such that the heat source is configured to heat the skin surface to a target temperature; a skin temperature sensor positioned on the second surface and configured to measure a temperature of the skin surface in contact with the heat source; a blood volume sensor positioned on the second surface and configured to measure a blood volume of the skin surface; and a hardware processor communicatively coupled to the heat source, the blood volume sensor, the skin temperature sensor, and an environmental temperature sensor configured to measure a temperature of the environment around the wearable system. The hardware processor is configured to: receive a baseline blood volume signal from the blood volume sensor, output a heating signal to the heat source to initiate a heating cycle, such that the heating cycle comprises heating the skin surface to the target temperature, receive a second blood volume signal from the blood volume sensor in response to the skin surface reaching the target temperature, compare the second blood volume signal to the baseline blood volume signal, and determine whether an anomalous biologic event has occurred based on the comparison.

In some embodiments, the second blood volume signal includes a set of blood volume signals, such that the blood volume of the skin surface is measured repeatedly before, during, and after a heating cycle of the heat source. In some embodiments, the second blood volume signal includes a plurality of blood volume signals, such that the blood volume of the skin surface is measured continuously before, during, and after a heating cycle of the heat source.

In some embodiments, hardware processor is further configured to receive the second blood volume signal after the target temperature is reached, after a predetermined length of time has expired, or after one or more heating cycles have concluded.

In some embodiments, comparing the second blood volume signal to the baseline blood volume signal includes calculating a baseline ratio of alternating current (AC) to direct current (DC) for the baseline blood volume signal and a second ratio of AC to DC for the second blood volume signal and comparing the baseline ratio to the second ratio.

In some embodiments, the environmental temperature sensor is positioned on the first side of the body of the wearable system.

In some embodiments, the system further includes a remote computing device communicative coupled to the wearable system and comprising the environmental temperature sensor. In some embodiments, the remote computing device includes one of: a laptop, cellular device, a workstation, a server, a desktop computer, a personal digital assistant, a second wearable system or device, or a netbook.

In some embodiments, the heat source is positioned on the second surface of the body.

In some embodiments, the hardware processor is further configured to receive baseline temperature signals from the skin temperature sensor and the environmental temperature sensor, determine the target temperature based on the baseline temperature signals, and determine whether the target temperature is below a maximum temperature value.

In some embodiments, the hardware processor is further configured to cycle the heat source to maintain the target temperature.

In some embodiments, the system further includes one or more electrodermal activity sensors positioned on the second surface.

In some embodiments, the one or more electrodermal activity sensors are spaced apart from the heating element by about 0.25 inches to about 4 inches.

In some embodiments, the system further includes one or more motion sensors configured to measure a motion of a body portion to which the wearable system is coupled.

In some embodiments, the first and second surfaces define a cavity therebetween to provide airflow between the first and second surfaces.

In some embodiments, the hardware processor resides on or within the first surface.

In some embodiments, the cavity defined by the first and second surfaces physically separates the heat source from the hardware processor on or within the first surface.

In some embodiments, the cavity defined by the first and second surfaces has sufficient volume to facilitate cooling of the heat source in between heating cycles.

In some embodiments, the anomalous biologic event comprises a stroke event.

In some embodiments, the wearable system is positioned on a left limb of a user and a second wearable system is positioned on a right limb of the user, wherein the second wearable system comprises a second heating element, a second skin temperature sensor, and a second blood volume sensor, wherein the hardware processor is further configured to compare right side blood volume signals to left side blood volume signals to determine whether the anomalous biologic event has occurred.

In some embodiments, the hardware processor is further configured to synchronize the signals received from the left limb and the right limb in time; and compare the synchronized signals from the left limb and the right limb to determine whether the anomalous biologic event occurred. In some embodiments, the comparison takes into account a baseline difference between the left limb and the right limb.

In some embodiments, the system further includes a tensionable band coupled to the body. In some embodiments, the tensionable band further includes a visual indicator to indicate when one or more of: the heating element, the skin temperature sensor, the blood volume sensor, or a combination thereof is sufficiently coupled to the skin surface to enable accurate sensor readings. In some embodiments, one or more ends of the tensionable band are coupled to the body at a position that is centered with respect to one or more sensors positioned on the second surface.

In some embodiments, the heat source is positioned concentrically about one or both of the blood volume sensor and the skin temperature sensor.

In some embodiments, the blood volume sensor comprises a photoplethysmography sensor or an impedance plethysmographic sensor.

In some embodiments, the skin temperature sensor comprises a thermocouple, a resistance temperature detector, a thermistor, or an infrared temperature sensor.

In some embodiments, the system further includes a support structure coupled to the heat source and configured to couple the heat source to the second surface and at least partially expose the heat source to the cavity.

In some embodiments, the blood volume sensor is further configured to measure one or more of: heart rate, heart rate variability, or oxygen saturation.

In some embodiments, the target temperature is individualized to the user. In some embodiments, individualization of the target temperature includes receiving a user input related to perceived temperature of the skin surface. In some embodiments, individualization of the target temperature is based on signals received from the blood volume sensor.

In some embodiments, the heat source comprises one of: a heating element or an environmental temperature.

Another aspect of the present invention is directed to a wearable system for detecting an anomalous biologic event in a person. The system includes a body having a first surface opposite a second surface in contact with a skin surface of a person, the first and second surfaces defining a cavity therebetween to provide airflow between the first and second surfaces; a heating element positioned on the second surface and configured to heat the skin surface for a predetermined length of time; a skin temperature sensor positioned on the second surface and configured to measure a temperature of the skin surface in contact with the heating element; a blood volume sensor positioned on the second surface and configured to measure a blood volume of the skin surface; and a hardware processor communicatively coupled to the heating element, the blood volume sensor, the skin temperature sensor, and an environmental temperature sensor configured to measure a temperature of the environment around the wearable system.

The hardware processor is configured to receive a baseline blood volume signal from the blood volume sensor, output a heating signal to the heating element to initiate a heating cycle, such that the heating cycle comprises heating the skin surface to a target temperature, receive a second blood volume signal from the blood volume sensor in response to the skin surface reaching the target temperature, compare the second blood volume signal to the baseline blood volume signal, and determine whether an anomalous biologic event has occurred based on the comparison.

Another aspect of the present invention is directed to a wearable system for detecting an anomalous biologic event in a person. The system includes a body having a first surface opposite a second surface in contact with a skin surface of a person; a heat source in communication with the skin surface, such that the heat source is configured to heat the skin surface to a target temperature; a skin temperature sensor positioned on the second surface and configured to measure a temperature of the skin surface in contact with the heat source; a sensor positioned on the second surface and configured to measure a parameter of interest of the person; and a hardware processor communicatively coupled to the heat source, the sensor, the skin temperature sensor, and an environmental temperature sensor configured to measure a temperature of the environment around the wearable system.

The hardware processor is configured to receive a baseline sensor signal from the sensor, output a heating signal to the heat source to initiate a heating cycle, wherein the heating cycle comprises heating the skin surface to the target temperature, receive a second sensor signal from the sensor in response to the skin surface reaching the target temperature, compare the second sensor signal to the baseline sensor signal, and determine whether an anomalous biologic event has occurred based on the comparison.

In some embodiments, the sensor is selected from the group consisting of: a stretch sensor, an electrodermal activity sensor, an electrocardiogram sensor, a camera, or a blood volume sensor.

In some embodiments, the parameter of interest includes one or more of a blood pressure, a heart rate, a heart rate variability, a gaze, a facial expression, a skin conductance response, a vasodilation response, or a dilation response.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1A:
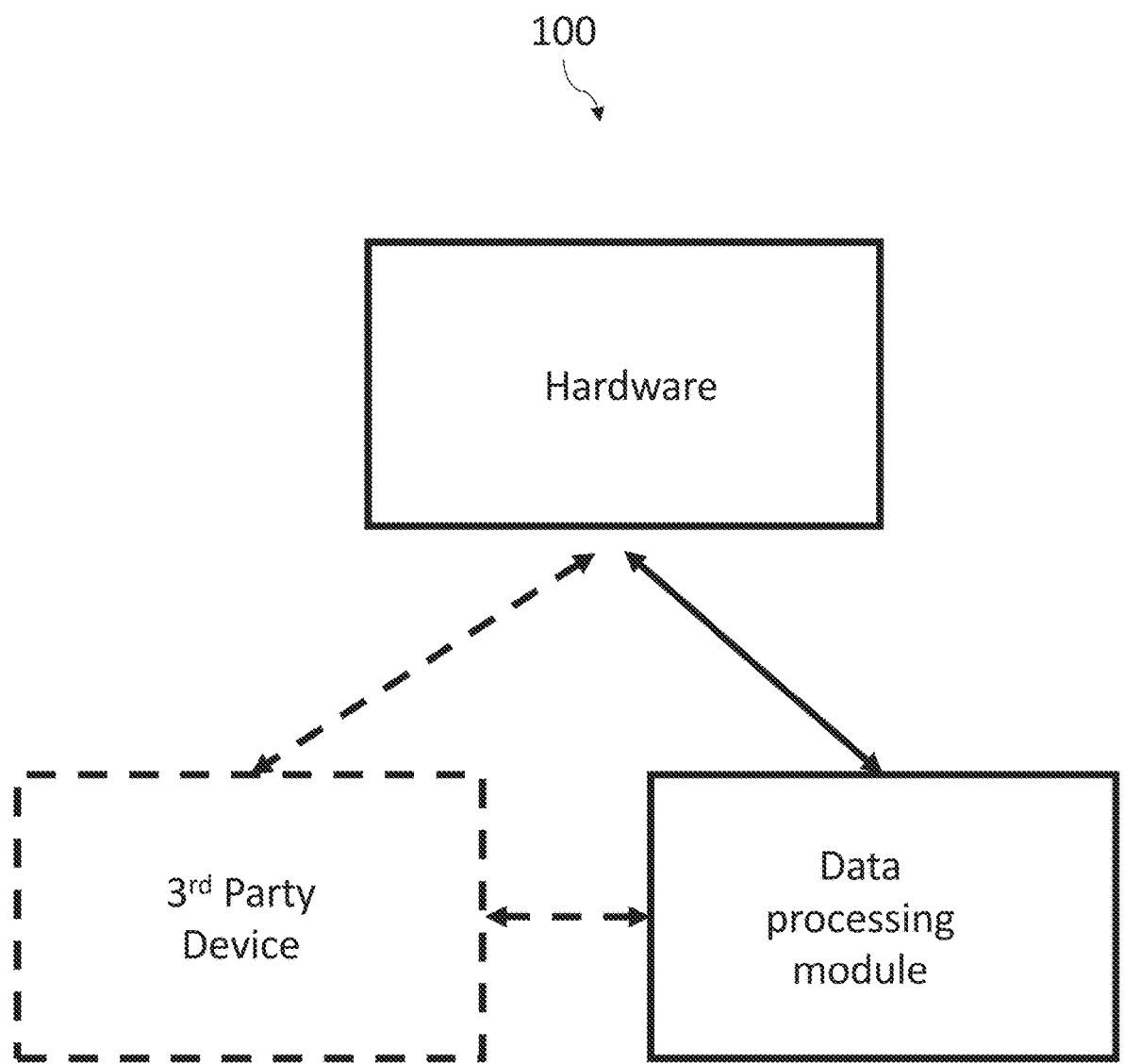
FIG. 1A illustrates one embodiment of a multivariate system for stroke detection.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Described herein are systems, devices, and methods for multivariate detection of stroke. Multivariate may include using more than one, at least two, or a plurality of factors, markers, or other parameters to detect stroke. In some embodiments, multivariate may include using one parameter measured at multiple locations or positions or at multiple times (e.g., random or fixed intervals, on demand, automatically, etc.). In various embodiments, multivariate may include detecting a measured parameter symmetrically or asymmetrically. The measured parameter may include a functional parameter (e.g., gait, speech, facial changes, etc.); a biological parameter or marker (e.g., blood proteins, metabolites, etc.); a quantitative parameter (e.g., limb asymmetry, heart rate variability, etc.); a spatial (e.g., neck vs. chest; arm vs. leg; etc.) difference in one or multiple (e.g., 2, 3, 4, 5, 10, 15, 20, etc.) measured parameters; and/or a temporal difference in one or multiple measured parameters.

In some embodiments, there may be an overlay of multivariate signals including two measurement data types, physiological or quantitative signals (e.g., skin electromagnetic potential, Doppler flow signal anomaly, hyperhydrosis, cutaneous blood flow, brain perfusion, heartrate variability, etc.), and/or clinical manifestations or functional parameters (e.g., limb asymmetry, speech slur, facial droop, retinal abnormality, etc.). Clinical manifestations occur following stroke onset, but a faint signal from a clinical manifestation measurement combined with a physiological signal measurement may detect or predict stroke likelihood prior to stroke onset. Parameters that may be measured before, during, or after a stroke include quantitative parameters, functional parameters, and/or blood/fluid parameters. Any of the parameters shown/described herein may be measured asymmetrically, as described elsewhere herein. Exemplary, non-limiting examples of quantitative parameters include: volumetric impedance spectroscopy, EEG asymmetry, brain perfusion, skin/body temperature (e.g., cold paretic limb, up to 6° C. colder or 16% colder than non-paretic limb), hyperhidrosis (e.g., greater than 40-60% increase on paretic limb), limb asymmetry, drift and pronation test, cutaneous blood flow, muscle tone, heartrate variability (e.g., decrease in spectral components by greater than 10×, lasting 3-7 days after stroke onset), facial surface EMG, cerebral blood flow (CBF), carotid artery stenosis, salivary cortisol, neuron specific enolase (NSE), salivary (NSE), etc. Exemplary, non-limiting examples of functional parameters include: speech changes, speech comprehension, text comprehension, consciousness, coordination/directions, facial muscle weakness, arm weakness, body weakness (e.g., grip), leg weakness, foot weakness, unilateral weakness, difficulty walking, vertigo, sudden vision problems, limited visual field, altered gaze, thunderclap headache, nuchal rigidity (nape of neck), respiration, blood pressure (e.g., increase up to 60% in both systole (200 mHg) and diastole (140 mmHg)), etc. Exemplary, non-limiting examples of blood/fluid parameters include: CoaguCheck (Roche), HemoChron (ITC), iSTAT (Abbott), Cornell University, ReST (Valtari Bio Inc.), SMARTChip (sarissa Biomedical), etc.

Figure 2:
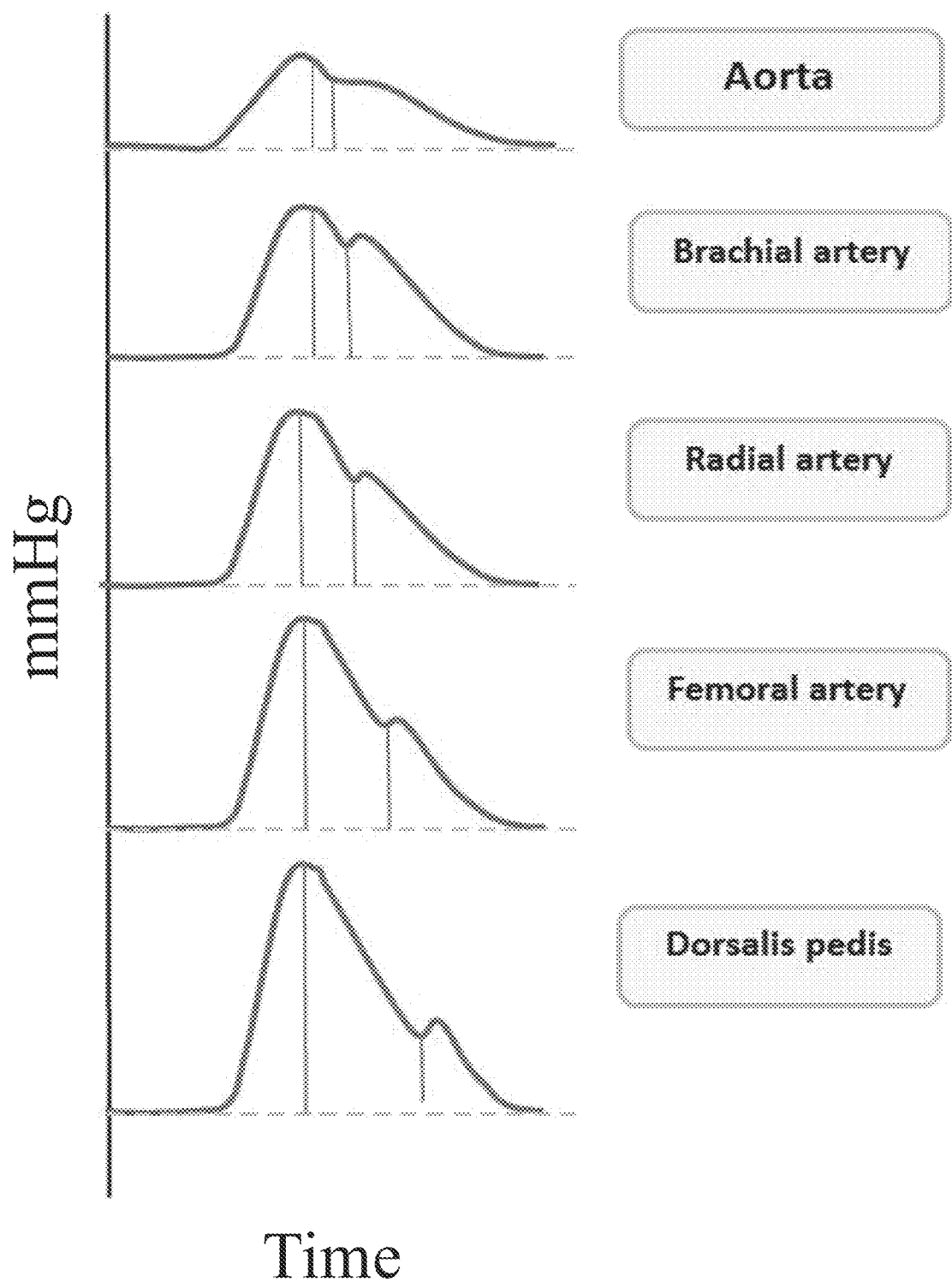
FIG. 2 shows blood pressure pulse in various parts of the body.

In some embodiments, multiple measurement locations (e.g., radial, brachial, etc. vessels) may be used to measure a difference in signal or data pattern among those locations compared to nominal, healthy location measurements or compared to an individual baseline as an input into a data processing module. For example, an individual baseline may be recorded over time and, when an adverse event occurs, a change (e.g., absolute or relative value) from baseline is determined unilaterally or bilaterally. In some embodiments, after the adverse event occurs, a new baseline may be established. Further for example, as shown in FIG. 2, blood pressure pulse varies depending on the location in the body, demonstrating that a slightly different signal is measured depending on location. For example, if only one location is measured, then changes over time are observed. If multiple locations are monitored and/or measured, then changes over time and changes relative to one another and/or a baseline can be used to identify a pattern or an asymmetric signal occurrence. In some embodiments, an individualized baseline is further calculated based on a patient's health history (e.g., diabetes, heart-pacing, pre-existing stroke, menopause etc.), demographics, lifestyle (e.g., smoker, active exerciser, drinks alcohol, etc.), etc.

Figure 1B:
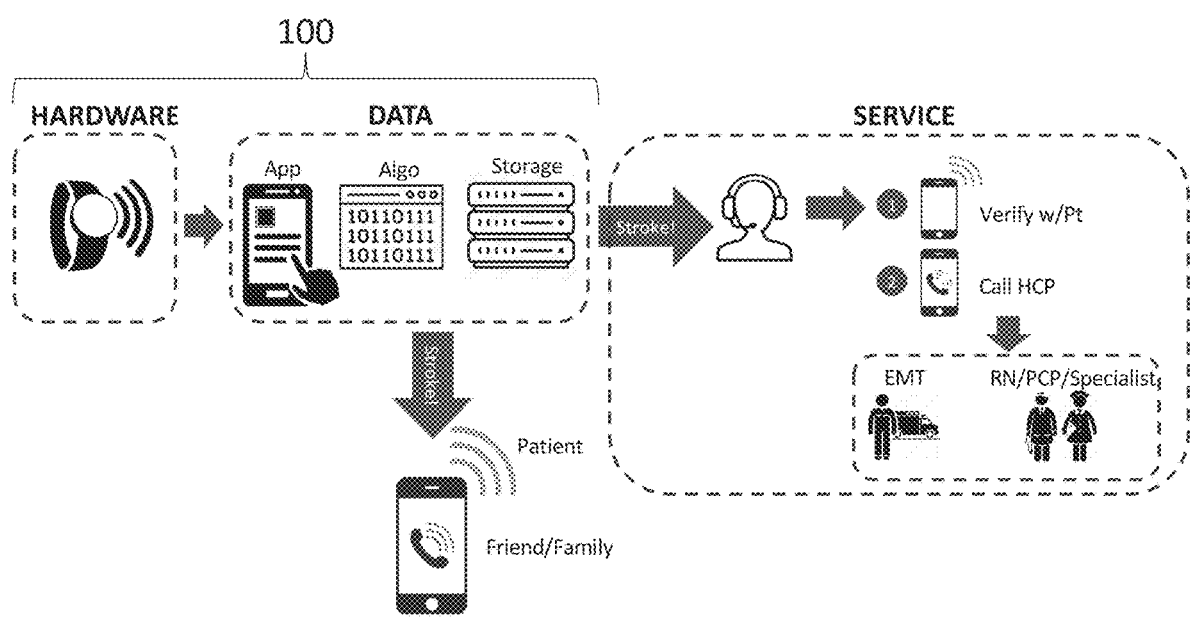
FIG. 1B illustrates another embodiment of a multivariate system for stroke detection.

In some embodiments, as shown in FIGS. 1A-1B, a system 100 for multivariate detection of stroke includes a hardware component (e.g., wearable device, sensor, computing device, remote sensing device, etc.) and a data processing module stored in the hardware or in communication with the hardware. The hardware component, for example one or more sensors, may be positioned on a user of the system, bilaterally on a user of the system, or throughout a location occupied by a user. Optionally (shown by dashed lines), a system for multivariate stroke detection may further include a third party device, for example a device including Amazon® Alexa® or an Amazon® Echo® device, as described in further detail elsewhere herein. For example, there may be bidirectional communication (e.g., via a wired connection or wireless communication) between the hardware component and the data processing module, the data processing module and the third party device, and/or the third party device and the hardware component.

In one exemplary, non-limiting embodiment of the system of FIG. 1, a digital FAST (i.e., facial drooping, arm weakness, speech difficulties, time for help) test may be performed by the system of FIG. 1. For example, the hardware component may include one or more cameras positioned throughout a location occupied by a user and configured to detect changes (e.g., using computer vision techniques) in facial expressions (e.g., drooping) as a result of stroke, as shown in FIG. 3B (i.e., the "F" part of a FAST test). Further, one or more sensors or other hardware component (e.g., camera, microphone, etc.) may be positioned throughout the location occupied by user. The one or more sensors are communicatively coupled to the data processing module such that parameters sensed by the sensors may be transmitted to the data processing module for digitization, filtering, process, and/or analysis. In the case of a digital FAST test, asymmetrical arm weakness may be sensed by the one or more sensors. To discern speech difficulties, a third party device configured to receive and assess speech quality may be communicatively coupled to the data processing module and/or hardware component. As such, a user may be prompted to speak by the third party device and the user's response may be sensed by the hardware component (e.g., one or more microphones) so that a quality of speech of the user may be determined. One or more of these detected parameters may be analyzed and optionally sent to a caregiver, approved family and/or friends, healthcare provider, physician, and/or emergency services.

In some embodiments, a system for multivariate stroke detection may further include an application downloaded and/or stored on a hardware component or downloaded and/or stored on a computing device (e.g., mobile computing device) communicatively coupled to the hardware component. The application may be configured to process sensor data, camera data, speech data, etc. and/or display data sensed or captured in real time, for example in a graphical representation, and/or allow zooming to view various features of the data.

In some embodiments, data may be transmitted to and/or from the device for detecting stroke to a central hub, mobile computing device, server, or other storage and/or computing device. Data transmission may include wireless communication (e.g., a nearfield communications (NFC) protocol, a low energy Bluetooth® protocol, other radiofrequency (RF) communication protocol, etc.) between sensor locations on the body and/or a central hub. In other embodiments, data transmission may include wire communication between sensor locations on the body and/or a central hub. In some embodiments, the central hub may be a monitor in a medical facility, home monitor, patients' mobile computing device, or other wireless device. Alternatively, one or more of the sensors on the body may act as the central hub. The hub device may wirelessly send signals to activate a medical care pathway and/or notify one or more individuals (e.g., family, friends, physician, EMS, etc.).

In some embodiments, data transmission, following multivariate analysis, to the central hub may alert the patient, the next of kin, and/or a third party to identify possible false positives or negatives.

In some embodiments, a device for stroke detection may be worn on an exterior or skin surface of the patient or implanted as hardware prior to and/or during stroke, including up to days before the event and during the event to provide continuous variable monitoring of various physiological parameters. The various embodiments described herein may either be a wearable device or an implantable device.

Figure 7:
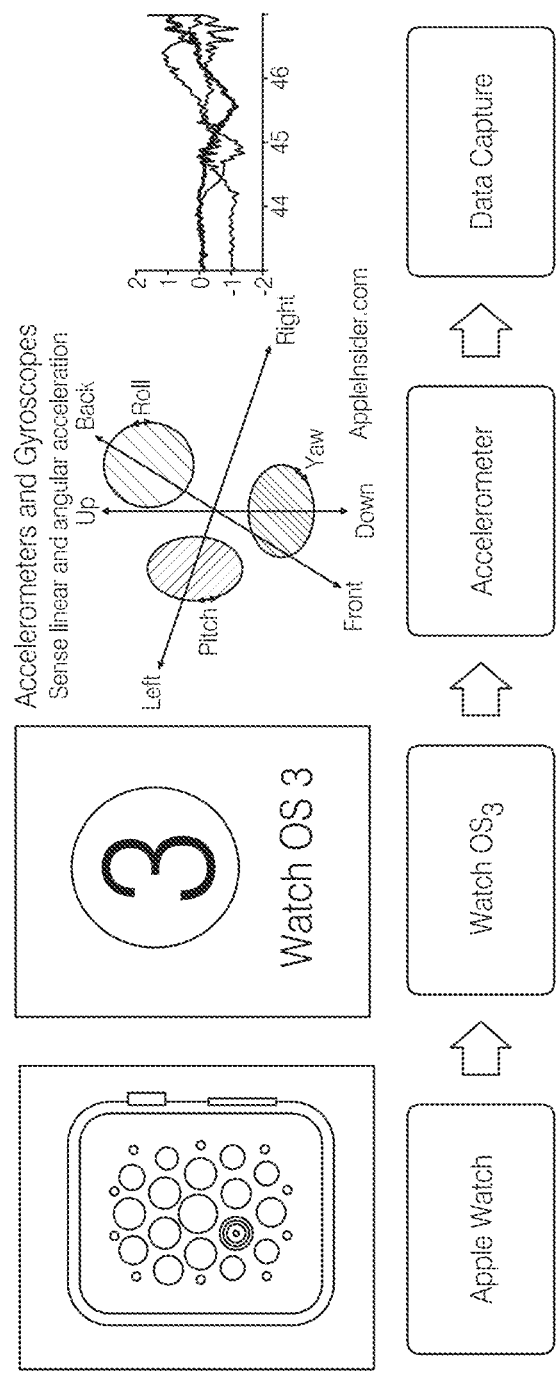
FIG. 7 shows one embodiment of a data capture workflow involving movement data measurements (e.g., acceleration).

In some embodiments, a device for detecting stroke may include a wearable device, for example a patch, headband or sweatband, ring, watch (e.g., to measure movement as shown in FIG. 7), adhesive strip, helmet, bracelet, anklet, sock (e.g., to measure heart rate, heart rate variability, temperature, gait, etc.), shoe insoles (e.g., to measure heart rate, heart rate variability, temperature, gait, etc.), clothing, belt, necklace, earring (e.g., over or in the ear to measure heart rate, heart rate variability, EEG asymmetry, etc.), hearing aid, earbuds, glasses or sunglasses or smart glasses (e.g., to measure EOG, EMG, EEG, gaze, facial muscle movement or drooping, etc.), smart tattoo (e.g., to measure EEG, ECG, etc.), bra, bra clip, chest strap, contacts (e.g., to measure tear composition, etc.), mouthguard or bite splint (e.g., to measure saliva neuron specific enolase, cortisol, temperature, motion, etc.), hat or cap (e.g., to measure various signals using ultrasound), wearable speaker (e.g., to measure heart rate, heart rate variability, motion, etc.), or otherwise a sensor integrated into any wearable clothing, accessory, or device. For example, a patch (e.g., wearable on the neck) may be used to estimate cerebral blood flow using doppler ultrasound, blood oxygen content, or other blood feature as an indicator of blood going into the brain (Carotid Artery) or leaving the brain (Jugular Vein); a patch or strip (e.g., wearable on the head) may be used to detect EEG or sEMG. Further for example, a wearable device for detecting stroke may include one or more transdermal sensors that are configured to measure changes in one or more gasses transfused through the skin (e.g., Nitric Oxide (NO) could either be measured directly, or through measurement of particular bi-products); one or more biomarkers that are in the blood that are diffused into the subcutaneous region or into the epidermis and can be measured externally. In some embodiments, a wearable device for detecting stroke may comprise a wristband or patch with a combination of microneedles that are configured to measure the fluid sub-dermally or interstitial fluid (e.g., similar to continuous glucose monitors).

In some embodiments, a wearable device for detecting stroke may comprise a wearable array of indicators (e.g., chromogenic indicators) configured to measure a chemical, analyte, protein, etc. in a bodily fluid of an individual (e.g., blood, interstitial fluid, etc.). For example, the array may comprise a membrane with a printed array thereon that when exposed to one or more analytes, a subset of the indicator spots responds by changing color or properties. The color response of the indicators may be optically read, for example using a camera on a computing device or other image sensor and compared to a baseline reading or a reference or standard. A color difference map may be generated by superimposing and/or subtracting the two images (baseline and experimental or experimental and reference/standard). As an exemplary, non-limiting analyte, an increase in nitric oxide may be detected in blood or interstitial fluid of an individual after a stroke event and/or modification of one or more proteins by nitric oxide may be detected in blood or interstitial fluid of an individual after a stroke event and/or one or more intermediates or byproducts of nitric oxide may be detected in blood or interstitial fluid of an individual after a stroke event. For example, nitric oxide has been shown to modify proteins via: 1) binding to metal centers; 2) nitrosylation of thiol and amine groups; 3) nitration of tyrosine, tryptophan, amine, carboxylic acid, and phenylalanine groups; and 4) oxidation of thiols (both cysteine and methionine residues) and tyrosine. Such methods may bypass the need to measure an asymmetrical change in one or more parameters, as described elsewhere herein.

Figure 38:
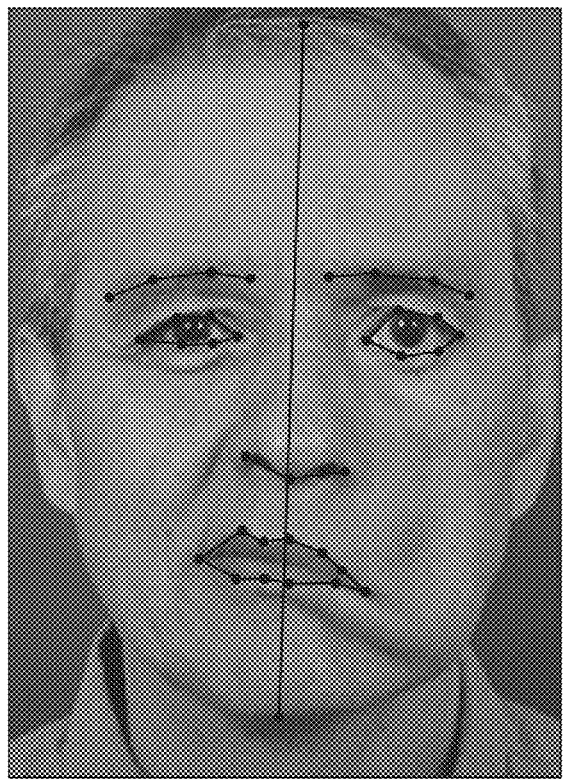
FIG. 38 illustrates an embodiment of a digital "FAST" test.
Figure 38:
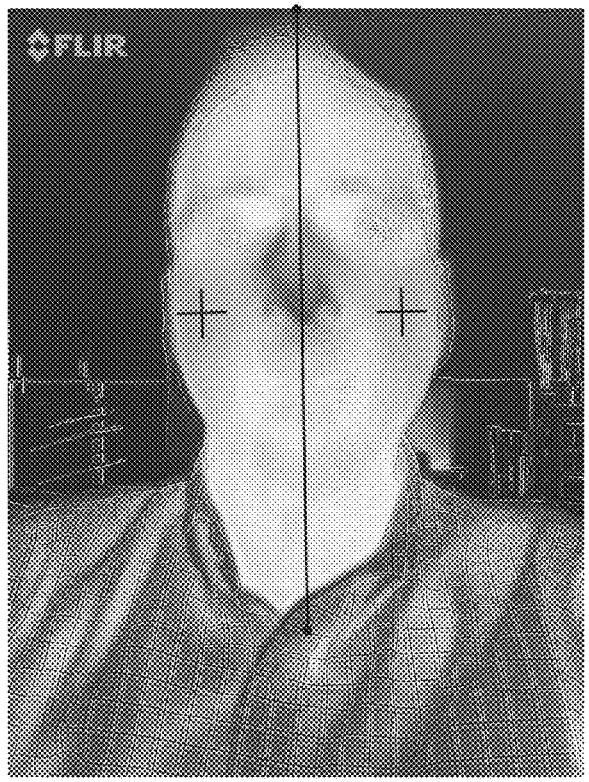

In some embodiments, a system for stroke detection may include one or more Doppler radar sensors, microphones, and cameras throughout a home to detect visual signs of stroke, equivalent to a "FAST" test using computer vision or similar techniques, as shown in FIG. 38. For example, a machine learning model may be trained on a training data set of images of stroke patients to identify asymmetrical facial features, such as facial drooping. As can be seen in FIG. 38, the system is able to identify drooping in a mouth, nose, and eye positioning of the patient. Facial capillary asymmetries via high frame-rate Eulerian video processing techniques may also be detected by the systems described herein. The system may further employ confirmation biometrics such as HR/HRV, respiratory rate (e.g., via Doppler radar), and/or bilateral temperature via infrared camera (i.e., FLIR)

In some embodiments, a device for detecting stroke may include a device positionable in a room, office, home, vehicle, or other location; or in or on a bed or other furniture (e.g., bedside monitors; monitors within mattresses, bedding, etc.). For example, a smart speaker (e.g., to prompt a user to respond to a question to analyze speech quality), microphone, camera, and/or mirror may be positionable in a location to detect changes in a user's speech, activities, movement, gait, facial appearance, heart rate, and/or heart rate variability. The device may comprise a data processing module to differentiate changes in the measured parameters as compared to that from healthy learned patient data or individualized baseline data. This can be also be referred to as reference data. The healthy learned patient data may be unique to a particular user or an aggregate value that is predetermined from previous studies. The healthy learned patient data or individualized patient data can be stored as a one or more parameters or a signature.

Figure 3:
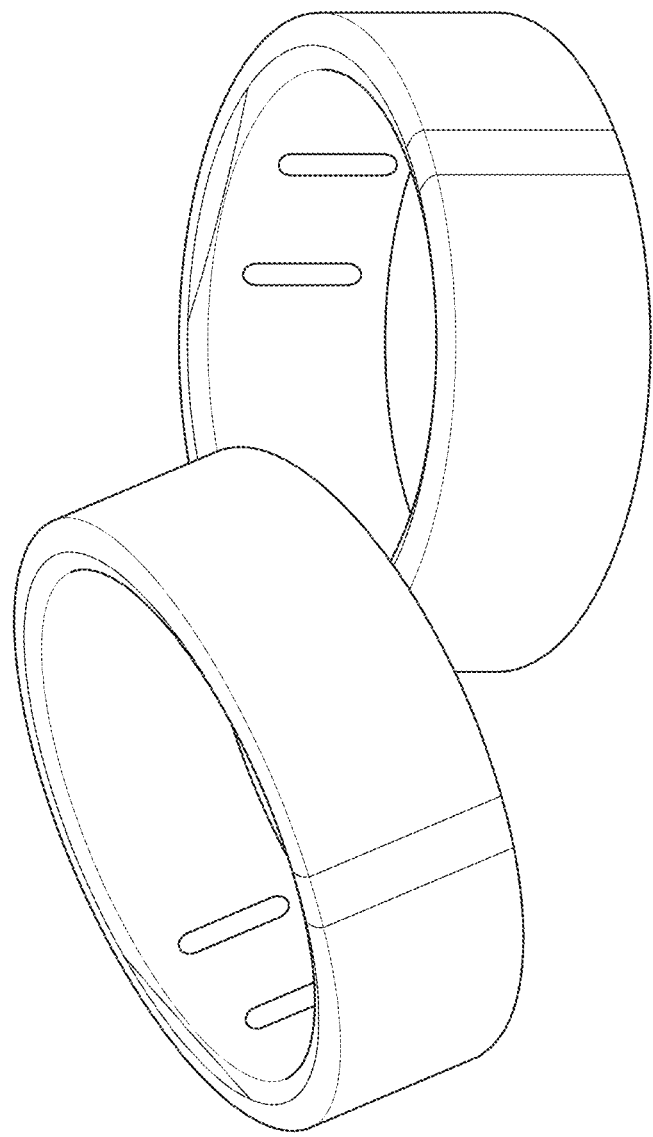
FIG. 3 illustrates one embodiment of a wearable device for stroke detection.

In some embodiments, as shown in FIG. 3, the device may be a ring or a pair of rings to be worn one on each hand or each foot to measure temperature; volumetric impedance spectroscopy; hyperhidrosis; heart rate or heart rate variability through, for example, a PPG sensor to monitor rate of blood flow; and/or motion (e.g., by including an accelerometer and/or gyroscope therein) to measure, for example, limb asymmetry or changes in gait. Temperature measurement devices may include, but are not limited to, infrared sensors, thermometers, thermistors, or thermal flux transducer. Hyperhydrosis measurement devices may include, but are not limited to, detection of analytes including ions, metabolites, acids, hormones, and small proteins through potentiometry, chronoamperometry, cyclic voltammetry, square wave stripping voltammetry, or detection of changes in conductivity. Sensor measurement devices may include, but are not limited to, a photoplethysmographic (PPG) device, a skin conductance sensor measuring skin conductance/galvanic skin response (GSR) or electrodermal activity (EDA), or a skin temperature measurement device (e.g., contact devices and non-contact devices, like IR imaging camera).

In some embodiments, the ring may incorporate a stretchable or expandable element or stretch sensor to allow the ring to expand or stretch when the finger swells. This element may include, but is not limited to, elastomer film polymers of various degree of bonding to allow for different pliable elements or measuring the reflectivity of polarized light. This element may comprise a plastic segment of the ring that can be loosened/tightened, or by building a slidable element that can be pulled apart. Non-limiting examples of a stretch sensor include, but are not limited to, a strain gauge or an electrical component configured to change inductance, resistance, or capacitance when stretched.

In some embodiments, the device may be a strip that measures brain waves through electroencephalogram (EEG) and/or muscle contractions through surface electromyography (sEMG). The measurement of EEG may be compared to a baseline value to detect a change or asymmetry of the EEG. In some embodiments, EMG measures facial muscle changes compared to a baseline measurement to identify muscle weakness and tone.

Figure 4:
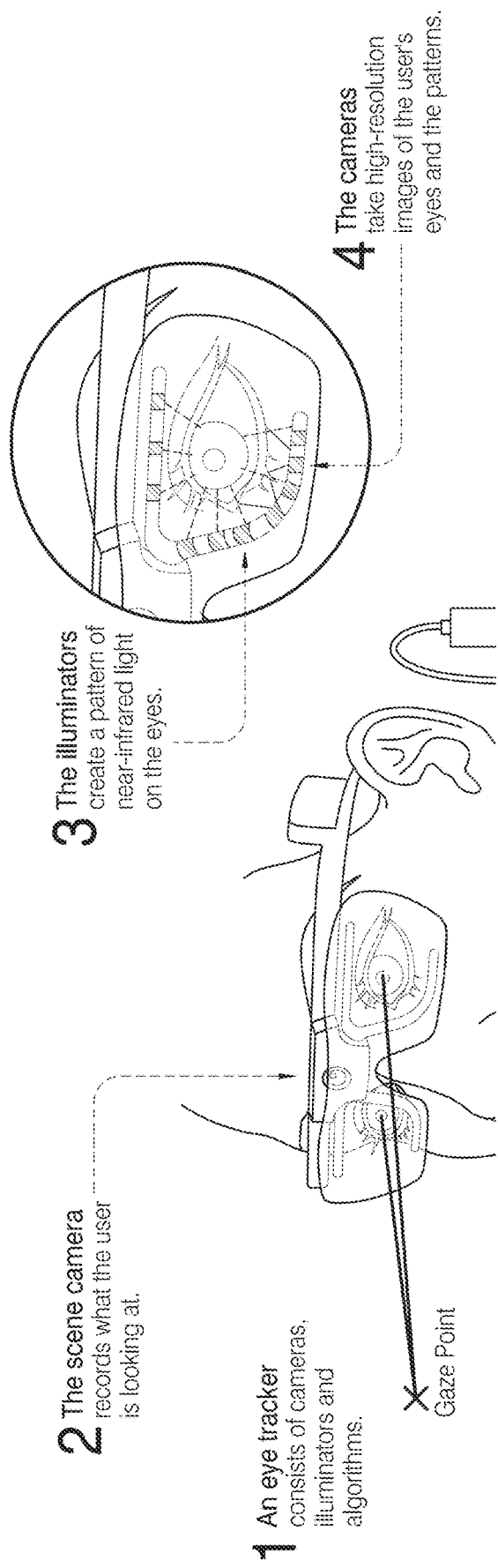
FIG. 4 illustrates another embodiment of a wearable device for stroke detection.

In some embodiments, as shown in FIG. 4, the device may be a wearable eyeglass device that measures electrooculography (EOG), EMG, EEG, gaze, and facial muscle symmetry. The measurement of EOG identifies a change in the corneo-retinal standing potential between the front and back of the eye that may detect a change in gaze and size of visual field and may be compared to either the other eye or a previous baseline value.

Figure 5:
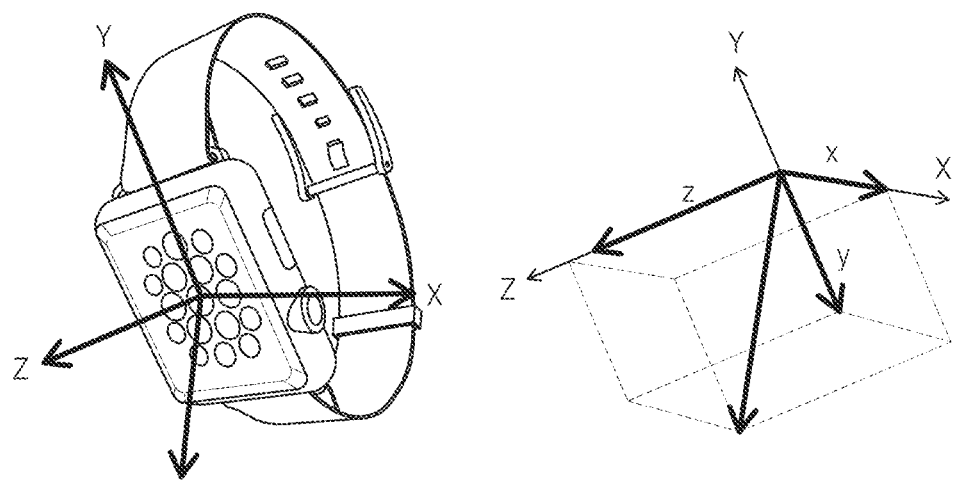
FIG. 5 shows that as a wearable device is moved so does the plane of action, causing the accelerometer to track the change of plane and accordingly adjust the movement in three dimensions.
Figure 6:
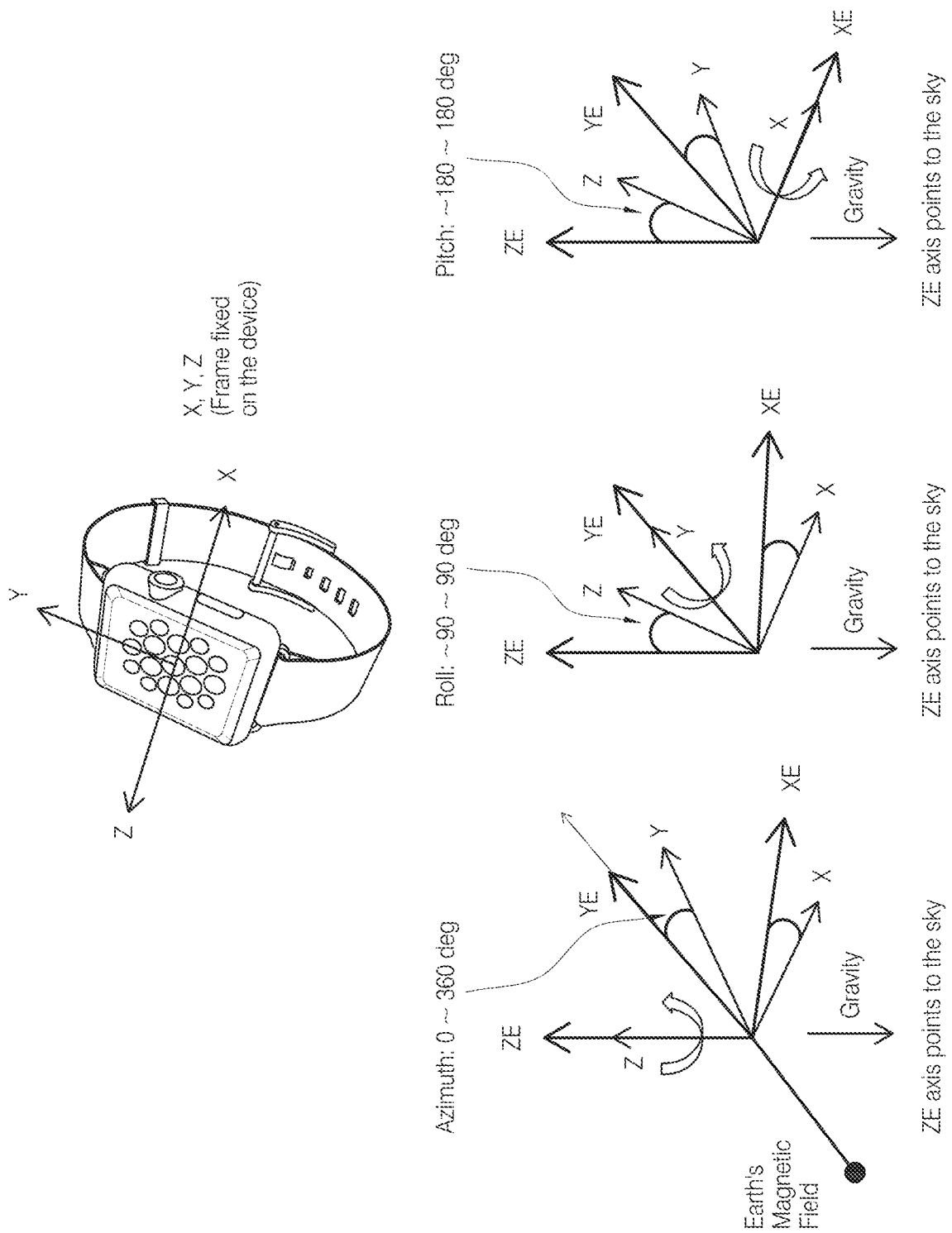
FIG. 6 shows measurement of azimuth, roll and pitch by an accelerometer.

In some embodiments, as shown in FIGS. 5-6, a device for stroke detection may include a wearable device for measuring changes in motion (e.g., in three axes), for example asymmetrical motion to detect tremors. In some embodiments, a device for stroke detection may include a wearable device for measuring changes in motion (e.g., in three axes), for example asymmetrical changes in motion to detect tremors. Such device may include an accelerometer, gyroscope, inclinometer, compass, or other device for measuring acceleration, distance, and/or movement. For example, as shown in FIG. 5, as the wearable device is moved so does a plane of action. The accelerometer may track a change of plane and accordingly adjust the movement in three dimensions. Further, as shown in FIG. 6, an accelerometer may track azimuth, roll and pitch.

In some embodiments, a device for detecting stroke may be configured to detect asymmetrical responses, outputs, or signals. For example, one or more devices (e.g., ring, watch, etc.) described herein may be used to measure symmetrical and asymmetrical limb movement. FIGS. 12-25 show various symmetrical and asymmetrical movements that may be measured by one or more embodiments described herein. For example, FIGS. 12, 15, 18, 20, 22, and 24 show various embodiments of symmetrical movements (e.g., up and down movement, left and right movement, rotational movement, etc.) between two limbs measurable by various devices described herein. FIGS. 13-14, 16-17, 19, 21, 23, and 25 show various embodiments of asymmetrical movements (e.g., up and down movement, left and right movement, rotational movement, etc.) of limbs measurable by various devices described herein.

Figure 39:
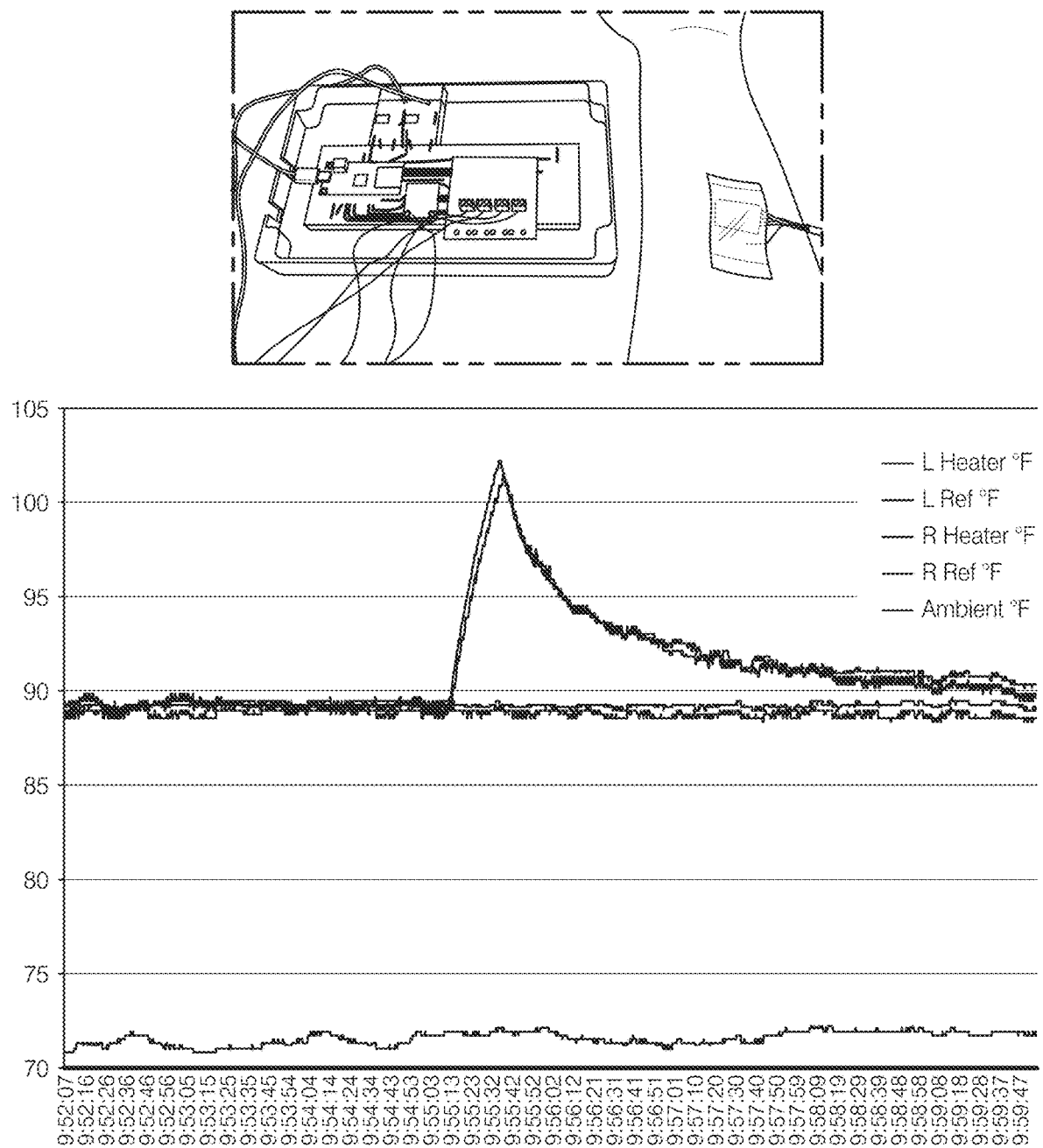
FIG. 39 illustrates an embodiment of a system for detecting stroke that is configured to stimulate a response symmetrically and measure an output of the response to determine whether the response is symmetrical or asymmetrical.

In some embodiments, as shown in FIG. 39, a device or system for detecting stroke may be configured to stimulate a response and measure the response on each side (e.g., to detect asymmetrical responses) of the body of the user to determine whether the response or the difference in response between the two sides indicates a stroke event. For example, a thermal (i.e., hot or cold) stimulus may be applied to a section of skin on a body of a user (shown in top panel) and the body's response to the thermal stimulus may be monitored over time (shown in bottom panel) to determine whether homeostasis is reached and/or a difference in response or return rate exists between the two sides of the body (in other words, determine whether an asymmetrical response exists). Further examples include stimulating the muscular or nervous system using electrical signals and monitoring the response over time and/or between sides using electromyogram (EMG), bioimpedance, or electroneurogram (ENG), respectively. These "stimulators/transmitters" and "receivers/detectors" could be in the same region or could be separated to measure across regions of the body.

As discussed above, if a stroke is detected and patients seek care quickly, it can dramatically reduce death and disability. Continuous monitoring for a stroke event may improve the response time. However, continuous monitoring of anomalous biologic events such as stroke events using existing monitors can be challenging. These monitors are cumbersome and may be difficult for users to wear over an extended period of time. In contrast, the inventors realized that wearable devices, such as watches with integrated sensors and electronics may improve continuous monitoring of stroke events. An impaired vasodilation response may be indicative of a stroke, heart failure, hypertension, diabetes, menopause, or other conditions.

Figure 40:
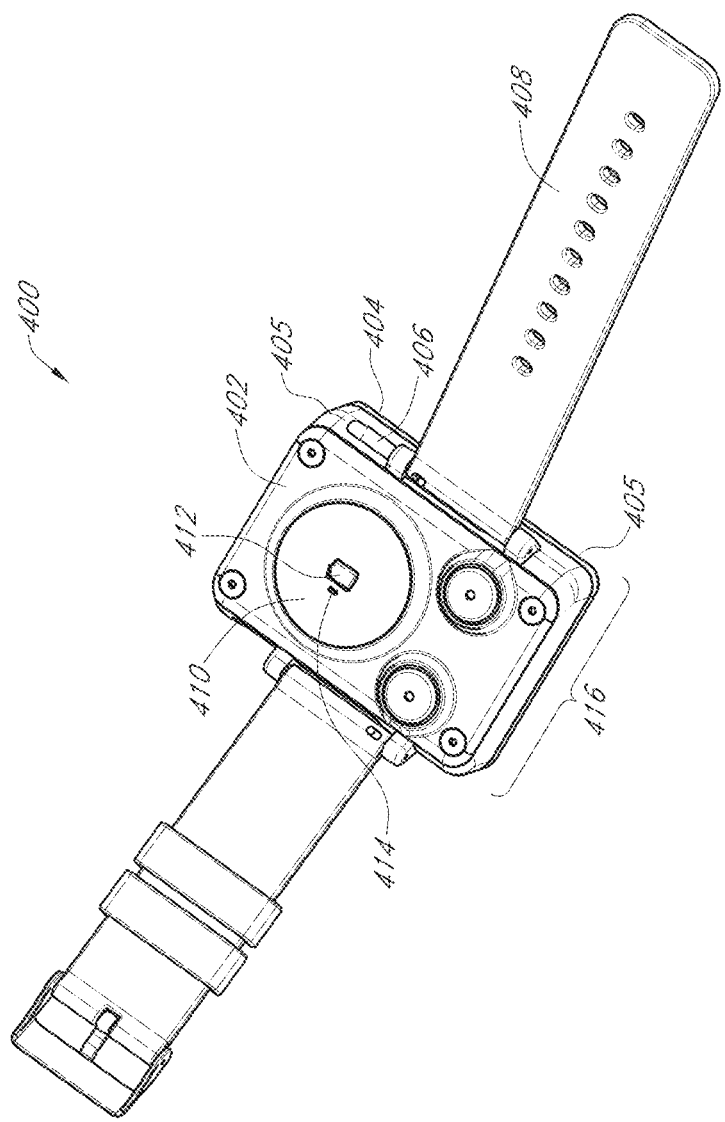
FIG. 40 illustrates an embodiment of a wearable system for detecting an anomalous biologic event.

Applying heat stress to a portion of the skin may enable detection of vasodilation response. Accordingly, systems and methods described below enable detection of impaired vasodilation in a form factor that improves continuous anomalous cardiac event monitoring. In some embodiments, as shown in FIG. 40, a system or device 400 for detecting an anomalous biologic event may function to heat a skin surface and measure a vasodilation response of the skin surface. The system or device 400 may further function to measure one or more additional parameters, biologic signals, etc. as will be described in greater detail elsewhere herein.

In one example, a system or device 400 for detecting an anomalous biologic event may include a body 416 having a first surface 404 opposite a second surface 404 in contact with the skin surface of a person. The first 404 and second 404 surfaces may be coupled via one or more or a plurality of sidewalls 405. For example, one or more sidewalls 405 may extend from a perimeter of the first surface 404 and couple to a perimeter of the second surface 402. The first 404 and/or second 402 surface may include one or more sensors positioned thereon. For example, one or more sensors on the first surface 404 may measure an environment of the user wearing or using the wearable system, and one or more sensors on the second surface 402 may measure one or more properties, features, or characteristics of the skin surface of the user and thus the user itself. Alternatively, the first surface 404 may include one or more sensors or imagers or cameras for assessing a facial region of a user, for example, via a FAST test.

Figure 41:
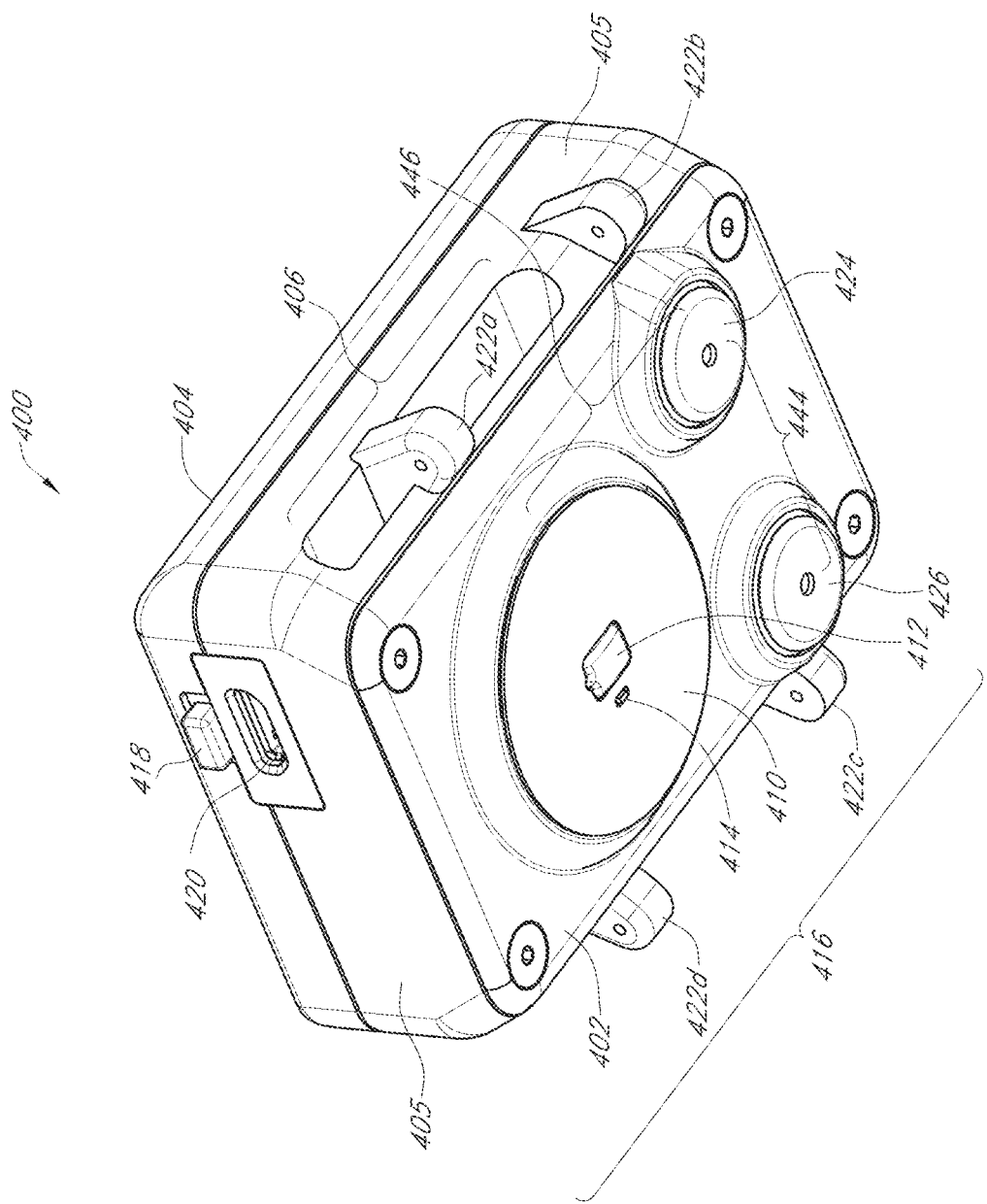
FIG. 41 illustrates another embodiment of a wearable system for detecting an anomalous biologic event.

A wearable device 400 may be secured to a user, for example a limb of a user or a skin surface of a user, via a coupling element 408, for example a tensionable band, which will be described in greater detail elsewhere herein. The coupling element 408 may be adjustable such that the wearable device may be cinched or tensioned to promote greater contact and thus coupling between the wearable device and the skin surface or tension released to reduce contact or coupling between the wearable device and the skin surface. As shown in FIG. 41, a coupling element 408 may be coupled to a body 416 of a wearable device via one or more connectors 422a, 422b, 422c, 422d. For example, a coupling element 408 may couple to a body 416 of a wearable device via a connector 422 that includes one or more pin joints, a snap fit connection to the coupling element 408, a slide and fit connection to the coupling element 408, etc. When the tensionable band 408 is coupled to the body 416 via connectors 422, the tensionable band is centered with respect to one or more sensors positioned on the second surface, so that there is sufficient coupling between the sensors and the skin surface.

Figure 50:
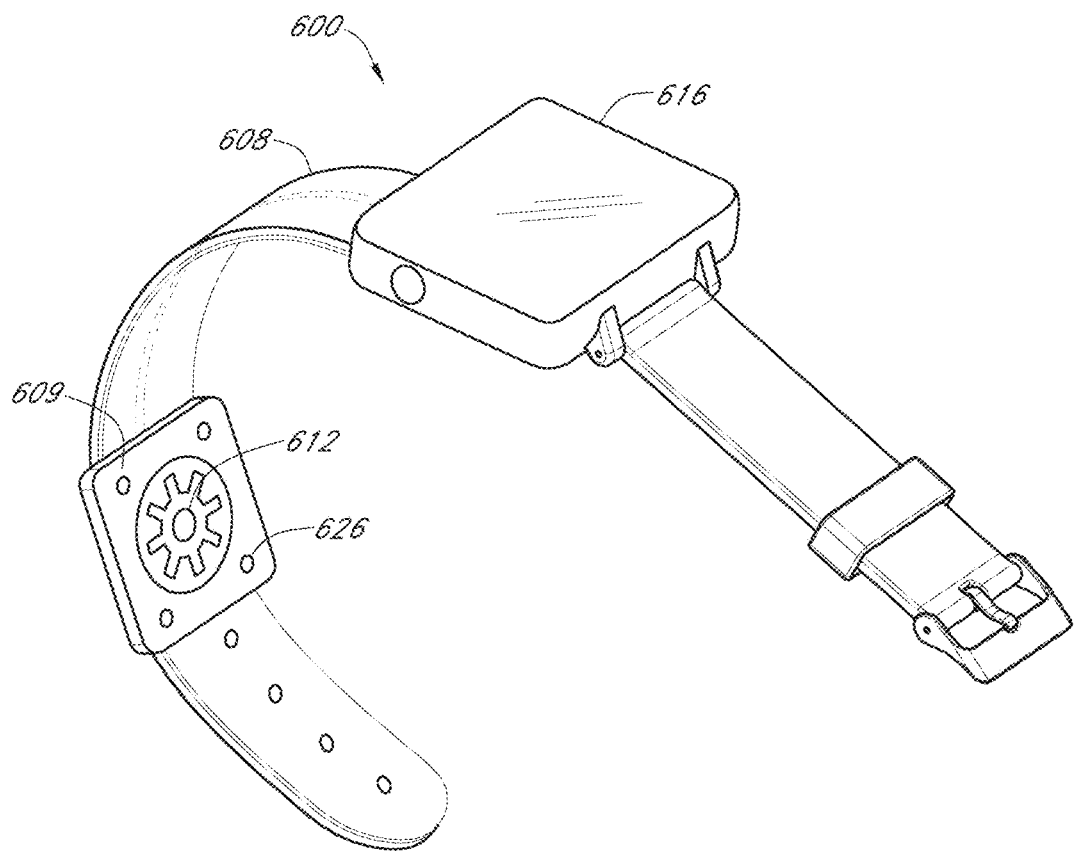
FIG. 50 illustrates another embodiment of a thermal stimulator integrated into a wearable system.

A wearable device 400 may include a heat source 410 in communication with the skin surface. The heat source 410 is configured to heat the skin surface to a target temperature or a pre-determined temperature. The heat source 410 may be a heating element; an environmental heat source, for example a warm room, warm environment (e.g., under the covers, hot day, etc.); thin film resistance flexible heater; polyimide heater; etc. In some embodiments, a heat source 410 is positioned on a second surface 402 of the body 416, so that there is coupling or contact between the heat source 410 and a skin surface. Alternatively, a heat source 610 or one or more sensors 612, 626 may be positioned on a coupling element 608 of the system 600, as shown in FIG. 50, such that the body 616 is separate from the sensor module 609 that includes the heat source 610 and the one or more sensors 612, 626. Alternatively, the heat source and/or one or more sensors may be distributed between the coupling element, body, and sensor module depending on which sensors are incorporated into the system and their specific requirements or parameters.

Figure 49:
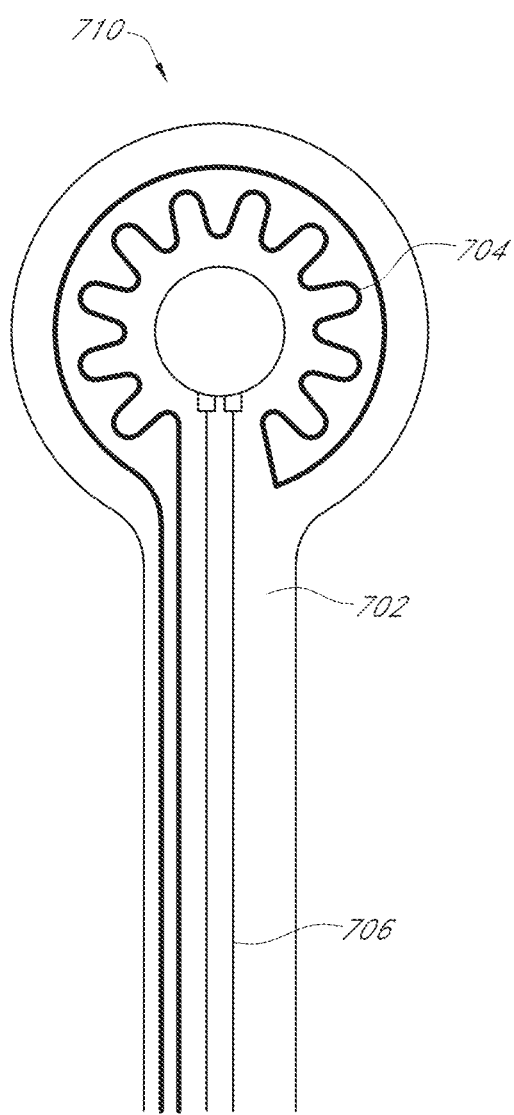
FIG. 49 illustrates an embodiment of a thermal stimulator integratable into a wearable system.

In some embodiments, as shown in FIG. 49, a heat source 710 may comprise a thermal stimulator comprising a single printed layer of resistive ink on polyimide film 702. Heat traces 704 and traces to one or more sensors 706 (e.g., blood volume sensor, infrared sensor, temperature sensor, etc.) could also be likewise printed on the polyimide film 702, as shown in FIG. 49.

Figure 51:
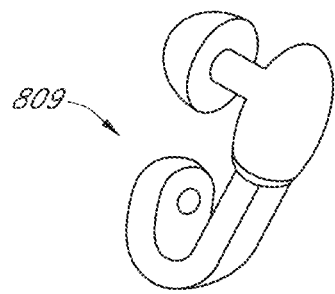
FIG. 51 illustrates an in-ear wearable system for measuring one or more biometrics.

In a still further embodiment, the sensor module 809 may be positionable in an in-ear device (e.g., ear lobe clip, ear bud, hearing aid, etc.), as shown in FIG. 51. The sensor module may be configured to measure one or more parameters, depending on which sensors are present, for example blood pressure, temperature, and/or oxygen saturation.

Further, the heat source 410 may be communicatively coupled to a hardware processor such that the hardware processor outputs a heating signal to the heat source 410 to activate the heat source to initiate a heating cycle. For example, a heating cycle may include receiving baseline temperature signals from a skin temperature sensor and an environmental temperature sensor, determining the target temperature based on the baseline temperature signals, and determining whether the target temperature is below a maximum temperature value.

In some embodiments, a target temperature may be equal to a baseline skin temperature as measured by the skin temperature sensor plus about 1 to about 20 degrees, for example about 1 to about 5 degrees, about 1 to about 10 degrees, about 5 to about 10 degrees, about 5 to about 15 degrees, about 8 to about 12 degrees, etc. In one embodiment, the target temperature is equal to the baseline skin temperature as measured by the skin temperature sensor plus about 5 to about 15 degrees. In another embodiment, the target temperature is equal to the baseline skin temperature as measured by the skin temperature sensor plus about 7 to about 13 degrees. In another embodiment, the target temperature is equal to the baseline skin temperature as measured by the skin temperature sensor plus about 10 degrees. If the target temperature is greater than a maximum temperature value, the system pauses or delays until the baseline skin temperature drops below a minimum threshold or recalculates the target temperature so that it is less than the maximum temperature value. If the target temperature is less than a maximum temperature sensor, the system proceeds to activate the heat source to heat the skin surface to the target temperature.

In some embodiments, the heat source cycles between the target temperature and a deactivated or off state or between the target temperature and a temperature that is lower than the target temperature but greater than the skin baseline temperature, for example to maintain the target temperature, hereinafter referred to as a dwell time.

In some embodiments, a duration of a heating cycle and a target temperature are interconnected and based on user preference or user perception of heat on the skin surface or a vasodilation response of the user. For example, a higher target temperature may be used for a shorter time period or a lower target temperature may be used for a longer time period.

Further, the system or device 400 may be configured to receive one or more user inputs related to a perceived heat sensation on the skin surface and/or to a sensitivity of a vasodilation response of the user. For example, a user may input that the target temperature felt too hot or too cold, for example via a user input element (e.g., button), such that the system responds by reducing the target temperature but elongating an amount of time that the skin is heated. Additionally, or alternatively, based on user preference, preset configurations (e.g., during manufacturing), or as a result of sensed data (e.g., based on sensor data), the heat source may reach the target temperature via one of a plurality of ramping functions, for example slow ramping, larger step functions, etc. Alternatively, the heat source may reach the target temperature through a plurality of microstimulations. Further, for example, a target temperature may be individualized for the user based on the sensitivity of the vasodilation response of the user.

Figure 42:
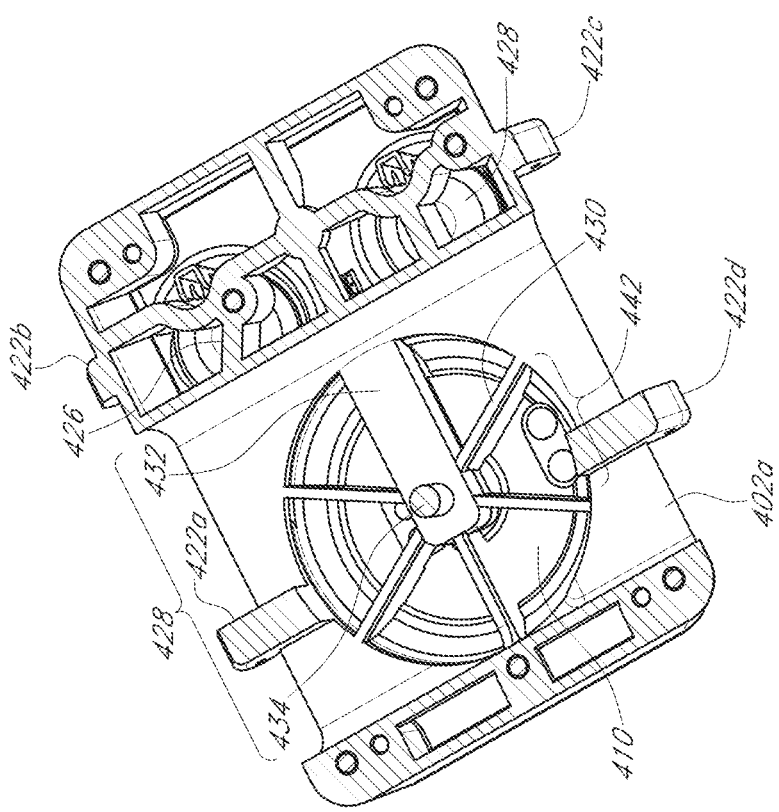
FIG. 42 illustrates a support structure coupled to the heat source of one embodiment of a wearable system for detecting an anomalous biologic event.

In some embodiments, a device or system 400 for detecting an anomalous biologic event includes a support structure 428 coupled to the heat source 410 and configured to couple the heat source 410 to the second surface 402. For example, as shown in FIG. 42, the support structure 428 includes arm 432 that extends towards or to a center of the heat source 410 to support the heat source 410 and one or more spokes 430 that extend from the arm 432 to a perimeter of the heat source 410. The spokes 430 may be substantially equally spaced from adjacent spokes 430. The spokes 430 may also be circumferentially arranged about pin or joint 434. Spokes 430 of support structure 428 further define air flow apertures 442 to allow air to interact with the heat source 410 to cool the heat source 410. Spokes 430 further define air flow apertures 422 to at least partially expose the heat source to a cavity defined by the first and second surfaces as described elsewhere herein. Alternatively, or additionally, heat source 410 may be cooled by one or more vents, a blower for passing airflow over the heat source 410, coolant, or another mechanism known to one of skill in the art.

In some embodiments, support structure 428 exerts pressure on the heat source 410 to increase contact or coupling between the heat source 410 and the skin surface. In one embodiment, the tensionable band includes a strain gauge that determines the tensile stress the band is subjected to. The strain gauge output or signal could then be visualized or displayed to a user so the user knows if the band is tensioned to an appropriate level for the heat source and/or sensor(s). Alternatively, a spring constant (k) of the material may be used to calculate the force (F=kx), so depending on how much the material is stretched (put in tension), the band could indicate that force based on the displacement. As such, the support structure 428 may comprise a flexible material, for example a flexible plastic. In other embodiments, the support structure 428 comprises a rigid material.

Further, as shown in FIGS. 40-41, a device or system 400 for detection of an anomalous biologic event further includes a skin temperature sensor 414 and a blood volume sensor 412. The blood volume sensor 412 can be integrated into a form factor such as the device or system 400 that improves continuous anomalous cardiac event monitoring. The blood volume sensor 412 can measure parameters that can provide vasodilation response. Furthermore, the skin temperature sensor 414 can also be integrated into the device or system 400. The skin temperature sensor 414 is positioned on the second surface 402 and configured to measure a temperature of the skin surface in contact with the heat source 410. The blood volume sensor 412 is positioned on the second surface 402 and configured to measure a blood volume of the skin surface. The blood volume sensor may be a photoplethysmography sensor or an impedance plethysmographic sensor. The blood volume sensor may employ light at 530 nm (green), 645 nm (red), 470 nm (blue) wavelength, or a combination thereof. Different wavelengths may be more appropriate for different applications, for example green (530 nm) light may be more accurate for heart rate measurements (e.g., heart rate variability, heart rate, etc.). In addition to, or alternatively, the blood volume sensor may be further configured to measure one or more of: heart rate, heart rate variability, or oxygen saturation.

A system or device 400 for detection of an anomalous biologic event may include an environmental temperature sensor configured to measure a temperature of the environment around the wearable system 400. For example, the environmental temperature sensor may be positioned on the first side 404 of the body 416 of the wearable system, opposite the second side 402 that includes the heat source 410. Alternatively, the system or device 400 may be communicatively coupled to an environmental temperature sensor on or in a remote computing device. For example, the remote computing device may include a laptop, a cellular device, a workstation, a server, a desktop computer, a personal digital assistant, a second wearable system or device, a netbook, or the like.

The skin temperature sensor and/or environmental temperature sensor may include a thermocouple, a resistance temperature detector, a thermistor, or an infrared temperature sensor. The type of temperature sensor selected may depend on error rate, coupling to skin surface efficiency, among other features.

In some embodiments, the heat source 410 is positioned concentrically about one or both of the blood volume sensor 412 and the skin temperature sensor 414, as shown in FIGS. 40-41. Although, a location or position of the blood volume sensor 412 and the skin temperature sensor 414 that enables coupling to a skin surface is envisioned.

A hardware processor (within the wearable system or communicatively coupled to the wearable system) communicatively coupled to the skin temperature sensor 414 and the environmental temperature sensor may be configured to perform a method comprising: receiving a first temperature signal using the skin temperature sensor and a second temperature signal using the environmental temperature sensor; and calculating a temperature differential between the skin temperature and the environment temperature. For example, if the temperature differential is below a set threshold, a difference between the target temperature and the maximum temperature value may be increased. In contrast, if the temperature differential is above a set threshold, a difference between the target temperature and the maximum temperature value may be reduced. The environmental temperature sensor may also be used in analysis of determining erroneous results, such as false positive indications of abnormalities. By comparing signals before and after stimulus and/or by comparing left versus right limb, externalities such ambient temperature response may be reduced in the analysis of abnormalities.

Further, the hardware processor may be coupled to the heat source 410 and the blood volume sensor 412. In some instances, the system 400 describe above can enable non-invasive monitoring of vasodilation and/or vasoconstriction. Human body regulates stable equilibrium through the process of homeostasis. For example, if a stimulus is applied to a body of patient, one or more homeostatic processes will attempt to counteract the effect of stimulus. For example, with respect to an induced thermal stimulus that increases or decreases temperature at a tissue site, the body will attempt to reverse the temperature change through blood flow (vasodilation or vasocontraction). Accordingly, the system 400 can induce and measure the vasodilatory response. As discussed above, stroke and other abnormalities can impair the vasodilatory response. Therefore, in some instances, it may be advantageous to monitor the change in the vasodilatory response to determine abnormalities, such as stroke. A blood volume sensor, such as optical sensors, can enable monitoring of the blood flow and correspondingly the vasodilatory response. In some instances, one or more temperature sensors (through a thermistor or optical radiation-based detectors) can also enable determination of the vasodilatory response by monitoring how quickly the temperature of the skin returns to equilibrium following the stimulus. In some examples, the vasodilatory response is correlated with a rate of change or slope in the measured parameter, such as blood volume parameters, temperature, and others discussed herein. In additional examples, the vasodilatory response can be correlated with a steepness of the rate of change. This can be calculated using a second derivative.

Figure 46A:
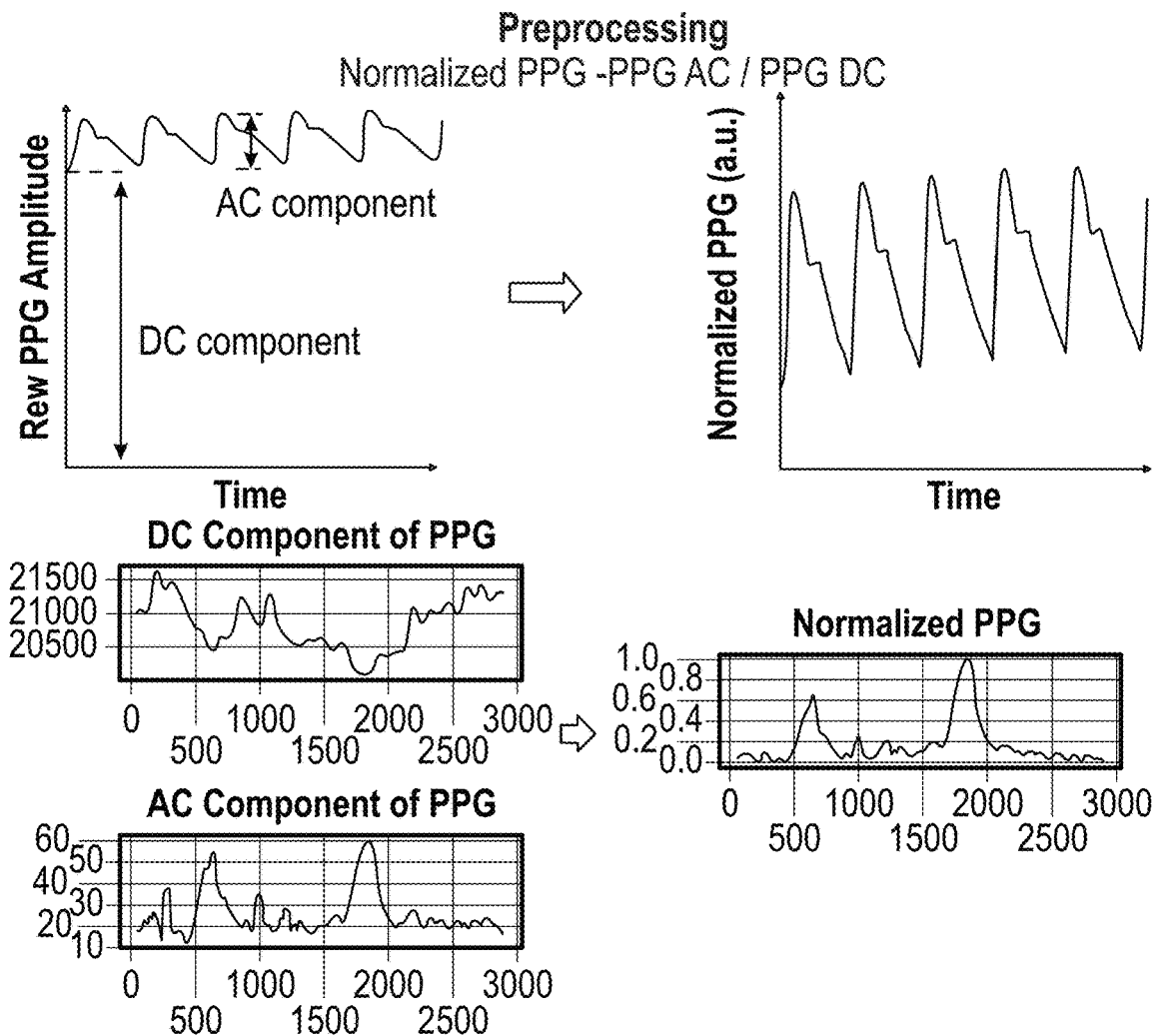
FIG. 46A illustrates in graph form a method of processing a signal received from a blood volume sensor.
Figure 46B:
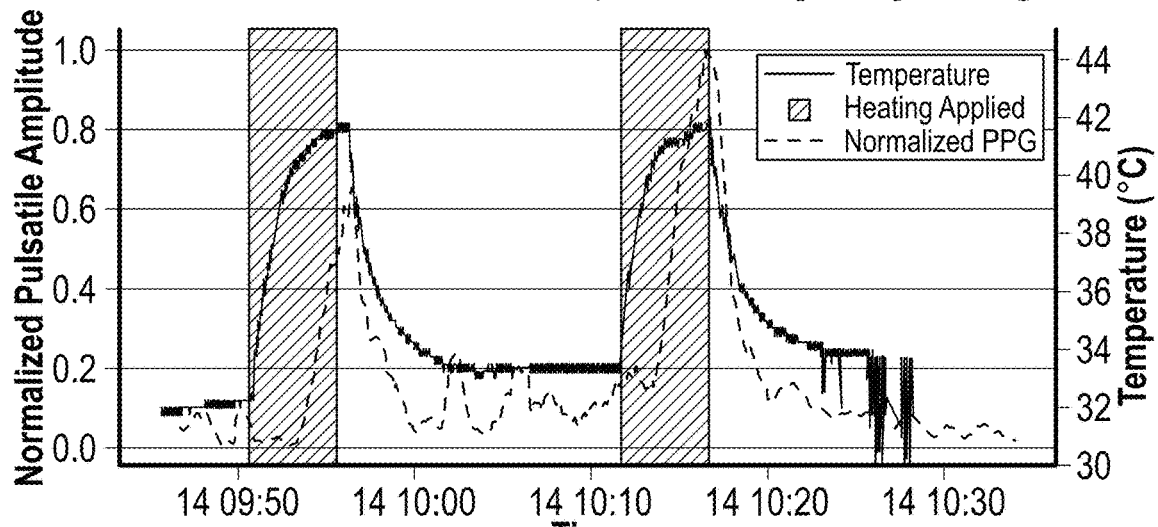
FIG. 46B illustrates in graph form a method of monitoring a heating cycle and a corresponding vasodilation response over time.
Figure 47:
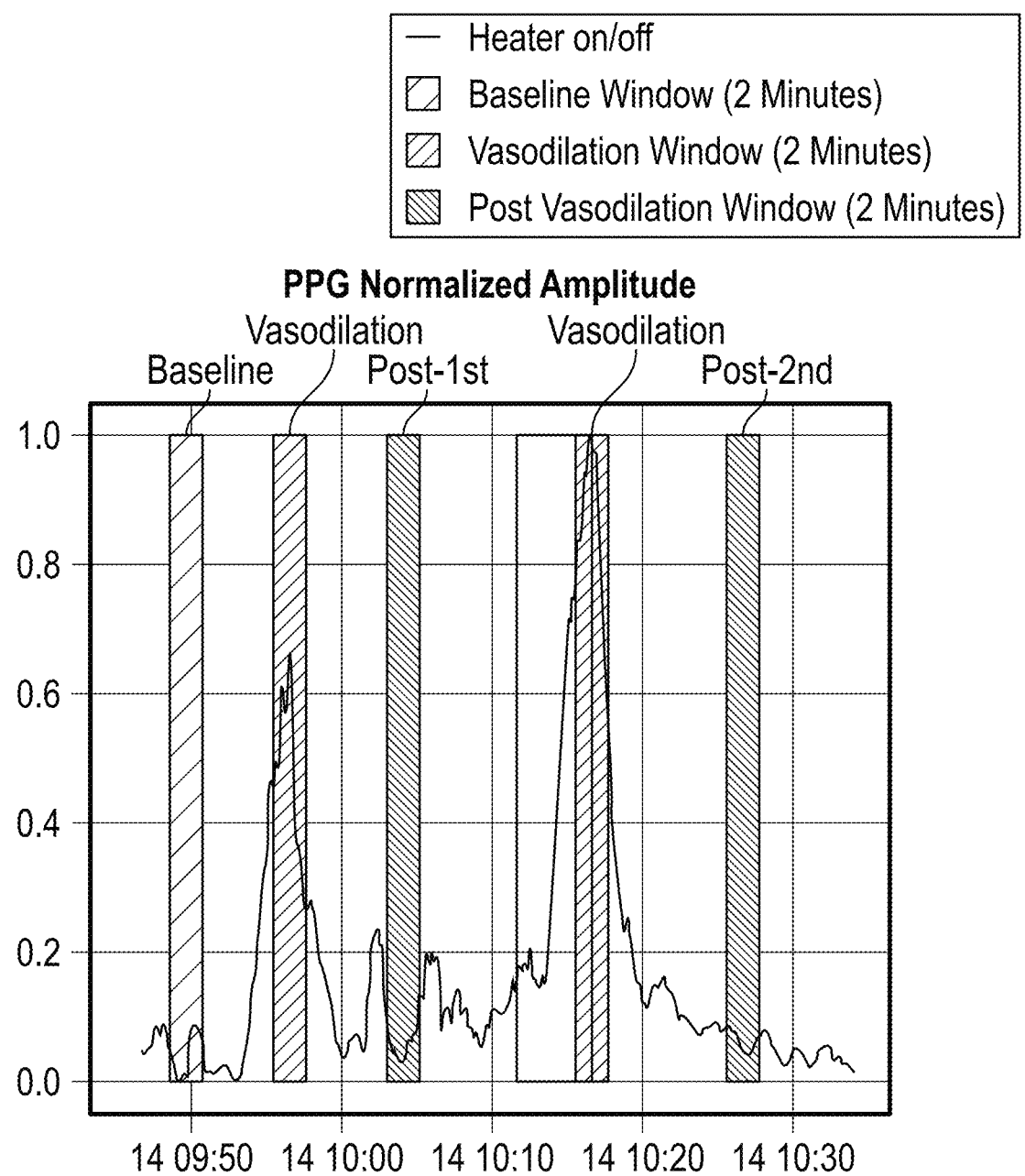
FIG. 47 illustrates in graph form a vasodilation response of a skin surface over time and in response to application of heat.

In some instances, it can be advantageous to use a combination of a heat source 410 and the blood volume sensor 412 to improve cardiac monitoring. The heat source 410 and the blood volume sensors 412 can be integrated into a form factor that a user can wear for continuous monitoring. The measurements can be repeated non-invasively without significant discomfort to the patients. Furthermore, as shown in FIGS. 46A-B and 47, the response time between the application of heat and the change in blood volume is relatively small. This can enable a relatively fast determination of the anomalous biologic event. Therefore, it can be advantageous to integrate a heat source and a blood volume sensor in any wearable system disclosed herein to improve continuous cardiac monitoring. In some instances, a Peltier cooler can be used as a thermal source instead of or in addition to the heat source 410.

Furthermore, in some instances, the stimulus can be an electrical stimulus in addition to or instead of the thermal stimulus. For example, the system 400 may include a plurality of electrodes for inducing and/or measuring electrical activity across a tissue site. Electrical activity can include bioimpedance for detecting high or low muscle tone, which can occur with hemiplegia. The system 400 can include at least two electrodes. In some instances, the system 400 can include at least four electrodes. For example, the system 400 can include two pairs of electrodes for measurement of bioimpedance. These four electrodes may positioned on the second surface 402. The electrodes may also be positioned on the strap 408 or an external accessory that can attach the system 400. Bioimpedance can measure muscles both inter and trans cellularly which could be used to detect hemiparesis and could be used for both detection as well as rehabilitation. The EDA electrodes can also be mounted anywhere along the second surface facing the skin to the strap 408. Furthermore, the system 400 can also include six or more electrodes. The electrodes can be integrated on the system 400 such that they are in contact with the skin tissue of the user.

As discussed above, an optical sensors, such as the blood volume sensor 412, can interrogate a target tissue to determine parameters that correlate with the vasodilatory response. Other sensors can also be used to extract parameters for determination of the vasodilatory response. For example, the system 400 can use minimally invasive and/or invasive sensors to determine hemodynamic parameters, such as cardiac output, to provide an indication of the vasodilation response. The system 400 can also include on or more electrical based sensors, such as bioimpedance sensors, EDA sensors, ECG sensors, EEG sensors, EMG sensors, and the like. Electrical sensors may enable measurement of hydration, skin conductance, bioimpedance, and other electrical parameters that relate to hemodynamic function or measure electrical signaling of neural activity and its effect. Furthermore, the system 400 can include one or more ultrasound sensors to obtain hemodynamic parameters. Temperature sensors can also enable determination of the vasodilation response. Accordingly, the system 400 can include a combination of some or all of the sensors discussed above to extract one or more parameters that correlate with hemodynamic function or maintenance of homeostasis.

The following table illustrates example physiological phenomena and corresponding parameters that can be monitored:

| Physiological Phenomena | Data Output |
|---|---|
| Bilateral electrodermal activity (EDA) | Skin conductance response |
| Autonomic regulation of vasomotor response to maintain homeostasis | Blood flow amplitude, systole and diastole interval, transient vasodilation and vasoconstriction |
| Temperature decay pattern upon thermal stimuli | Transient temperature versus time output |
| Oxygen saturation | IR absorption oxygenated hemoglobin to deoxygenated hemoglobin |
| Motion asymmetry | Actigraphy |
| Bilateral temperature difference | Skin temperature |
| Ambient conditions | Ambient temperature |
| Changes in muscle tone (hemiparesis) and hydration (hydrosols) | Bio impedance (BIA) |

Patients are often monitored in neuro ICU after a stroke. This can be expensive as a nurse needs to conduct periodic checks on the patient. Accordingly, the system 400 can enable improved monitoring without requiring the patient to be in the neuro ICU and/or without requiring a caregiver to conduct periodic checks. While the system 400 is described as a wearable system, in some examples, some or all of the components of the system 400 may be positioned in proximity to the user but not directly attached or worn by the user. For example, when a user needs to be monitored in a hospital environment, some or all of the components of the system 400 can be positioned in proximity to the user's hospital bed. For example, the thermal stimulus source can include a laser.

Figure 52:
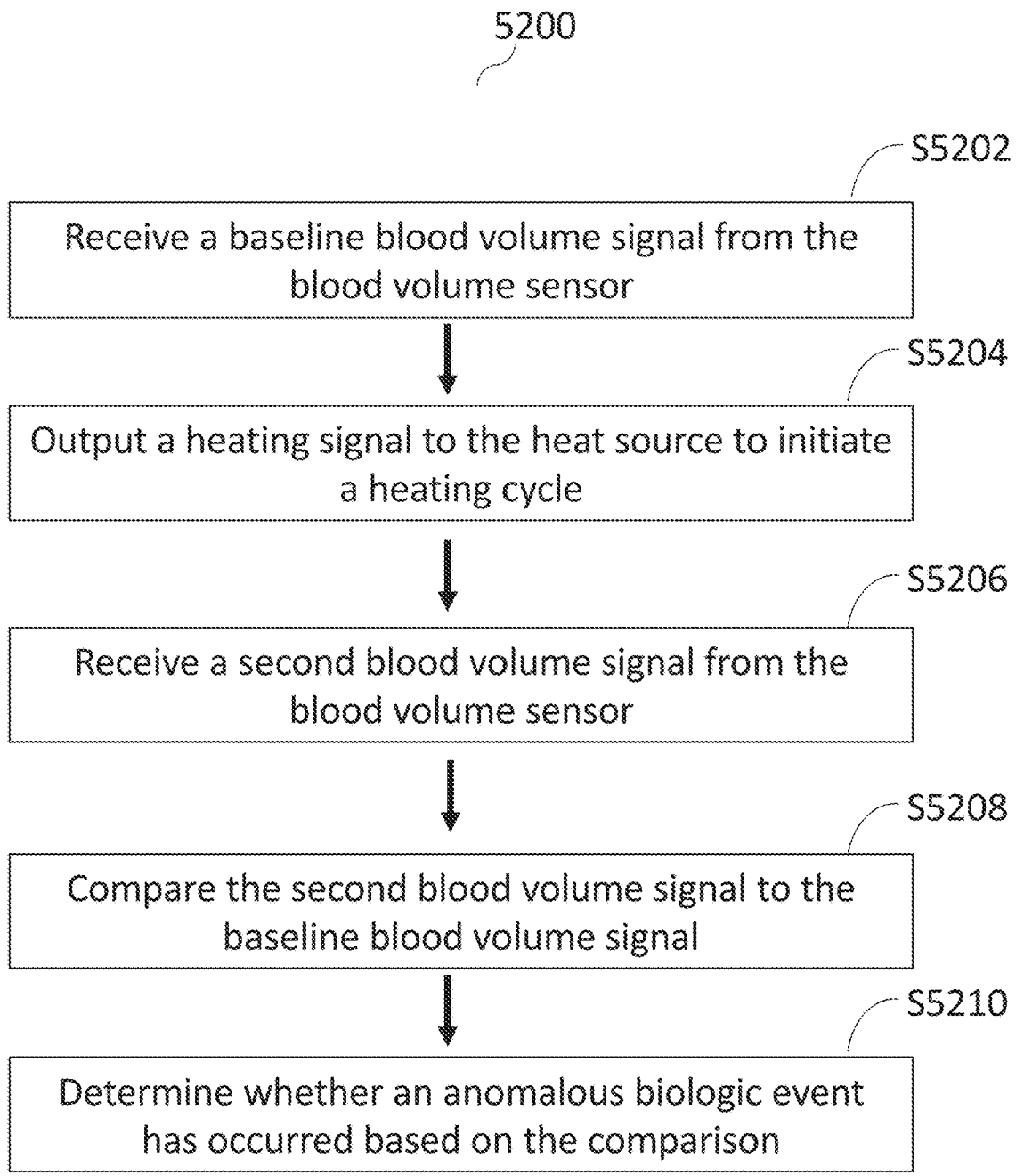
FIG. 52 illustrates a method of detecting an anomalous biologic event.

As such, the hardware processor may be configured to perform the method, as shown in FIG. 52, which includes: receiving a baseline blood volume signal from the blood volume sensor S5202, outputting a heating signal to the heat source to initiate a heating cycle S5204, receiving a second blood volume signal from the blood volume sensor S5206, comparing the second blood volume signal to the baseline blood volume signal S5208, and determining whether an anomalous biologic event has occurred based on the comparison S5210. The steps of the method may be repeated at least once, one or more times, a plurality of times, on a loop, according to physician, caregiver, or user preferences, or otherwise.

In some embodiments, the second blood volume signal is a set of blood volume signals, such that the blood volume of the skin surface is measured repeatedly before, during, and/or after a heating cycle of the heat source. The blood volume of the skin surface may be measured at a pre-set interval, for example every about 10 ms to about 1 sec, about 1 sec to about 5 sec, about 5 sec to about 10 sec, etc. Alternatively, the blood volume of the skin surface is measured randomly or only upon detection of a change in temperature of the skin surface or upon detection of a change in vasodilation by the blood volume sensor. A measurement frequency may be individualized for a user, for example if a vasodilation response of a user in response to heat is very sensitive, a reduced frequency of blood volume measurements may be needed. In contrast, if a vasodilation response of a user in response to heat is less sensitive, an increased frequency of blood volume measurements may be needed.

In some embodiments, the second blood volume signal is a plurality of blood volume signals, such that the blood volume of the skin surface is measured continuously before, during, and/or after a heating cycle of the heat source.

In some embodiments, block S5206 includes receiving the second blood volume signal after the target temperature is reached, after a predetermined length of time has expired, after a dwell time (i.e., cycling heat source on and off during a heat cycle or cycling heat source between target temperature and lower temperature during a heat cycle) has expired, or after one or more heating cycles have concluded. A frequency of sampling and/or sampling relative to a heat cycle (before, during, or after the heat cycle) may be based on a user's biology, such that the sampling is individualized.

In some embodiments, block S5208 includes calculating a baseline ratio of alternating current (AC) to direct current (DC) for the baseline blood volume signal and a second ratio of AC to DC for the second blood volume signal and comparing the baseline ratio to the second ratio, as shown in FIG. 46A. The methodology and rationale for the AC to DC ratio is described in Tusman et al. "Advanced uses of pulse oximetry for monitoring mechanically ventilated patients." *Anesth Analg* 2017; 124: 62-71, which is herein incorporated by reference in its entirety. The top left panel of FIG. 46A shows raw PPG amplitude data and the respective DC and AC components of the signal. Taking the ratio of AC to DC of the raw signal yields the top right panel. During a two-heating cycle experiment, PPG data in the lower left panel was collected. The AC and DC components of the signal are represented in separate, stacked graphs. When the AC to DC ratio is calculated for this two-heating cycle experiment, a normalized PPG signal is achieved, which is shown in the lower right panel. The same PPG data is shown in FIG. 46B overlaid with heat cycle data. As shown, the temperature of the skin surface reaches the target temperature (i.e., about 42 C) in each heat cycle, shown by the shaded portions of the graph. The perfusion index or normalized PPG signal similarly spikes during each heat cycle in response to the application of heat. FIG. 47 shows the same data as FIGS. 46A-46B with additional definition of baseline, vasodilation, and post vasodilation windows. The heat cycle was off for 5 min, on for 5 min, off for 15 min, on for 5 min, and off for 10 min. The time windows selected for comparison were: a baseline time window (e.g., minimum 2 minutes before "heat source first on"), a vasodilation time window (e.g., maximum 2 minutes of "heat source on"), a first post vasodilation time window (e.g., minimum 2 minutes after "heat source first on"), and a second post vasodilation (e.g., minimum 2 minutes after "heat source second on"). As shown in FIGS. 46A-47, application of heat elicits a vasodilation response that is reproducible over multiple cycles.

Figure 45:
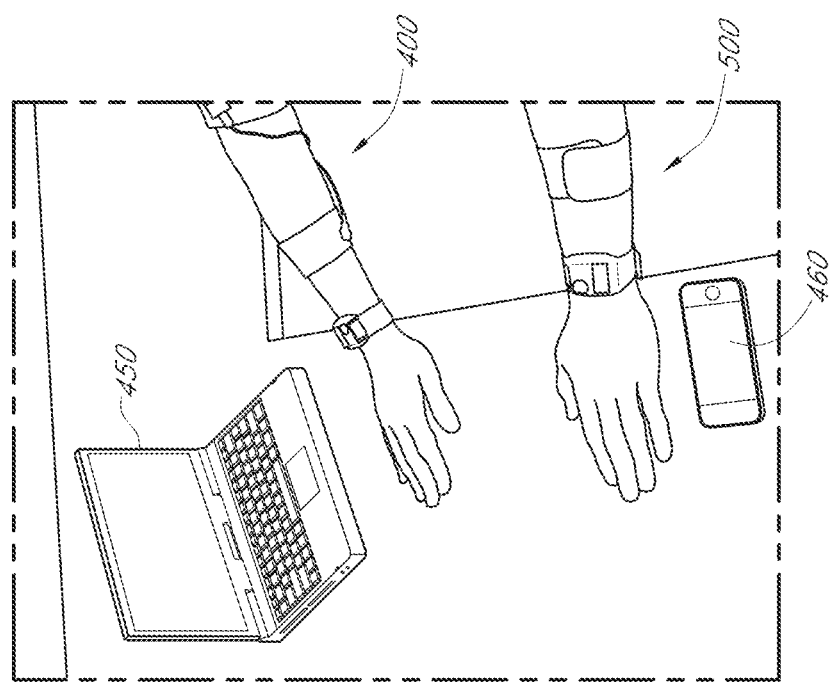
FIG. 45 illustrates a first and second wearable system for measuring response asymmetry across a right and left limb, respectively.

As discussed above, tracking a vasodilation response can be used in monitoring abnormalities, such as stroke. However, the vasodilation response in a user can be affected by several sources that are unrelated to the stroke or the abnormality that is being monitored. Accordingly, using the system 400 in only one tissue site may result in false positives. It was observed by the inventors that by monitoring multiple tissue sites, the monitoring results may more closely track the abnormalities and reduce erroneous results. FIG. 45 illustrates a first system 400 and a second system 500 placed approximately symmetrically on the right and left limbs. Accordingly, if a stimulus is applied approximately in synchronization between the first system 400 and the second system 500, the degree of symmetry or asymmetry in the measurements responsive to the approximately simultaneous stimulation can be used in the determination of stroke and reduction of erroneous results. While the disclosure herein provides stroke as an example of abnormalities, the system 400 and the methods described herein can also be used to monitor other abnormalities. For instance, other abnormalities or physiological deviation can include menopause, diabetes, and peripheral blood circulation disorders that can affect peripheral blood circulation. In some instances, menopause, diabetes, and other disorders may affect all parts of the body or may affect certain parameters uniformly. For example, vasodilation response may be impaired uniformly in conditions like menopause compared to a stroke where there is a high likelihood of asymmetry. Accordingly, a stroke can be differentiated from these other abnormalities and vice versa based on the asymmetry observed in the vasodilation response and other multilateral measurements. In another example, the vasodilation response may be affected, but the electrical measurements described herein using EDA and bioimpedance may remain the same. Accordingly, the asymmetry in measurements may also be used to determine abnormalities.

Figure 48:
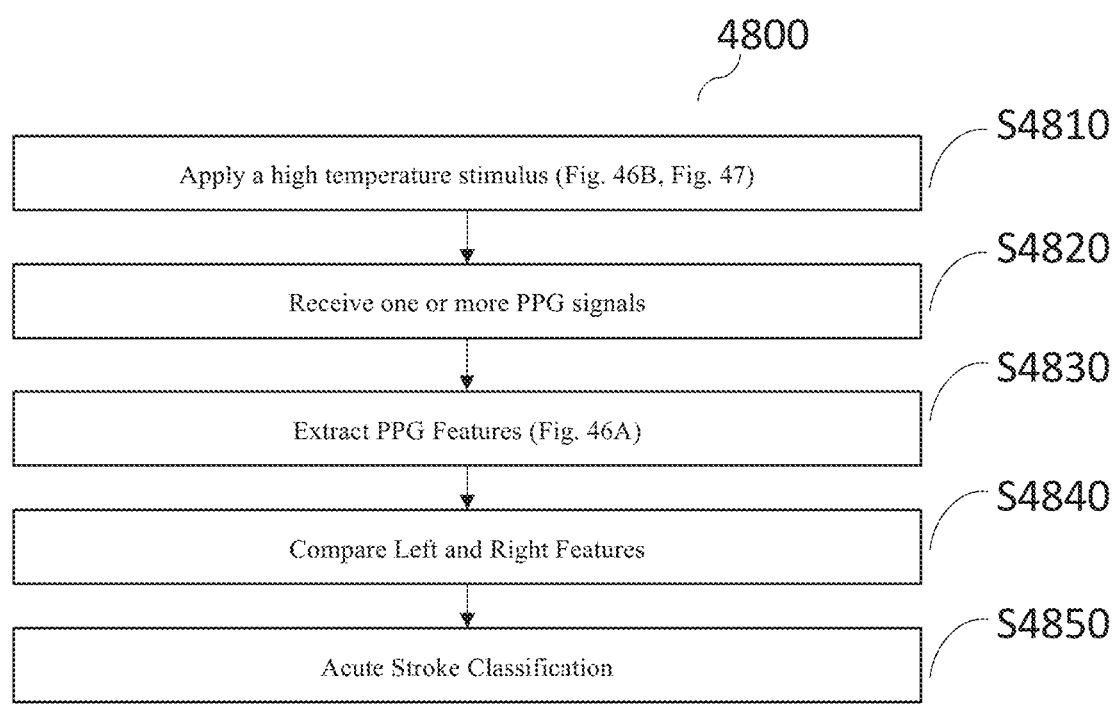
FIG. 48 shows a method of detecting an anomalous biologic event by measuring a vasodilation response of a skin surface over time in response to application of heat.

In some embodiments, as shown in FIG. 48, a method 4800 of detecting an anomalous biologic event includes: applying a high temperature stimulus (e.g., shown in FIGS. 46B-47) S4810; receiving one or more signals indicative of a blood volume, blood flow, or blood perfusion in a tissue of the user in response to the high temperature stimulus S4820; extracting one or more features of the one or more signals S4830; comparing the one or more features for a right side and a left side of the user (e.g., right and left limbs, as shown in FIG. 45) S4840; and calculating an acute stroke classification score S4850. Furthermore, the method 4800 can optionally compare baseline measurements prior to the application of the stimulus and after the application of stimulus, as discussed in more detail with respect to FIG. 52 for both left and right limbs. During multiple tissue site monitoring, such as the left and right limb monitoring as shown in FIG. 45, the system 500 may include all the same components as the system 400 described above. In other cases, the system 500 may include less components than system 400. For example, both systems may not require a display. Additionally, one of the systems may include computational capabilities while the other one collects the data and transmits to the paired system for computation. Therefore, one of the systems 400 and 500 may not include a hardware processor. Accordingly, the system 400 and 500 may operate in a master-slave configuration. The systems 400 and 500 may be paired wirelessly via Bluetooth or other wireless protocol. In some instances, the systems 400 and 500 may be paired with an external computing system, such a patient monitor, a hub, or a smartphone.

In some embodiments of block S4830, the one or more features include, but are not limited to, an amplitude or a systolic or diastolic wave, a waveform shape, a waveform complexity, a perfusion index (i.e., a relationship between the pulsatile (AC) and the non-pulsatile (DC) components of PPG signal), DC offset, a stiffness index (i.e., time between peaks of forward and backward waves along the vascular tree; h/ΔT, where h is a patient's height), a reflection index (i.e., a ratio between the heights of the backward and the forward waves; B/A×100), a notch position (i.e., position of the dichrotic notch; e.g., with vasoconstriction, the position moves toward the left into the systolic wave), a peak to peak phase shift, slope onset of temperature signal and/or blood volume signal, slope decay of temperature signal and/or blood volume signal, midpoint of rising slop of temperature signal and/or blood volume signal, a vasodilation response as an indicator of a collateral state of the brain and/or heart, etc.

In any of the embodiments described herein, a wearable system or device for detecting anomalous biologic events may include one or more electrodermal activity sensors positioned on the second surface and/or a tensionable band of the system. For example, as shown in FIG. 41, electrodermal sensors 424, 426 are positioned on the second surface 402 of the wearable system 400. Electrodermal sensors 424, 426 may be spaced apart from one another by distance 444, which equals about 5 mm to about 10 mm, about 10 mm to about 20 mm, about 20 mm to about 30 mm, about 30 mm to about 40 mm, about 40 mm to about 50 mm, about 50 mm to about 60 mm, about 60 mm to about 70 mm, about 70 mm to about 80 mm, about 80 mm to about 90 mm, about 90 mm to about 100 mm, measured from a center point of each sensor. Further, electrodermal sensors 424, 426 may be spaced apart from the heat source by distance 446, which equals about 10 mm to about 20 mm, about 20 mm to about 30 mm, about 30 mm to about 40 mm, about 40 mm to about 50 mm, about 50 mm to about 60 mm, about 60 mm to about 70 mm, about 70 mm to about 80 mm, about 80 mm to about 90 mm, about 90 mm to about 100 mm, measured from a center point of the sensor and a center point of the heat source.

Figure 56:
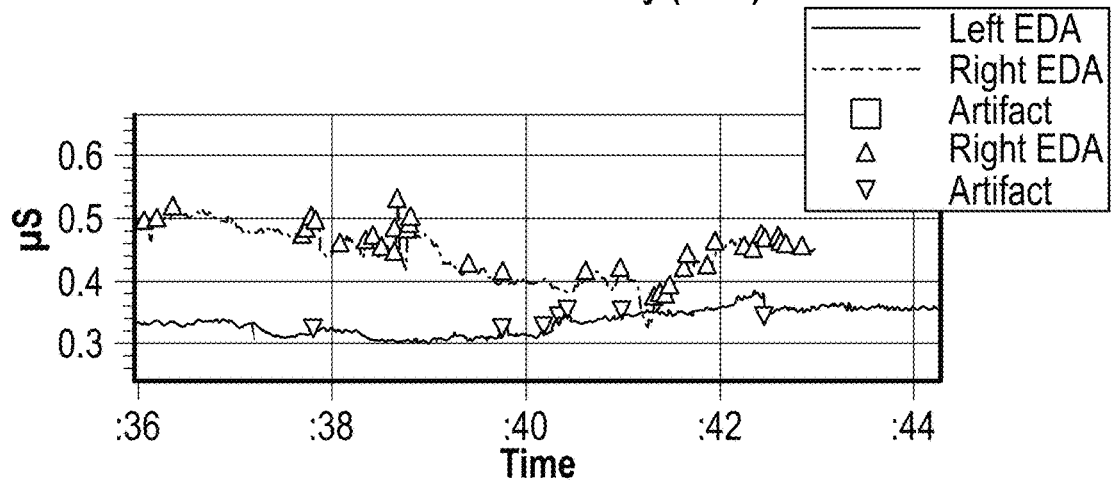
FIG. 56 shows a graph comprising asymmetrical electrodermal activity data for detecting an anomalous biologic event.
Figure 57:
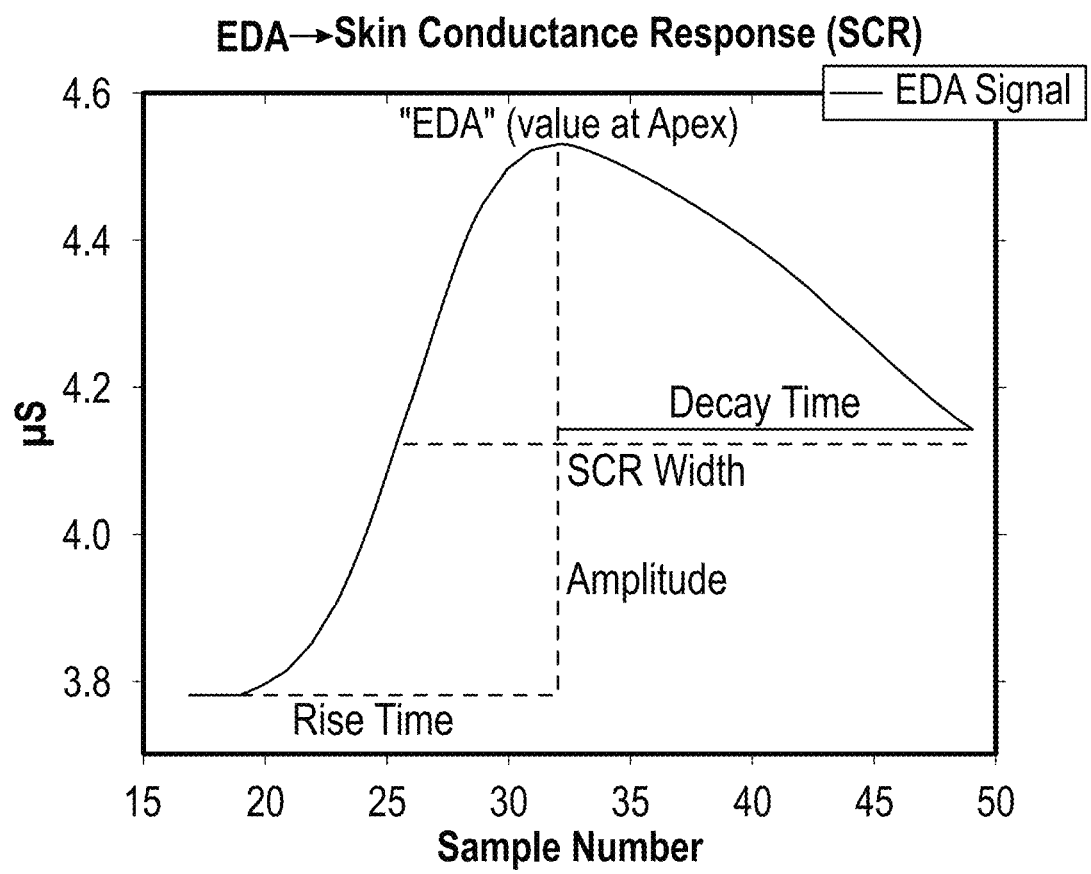
FIG. 57 shows a graph comprising various parameters of interest in electrodermal activity data.

As shown in FIG. 56 as one example, electrodermal activity (EDA) of a skin surface of a user may be measured overtime. Left side and right side electrodermal activity may be measured over time and compared. FIG. 56 shows left and right side electrodermal activity including events (shown as triangles) potentially indicative of an anomalous biologic event. A signal collected by an electrodermal activity sensor may be processed to extract one or more features. For example, as shown in FIG. 57, one or more features may include a rise time (i.e., start of the SCR to the apex), an amplitude (i.e., EDA at apex minus an EDA at start of the SCR), a skin conductance response (SCR) width (i.e., between the 50% of the amplitude on the incline side and 50% of the amplitude on the decline side), a decay time (i.e., time from apex to 50% of the amplitude), an area under the curve (i.e., SCRwidth multiplied by amplitude), Maximum derivative of SCR, and/or an apex value.

Figure 63:
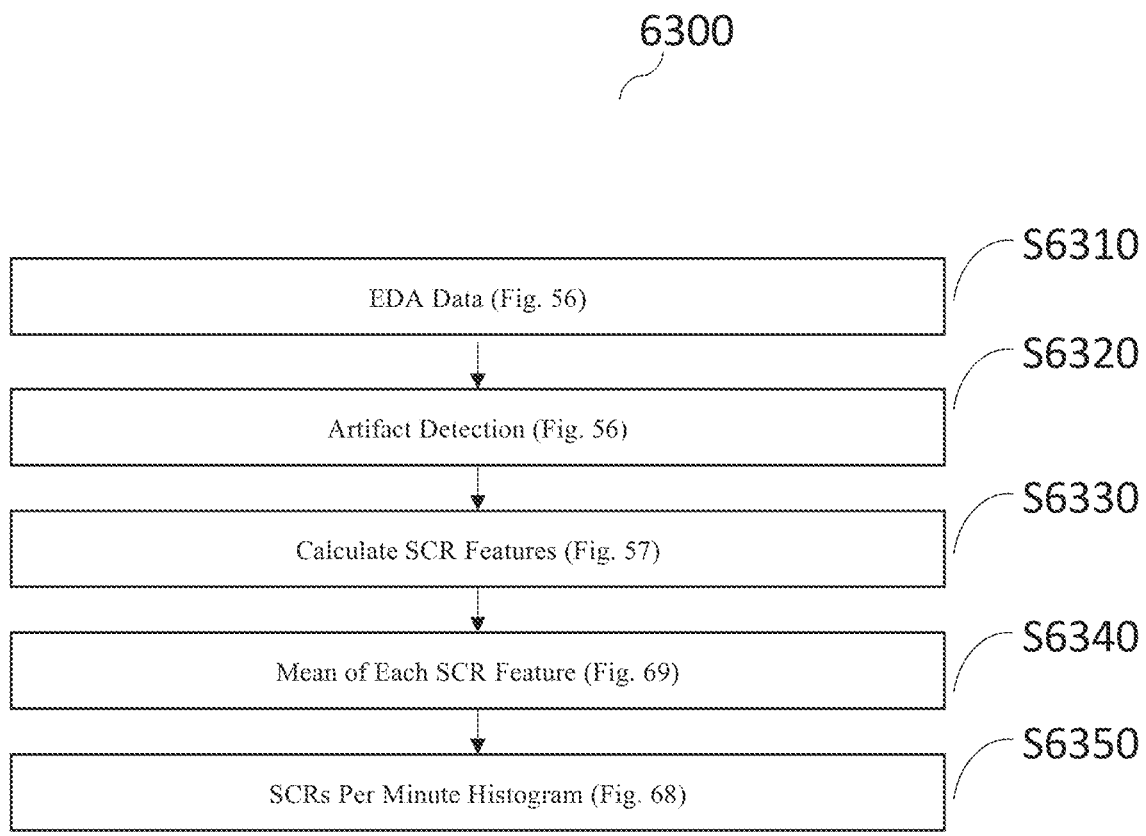
FIG. 63 shows a method of measuring a skin conductance response.
Figure 64:
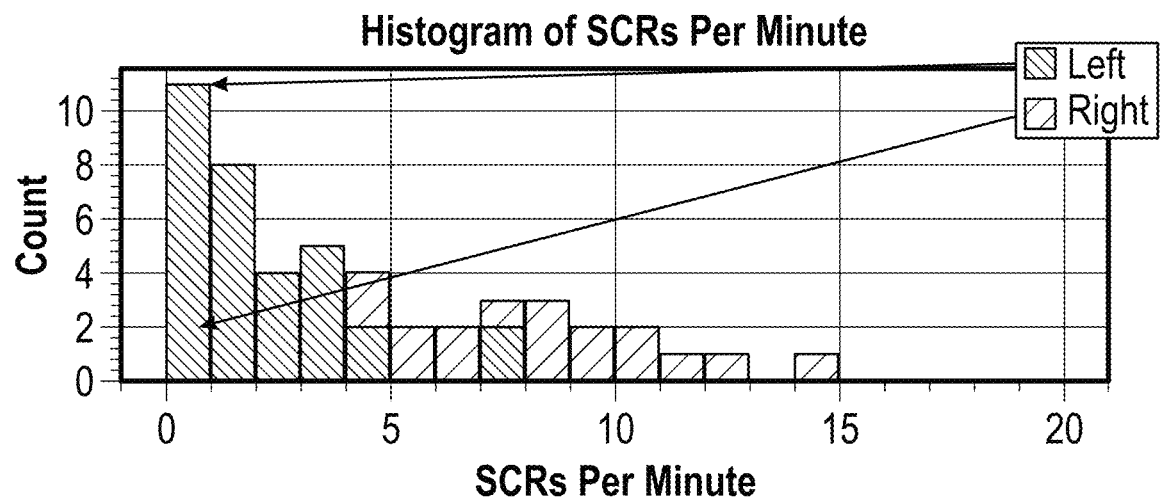
FIG. 64 shows a graph comprising asymmetrical skin conductance response over time.
Figure 65:
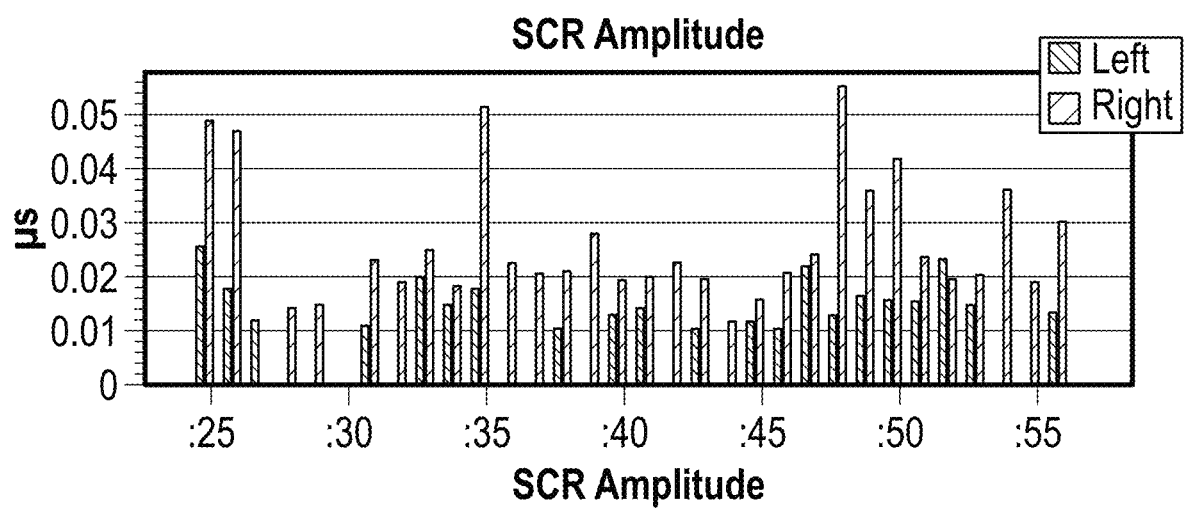
FIG. 65 shows a graph comprising amplitude of an asymmetrical skin conductance response over time.

FIG. 63 shows a method 6300 of analyzing EDA data, and FIGS. 64-65 show representative EDA data. A method 6300 for analyzing EDA data includes: receiving signals from one or more EDA sensors (e.g., as shown in FIG. 56) S6310; detecting and/or removing one or more artifacts (e.g., as shown in FIG. 56) S6320; calculating or extracting one or more skin conductance response (SCR) features (e.g., as shown in FIG. 57) S6330; calculating a mean or average of one or more features S6340; and calculating an SCR for a period of time S6350. For example, SCR amplitude is shown graphically in FIG. 65 for one-minute intervals. As shown, for this individual, SCR amplitude varies over time and asymmetrically (i.e., comparing right vs. left response). Further, if the SCRs per minute are compared for left and right responses, as shown in FIG. 64, the SCR per minute varies over time and asymmetrically.

Figure 43:
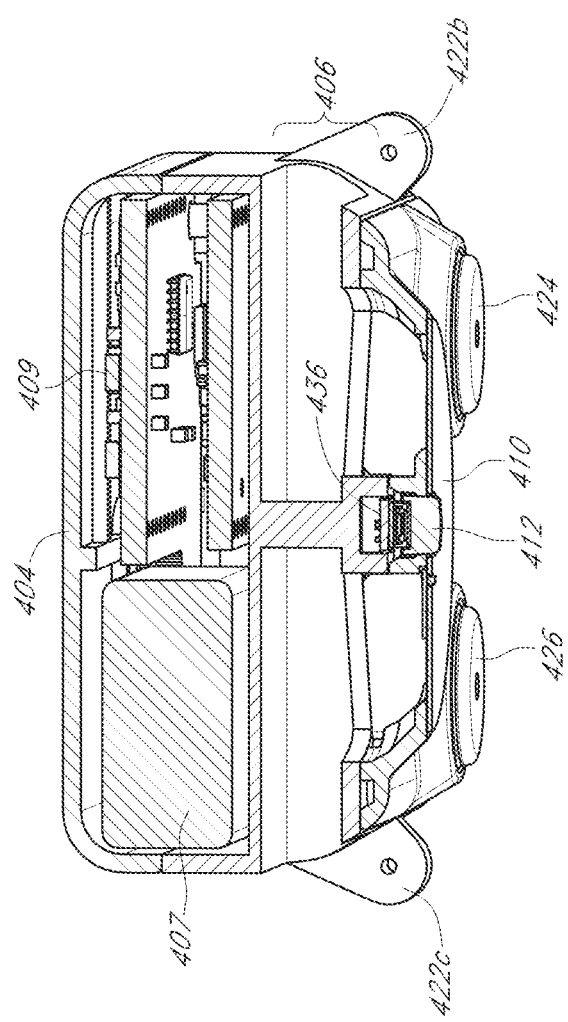
FIG. 43 illustrates a cross-sectional view of a wearable system for detecting an anomalous biologic event.

In any of the embodiments described herein, a wearable system or device for detecting anomalous biologic events may include one or more motion sensors 436 configured to measure a motion of a body portion to which the wearable system is coupled, as shown in FIG. 43. For example, the one or more motion sensors may measure an acceleration in six or nine degrees of freedom. As described elsewhere herein, a wearable system or device for detecting stroke may, in combination with measuring a vasodilation response in response to application of heat, may measure asymmetrical movement or tremors of the right and left limbs. One or more motion sensors may be positioned anywhere on the wearable device. For example, in one embodiment, a motion sensor is positioned in or on the first surface. In another embodiment, a motion sensor is positioned in or on the second surface. In another embodiment, a motion sensor is positioned in between the first and second surfaces. In another embodiment, a motion sensor is positioned on a sidewall of the body of the wearable device. In another embodiment, a motion sensor is positioned adjacent to a vasodilation sensor or temperature sensor of the system, for example concentrically surrounded by the heat source, as shown in FIG. 43.

The heat source of the wearable device or system 400 may be cooled in between heating cycles to ensure a return to baseline or substantially baseline of the vasodilation response of the skin surface in between heating cycles. As such, the heat source may be cooled by an airflow system (e.g., fan), a vacuum or vibrating mechanism configured to displace or pull or move environmental air across the heat source (e.g., solenoid and diaphragm, oscillating piezo element), etc. In one embodiment, as shown in FIGS. 40-43, a wearable system or device for detecting an anomalous biologic event includes first 404 and second 402 surfaces that together define a cavity 406 therebetween to provide airflow between the first 404 and second 402 surfaces. The cavity 406 defined by the first 404 and second 402 surfaces physically separates the heat source 410 from the hardware processor 409 positioned on or within the first surface 404. The hardware processor 409 can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein. The cavity 406 functions to expose the heat source 410 to ambient or environmental or surrounding air to cool the heat source 410 to a temperature that approaches, substantially equals, or equals a temperature of the air in the environment or an ambient temperature. The cavity 406 may be an empty space, an interstitial space, a space that houses one or more components, etc. In some embodiments, cavity 406 formed by the first 404 and second 402 surfaces is open to ambient air or environmental air such that the sidewalls 405 that couple together the first 404 and the second 402 surfaces are opposite one another so that the cavity 406 is open to the environmental air on opposing sides, as shown in FIGS. 40-41. Alternatively, the sidewalls 405 are connected to one another and adjacent to one another so that the cavity is open to the environmental air on adjacent or connected sides.

For example, in some embodiments, the cavity 406 defined by the first 404 and second 402 surfaces has sufficient volume to facilitate cooling of the heat source 410 in between heating cycles. Alternatively, or additionally, the cavity 406 may further include an airflow system, vacuum or vibrating mechanism, or other airflow mechanism to promote airflow through the cavity 406 to reduce a temperature or cool the heat source 410.

In some embodiments of a wearable system or device, the device includes a port 420 for electrically coupling the device to a power source, for example to charge a battery 407 in the device. Additionally, or alternatively, port 420 electrically couples the wearable device to an external or remote computing device (e.g., laptop, desktop, server, workstation, etc.) to download data from the device or upload system parameters or install updates to the wearable device. The wearable device may further include one or more user input elements 418 to power on and off the device; to input user specific reactions, features, or characteristics, to customize an interface or functionality of the user device, etc.

In some embodiments, as shown in FIG. 45, a wearable system for detecting an anomalous biologic event includes a first system or device 400 positioned on a left limb of a user and a second system or device 500 positioned on a right limb of the user. The first and second devices 400, 500 may measure similar parameters or features so that the parameters or features are comparable over time and/or on an event-by-event basis to detect asymmetrical biologic responses. For example, a hardware processor as part of the system or communicatively coupled to the devices (e.g., laptop 450 or mobile computing device 46) may be configured to compare right side blood volume signals (e.g., in response to an application of heat) to left side blood volume signals (e.g., in response to application of heat) to determine whether the anomalous biologic event has occurred. The right and left side blood volume signals may be compared to a baseline right and left side blood volume signals, respectively, to account for any asymmetrical baseline differences that may exist between the left and right sides. Further, a method performed by the hardware processor may include synchronizing the signals received from the left limb and the right limb in time; and comparing the synchronized signals from the left limb and the right limb to determine whether the anomalous biologic event occurred.

Figure 44:
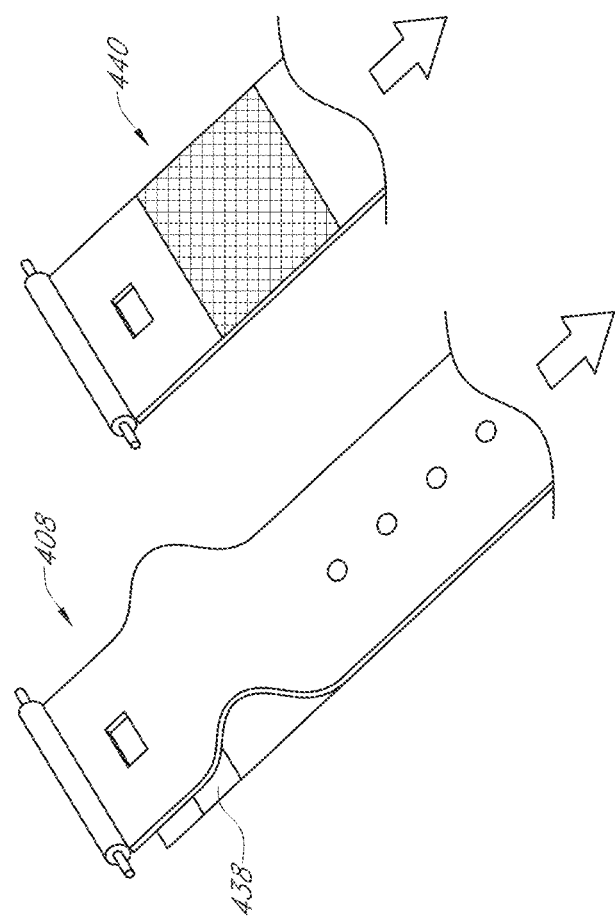
FIG. 44 illustrates one embodiment of a tensionable band for coupling a wearable system to a skin surface.

Turning now to FIG. 44, which shows a coupling element 408, configured to couple a wearable system for detecting an anomalous event to a limb or body portion of a user. For example, the coupling element may be a tensionable band for coupling a detection system or device to a limb or body portion of a user. The tensionable band is formed of or comprises a stretchable material (e.g., silicone, rubber, Lycra, Spandex, Elastane, neoprene, leather, fabric, etc.). Alternatively, a portion or section 440 of the coupling element may be stretchable, such that the stretchable portion or section 400 can be extended or retracted by applying varying amounts of tension to the coupling element. Accordingly, the coupling element may be adjustable so that the coupling element fits a variety of body portion shapes and sizes. For example, the coupling element may have an adjustable circumference. The coupling element may further include a visual indicator 438 to indicate when one or more of: the heating element, the skin temperature sensor, the blood volume sensor, or a combination thereof is sufficiently coupled to the skin surface to enable accurate sensor readings.

Figure 37:
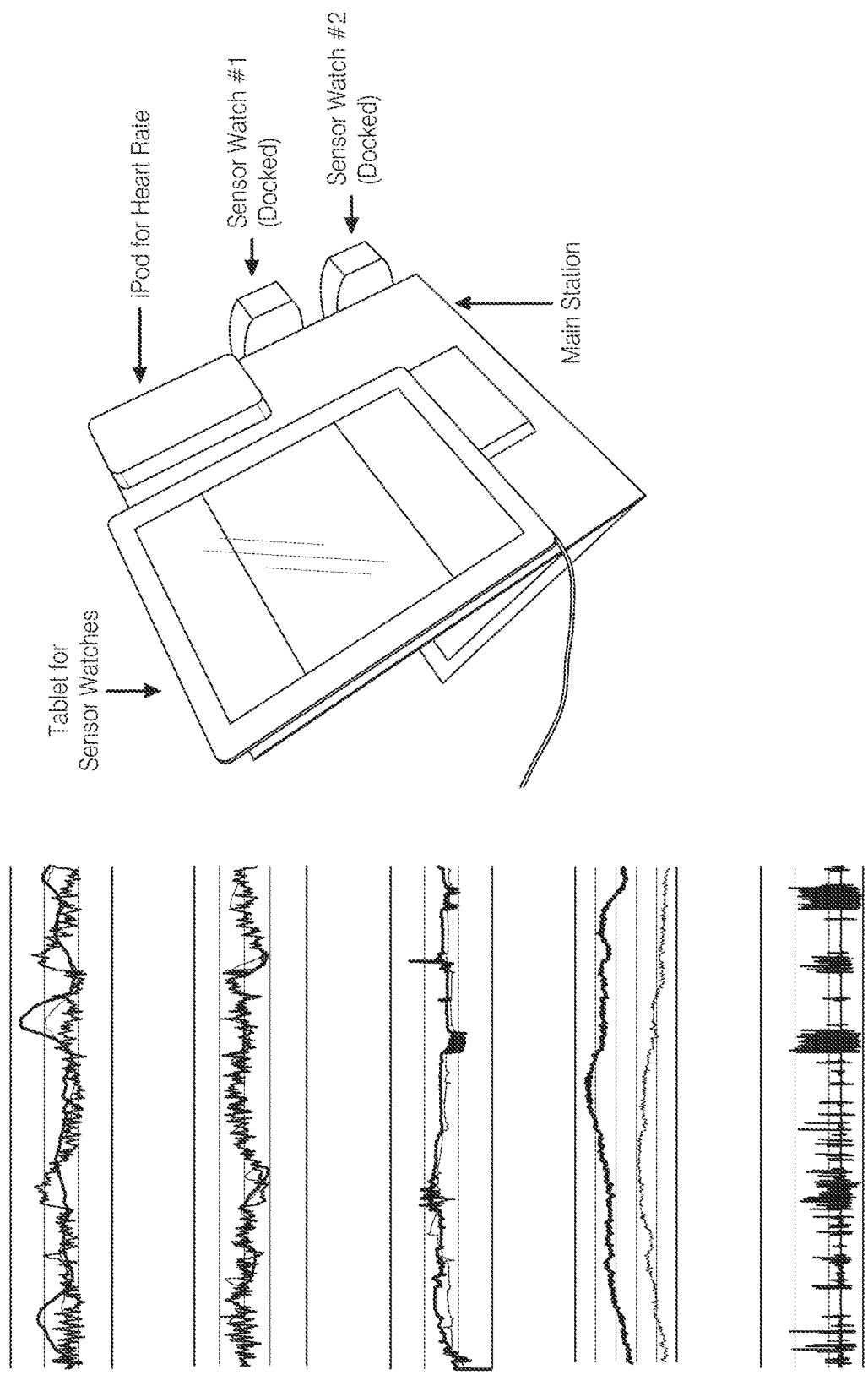
FIG. 37 illustrates an embodiment of a system for detecting stroke.

Referring to FIG. 37, a system for detecting stroke may include collect data from one or more sources, for example a contact-based source, a non-contact-based source, and a source that stimulates a response and then measures the response output. As shown in FIG. 37, the system may include a main station or docking station and/or measurement station for one or more measurement devices. For example, a heart rate monitor, devices for measuring asymmetrical responses or effects (e.g., watches worn on each wrist), etc. may be included in the system. The system may be portable such that is may be positioned in a mobile stroke detection unit for rapid detection of stroke or positionable in homes of high-risk patients.

Figure 8:
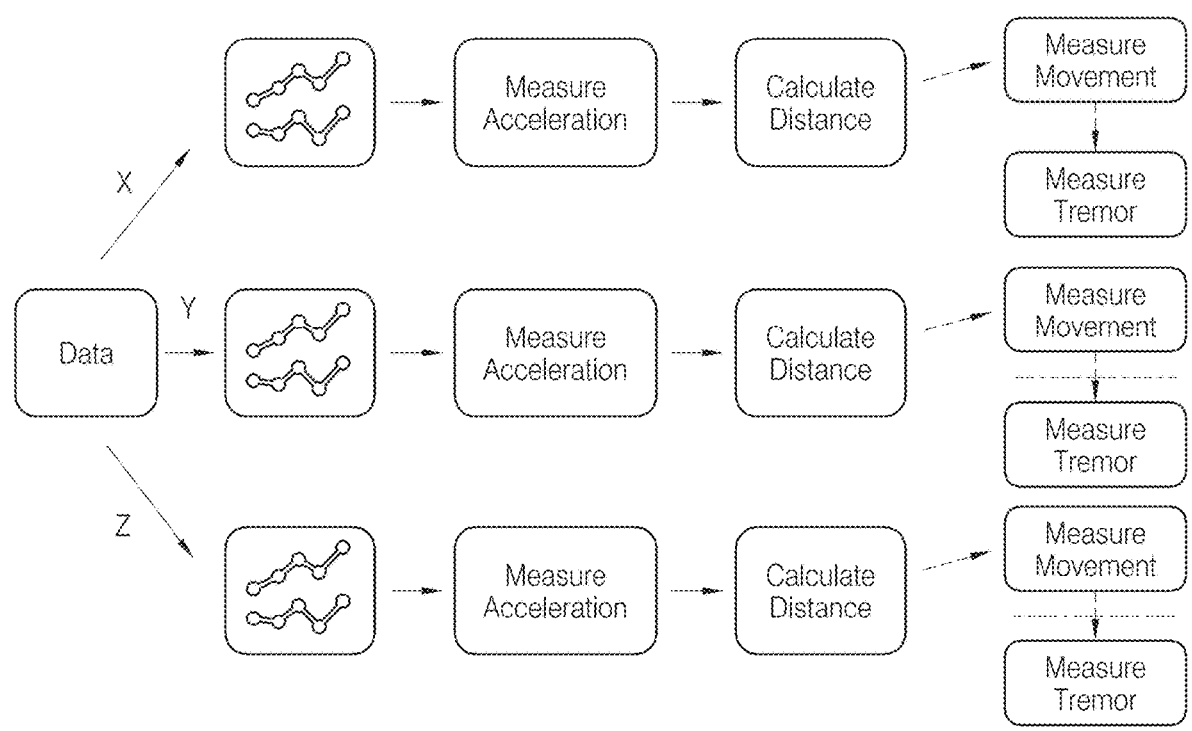
FIG. 8 shows one embodiment of a workflow for calculating tremor measurements from captured acceleration data.
Figure 9:
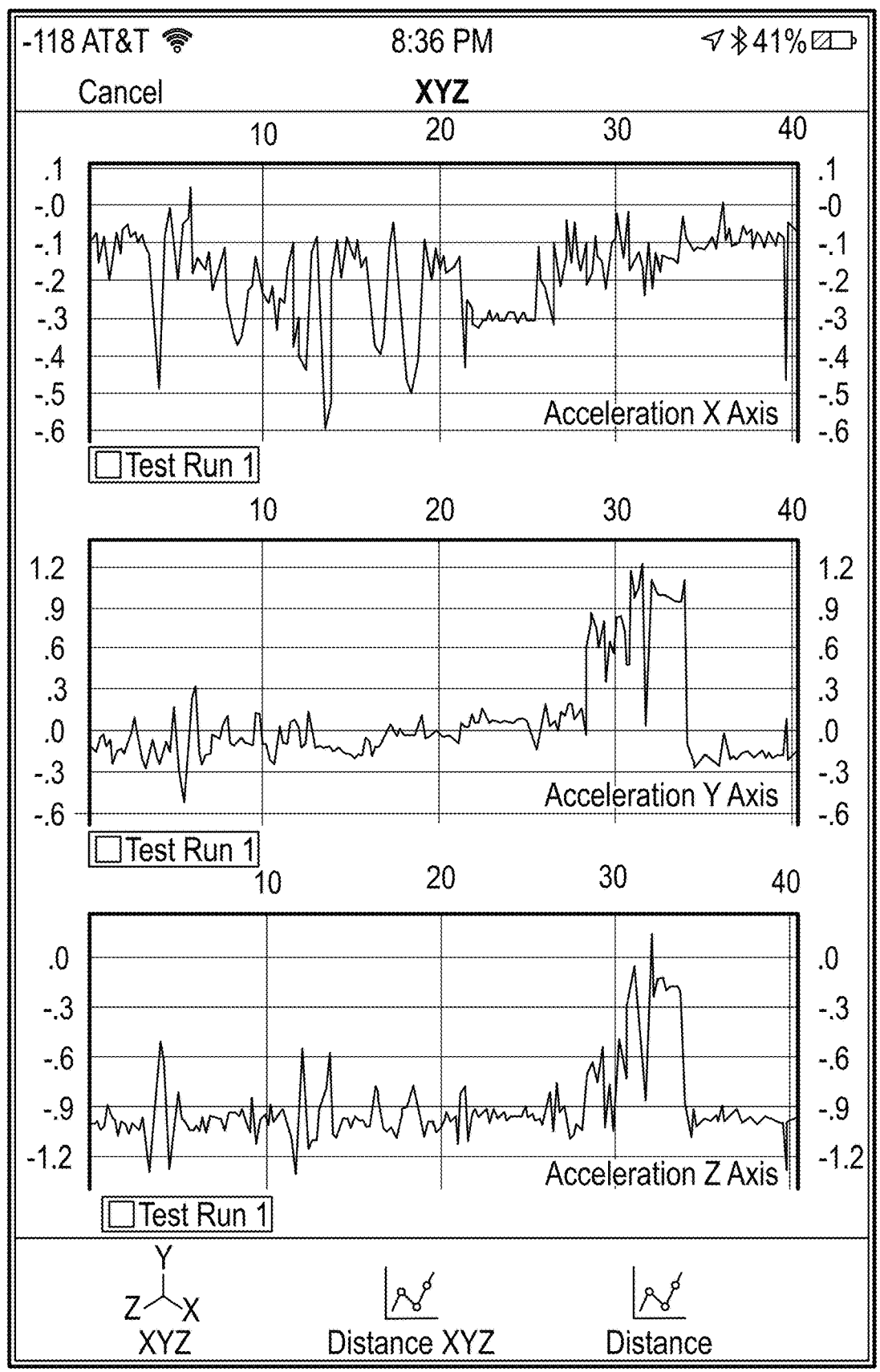
FIG. 9 shows a graphical representation of acceleration data analyzed using an application on a computing device.
Figure 10:
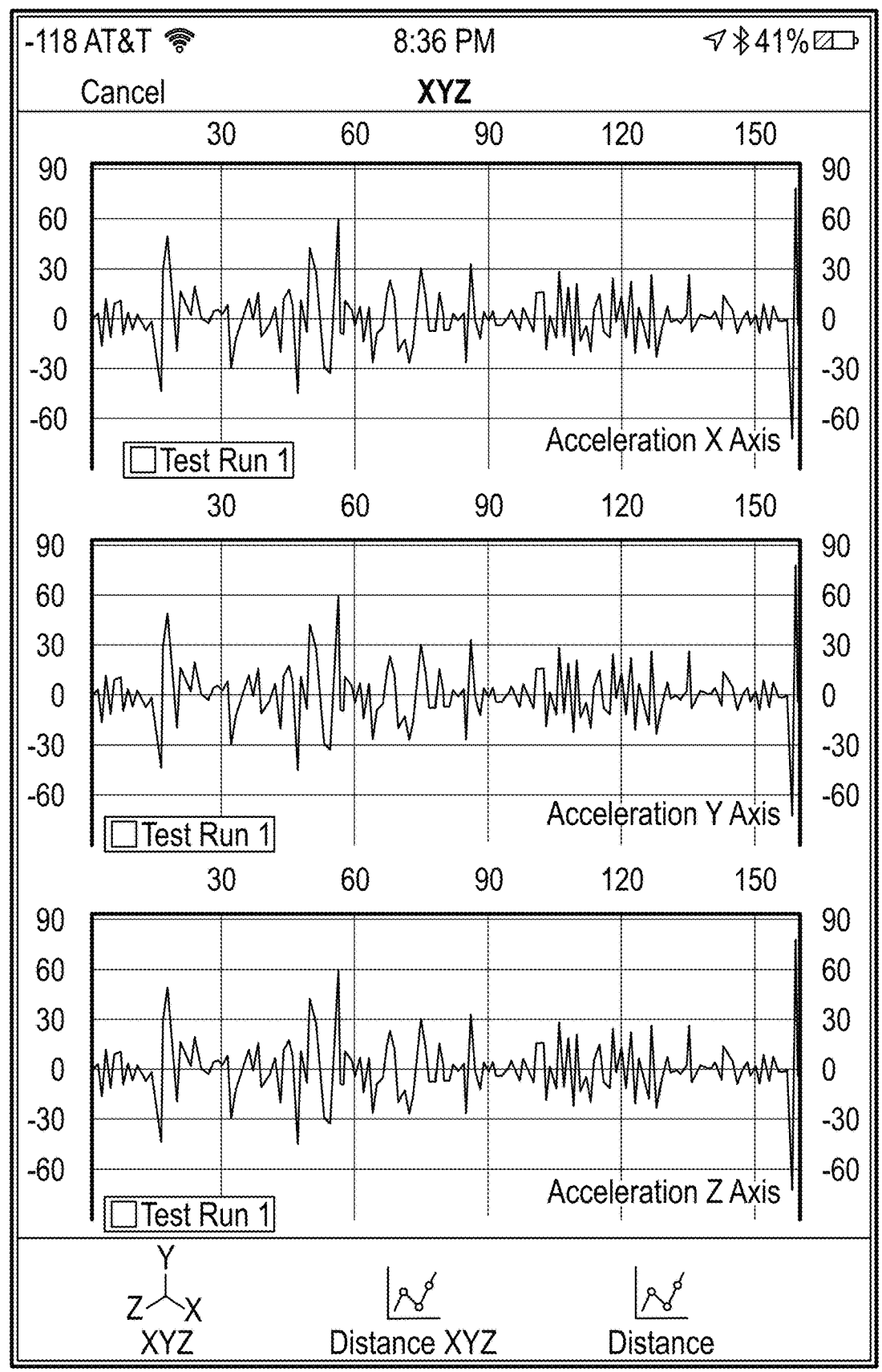
FIG. 10 shows a graphical representation of distance data analyzed using an application on a computing device.
Figure 11:
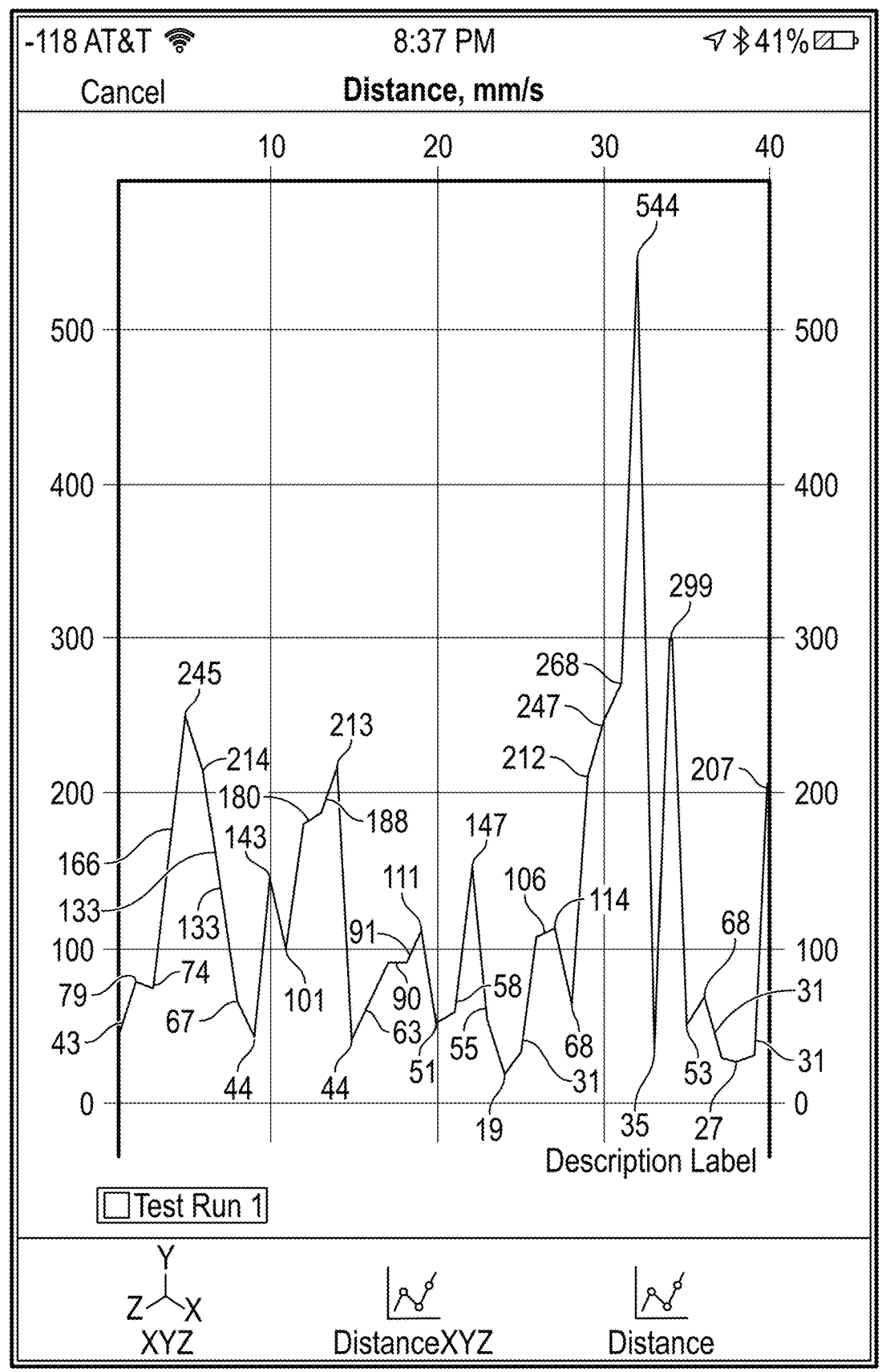
FIG. 11 shows a graphical representation of movement data analyzed using an application on a computing device.
Figure 12:
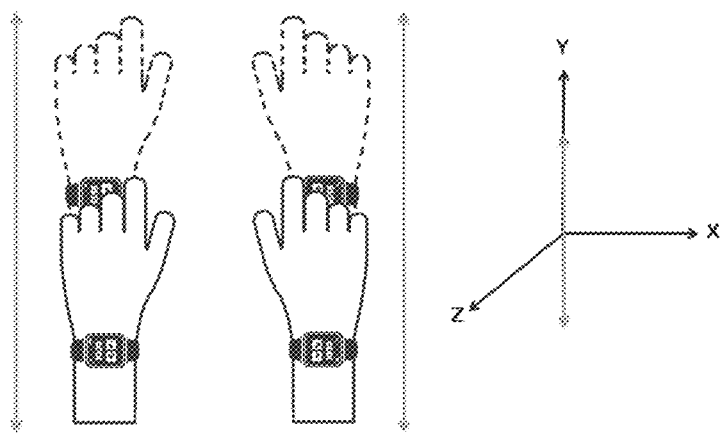
FIG. 12 illustrates one embodiment of a system for detecting symmetrical limb movement.
Figure 13:
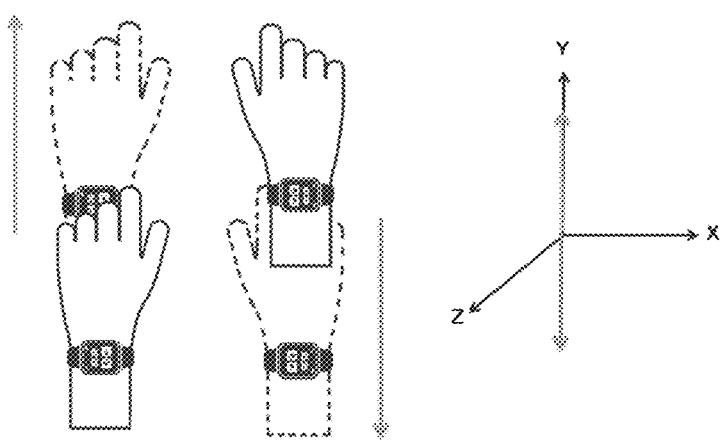
FIG. 13 illustrates one embodiment of a system for detecting asymmetrical limb movement.
Figure 14:
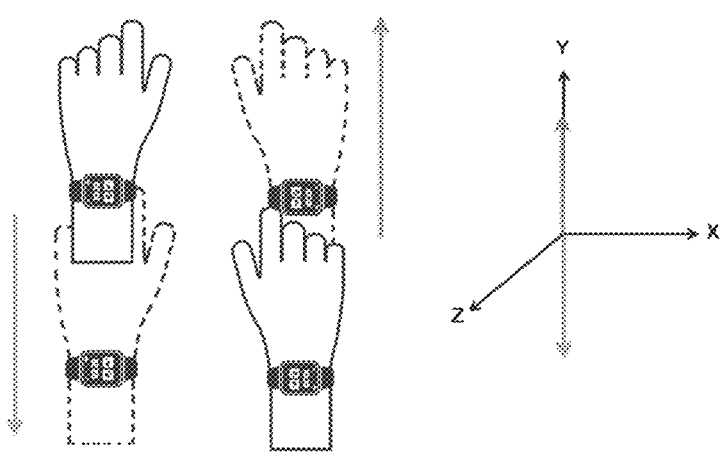
FIG. 14 illustrates another embodiment of a system for detecting asymmetrical limb movement.
Figure 15:
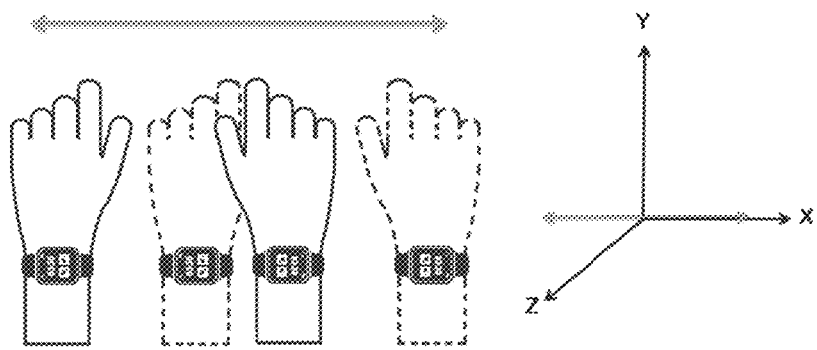
FIG. 15 illustrates another embodiment of a system for detecting symmetrical limb movement.
Figure 16:
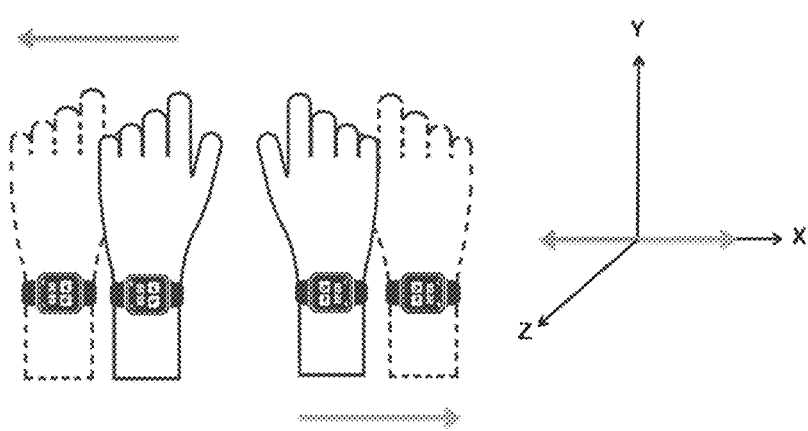
FIG. 16 illustrates another embodiment of a system for detecting asymmetrical limb movement.
Figure 17:
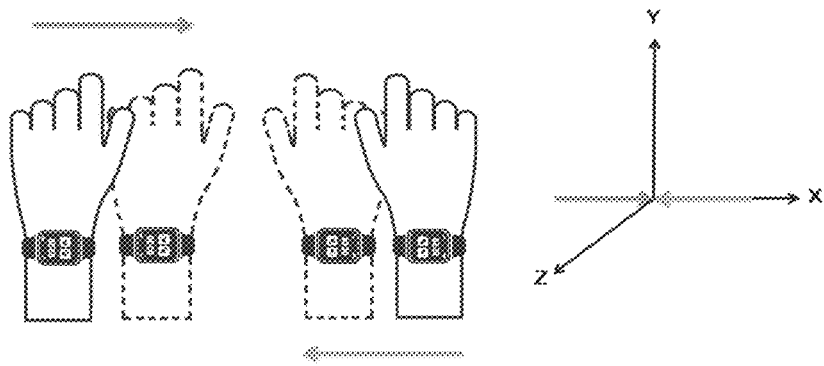
FIG. 17 illustrates another embodiment of a system for detecting asymmetrical limb movement.
Figure 18:
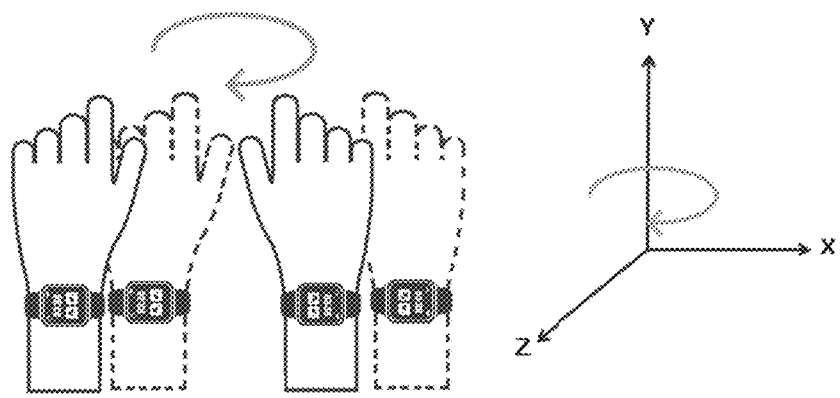
FIG. 18 illustrates another embodiment of a system for detecting symmetrical limb movement.
Figure 19:
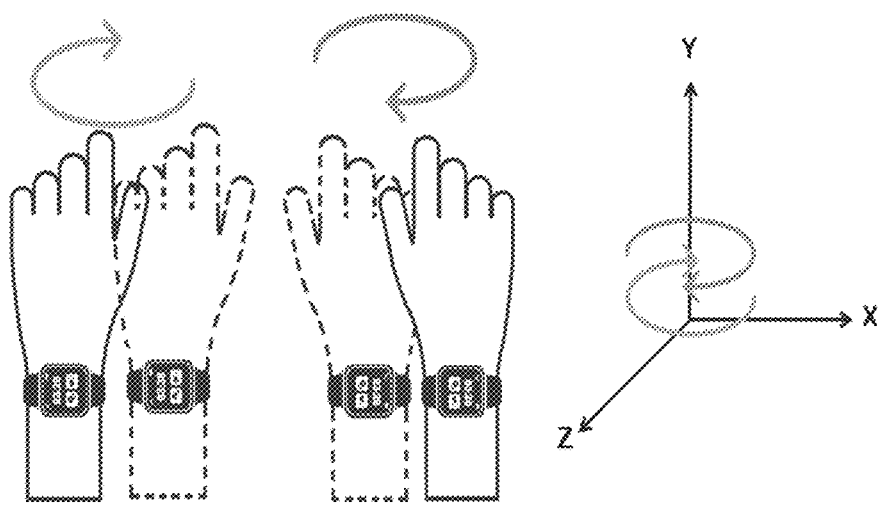
FIG. 19 illustrates another embodiment of a system for detecting asymmetrical limb movement.
Figure 20:
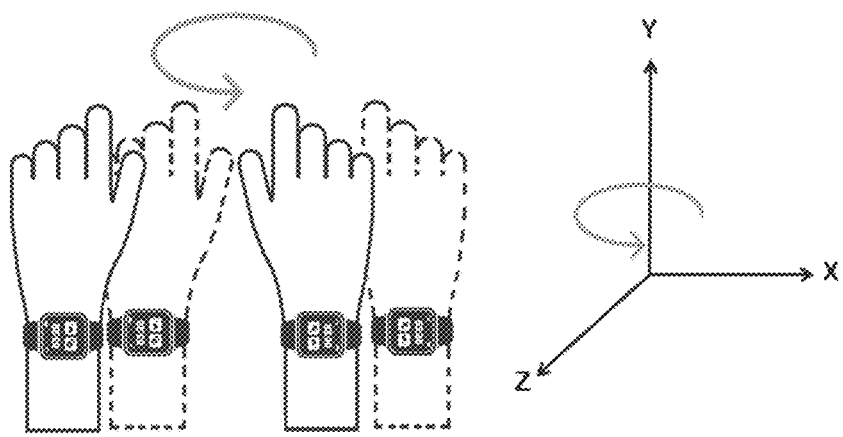
FIG. 20 illustrates another embodiment of a system for detecting symmetrical limb movement.
Figure 21:
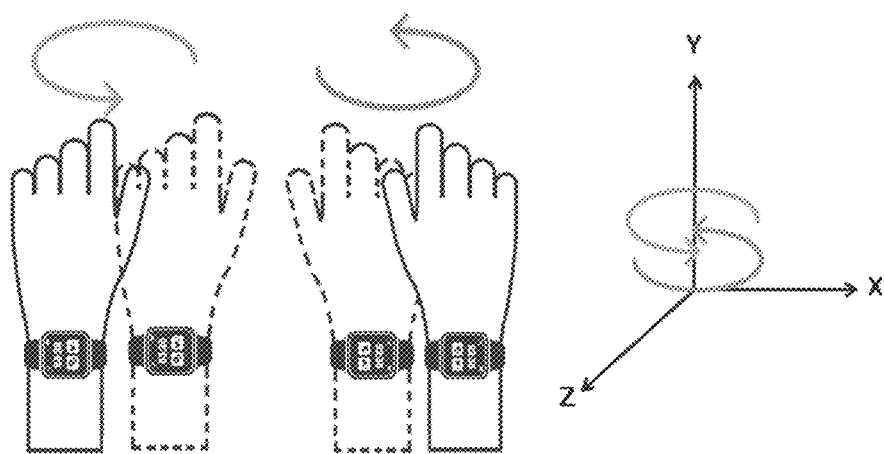
FIG. 21 illustrates another embodiment of a system for detecting asymmetrical limb movement.
Figure 22:
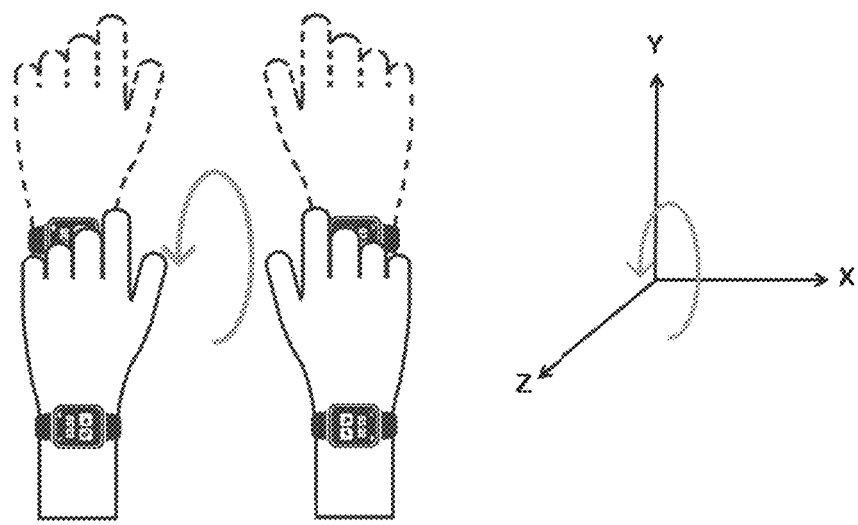
FIG. 22 illustrates another embodiment of a system for detecting symmetrical limb movement.
Figure 23:
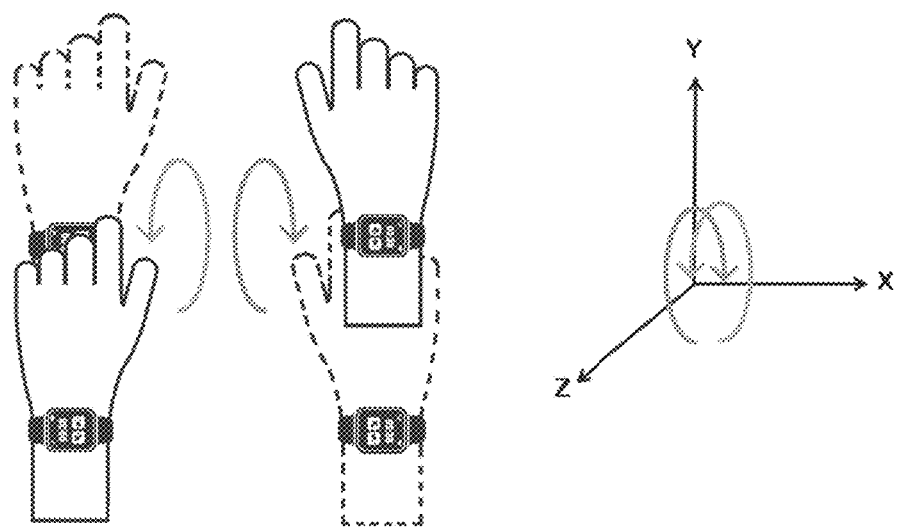
FIG. 23 illustrates another embodiment of a system for detecting asymmetrical limb movement.
Figure 24:
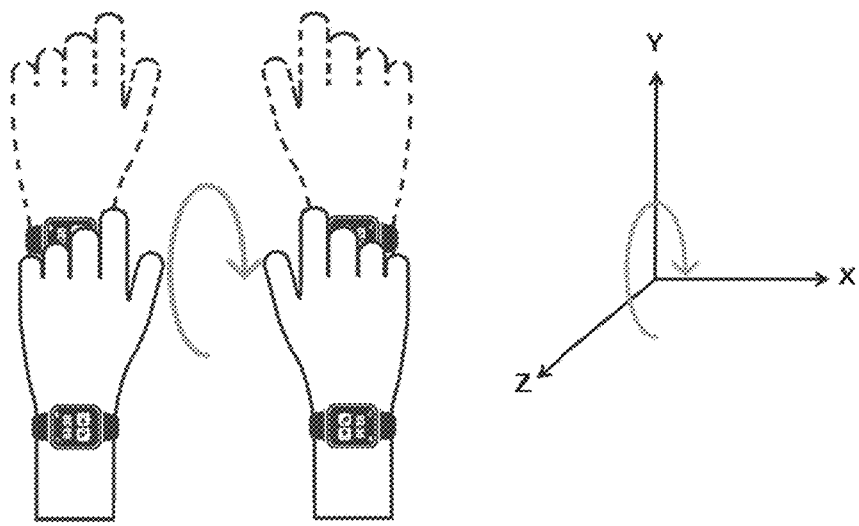
FIG. 24 illustrates another embodiment of a system for detecting symmetrical limb movement.
Figure 25:
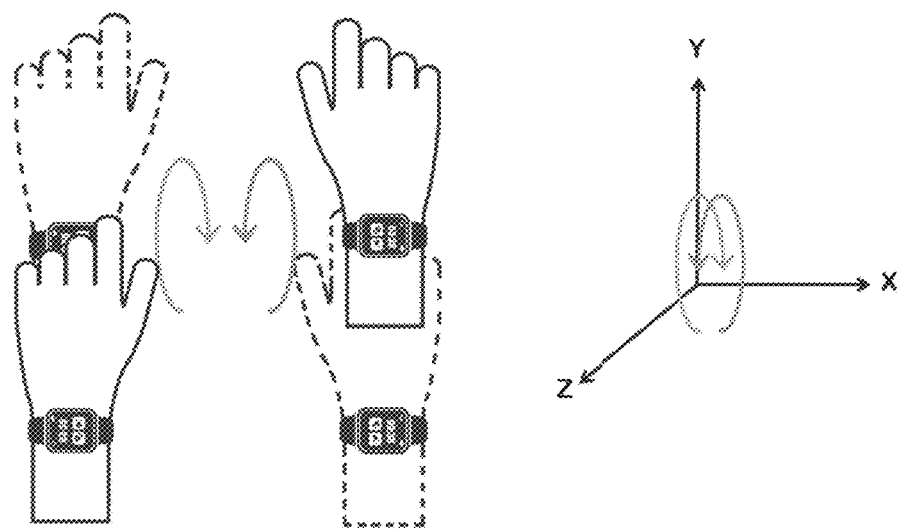
FIG. 25 illustrates another embodiment of a system for detecting asymmetrical limb movement.

For example, as shown in FIG. 8, a method of detecting tremors (i.e., asymmetrical wrist movement) includes: measuring an acceleration in x, y, and/or z planes of two limbs (e.g., two arms or two legs) of an individual; measuring a distance in x, y, and/or z planes of the two limb of the individual; and calculating a movement of each limb, relative to the other limb, of the individual. In some embodiments, symmetrical movement is indicative of healthy, non-stroke movement, and asymmetrical movement is indicative of a tremor or a stroke event. Exemplary acceleration data (XYZ) is shown in FIG. 9; distance data (XYZ) in FIG. 10; and distance (MM/S; movement) data in FIG. 11. In some embodiments, a specific pattern of time series movements is unique to an individual and classified as a tremor based on data collected over time. For example, tremor data may be collected for a number of hours, including wake cycles and sleep cycles. The statistical modeling of a tremor then becomes a signature for each patient. This signature also allows a baseline to be set for each patient. Again, this baseline behavior may be unique to an individual, and even to the 'awake' and 'sleep cycles' of the individual.

Figure 26:
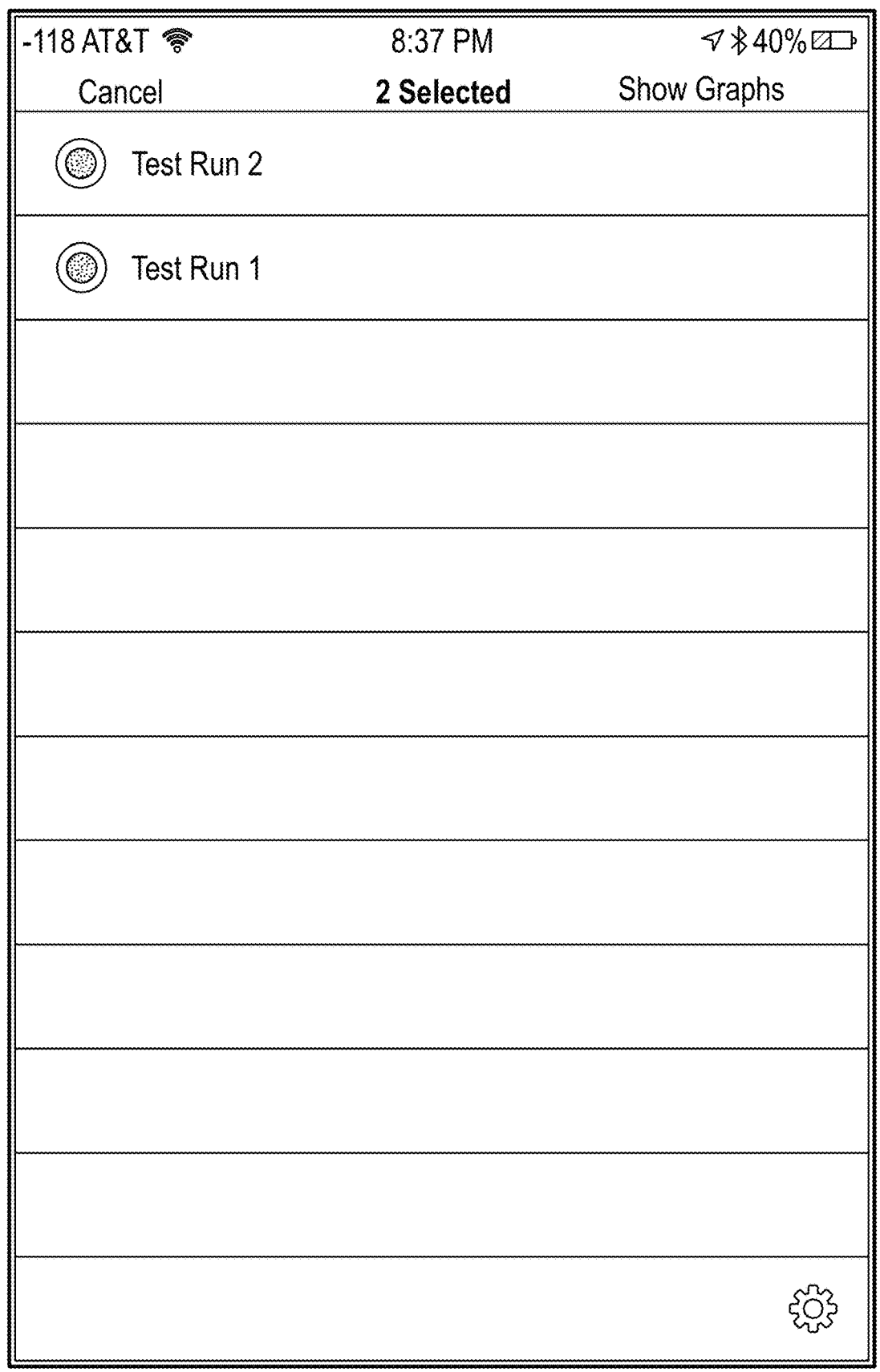
FIG. 26 shows one embodiment of an application on a computing device for comparing two sets of data from two limbs.
Figure 27:
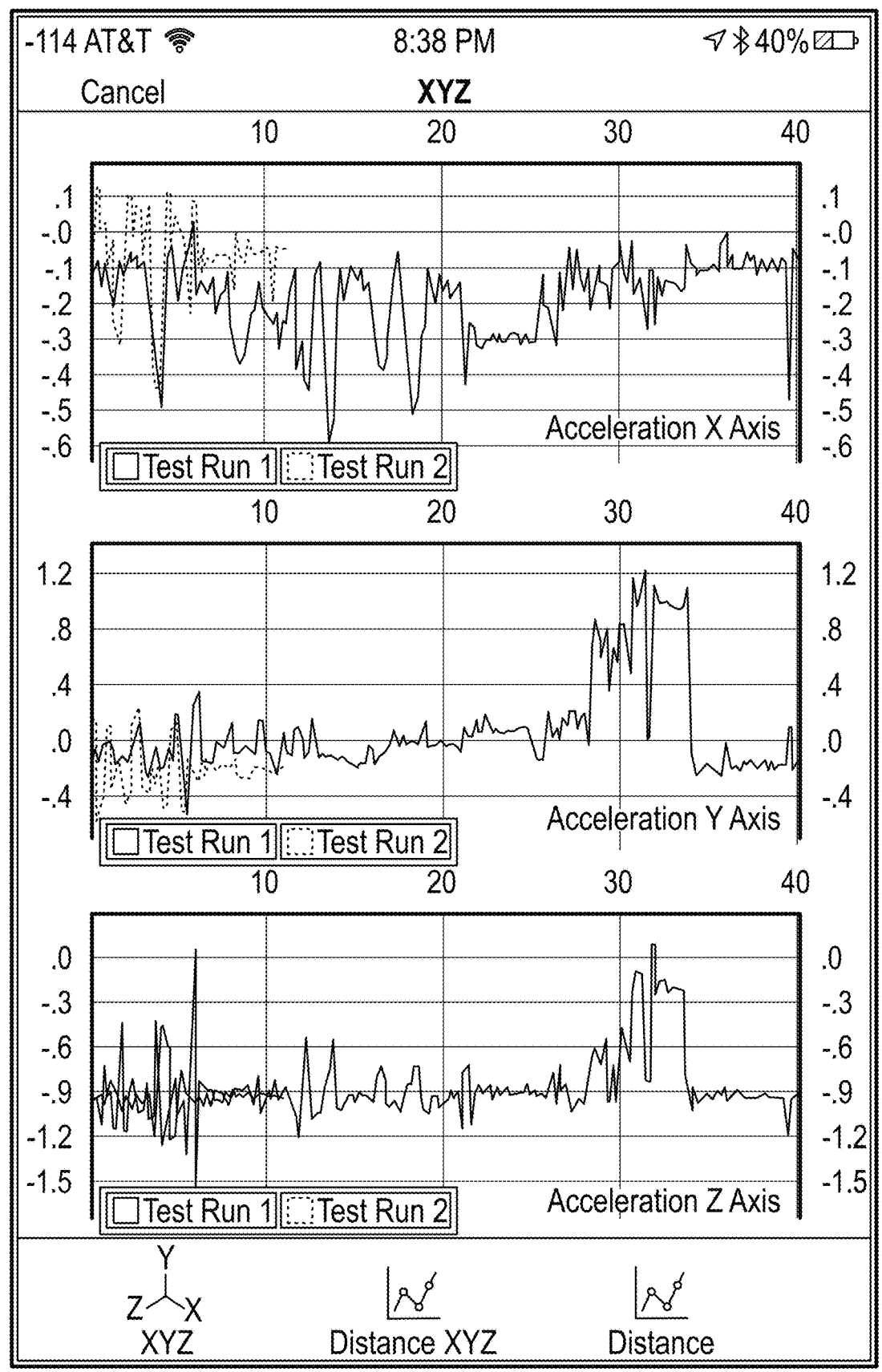
FIG. 27 shows a graphical representation of acceleration data from two wrists.
Figure 28:
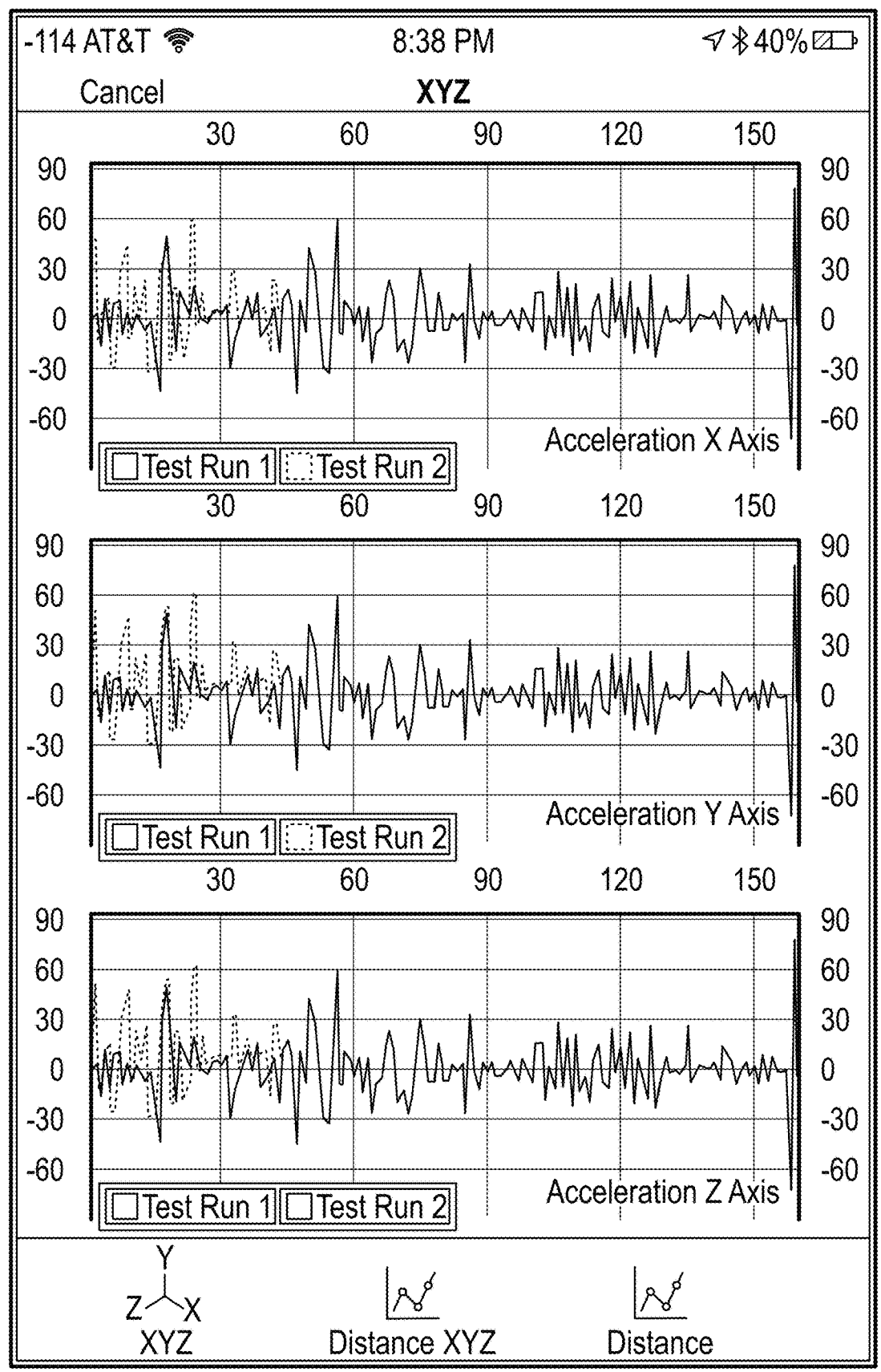
FIG. 28 shows a graphical representation of distance data from two wrists.
Figure 29:
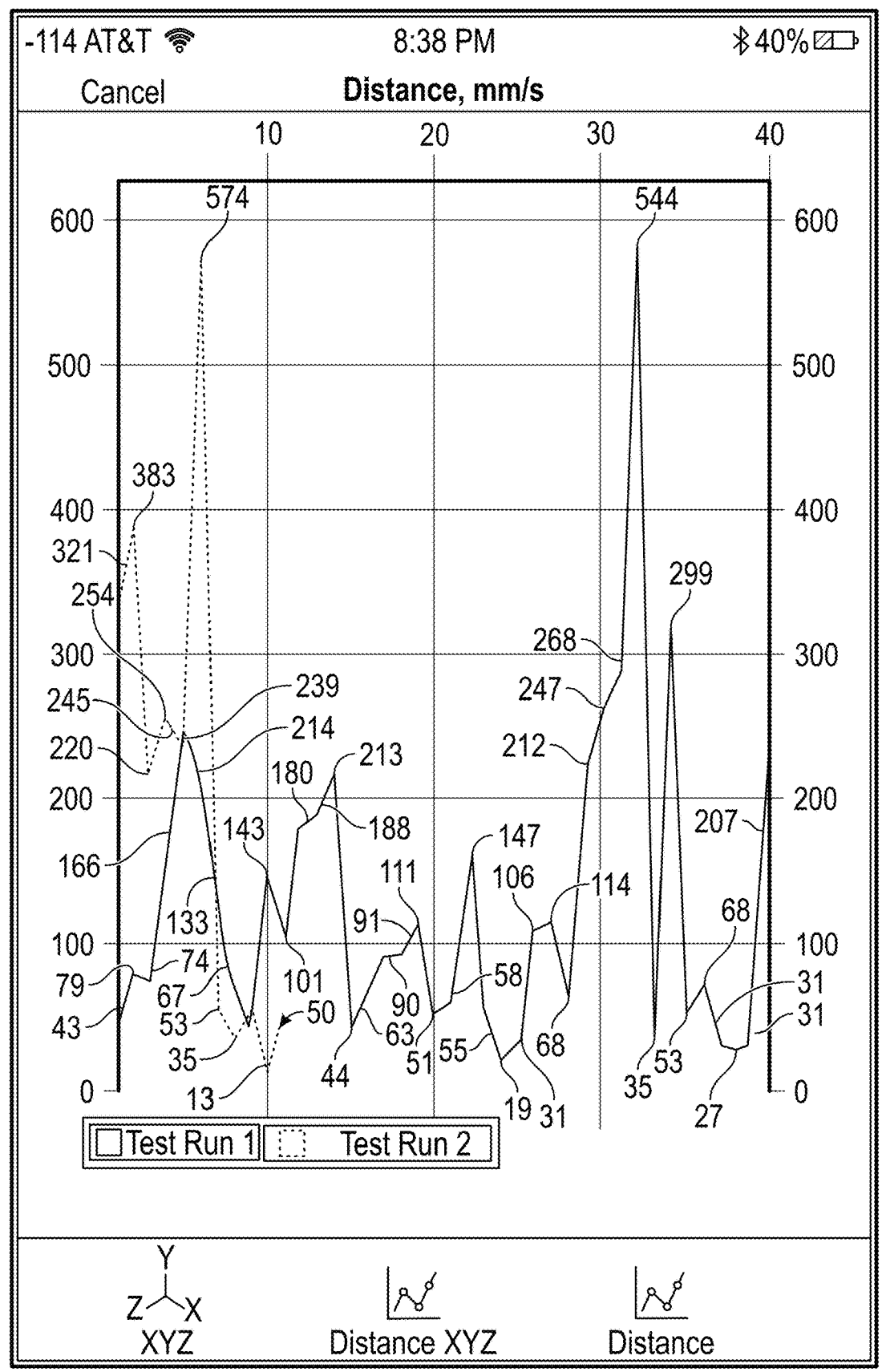
FIG. 29 shows a graphical representation of movement data from two wrists.
Figure 30:
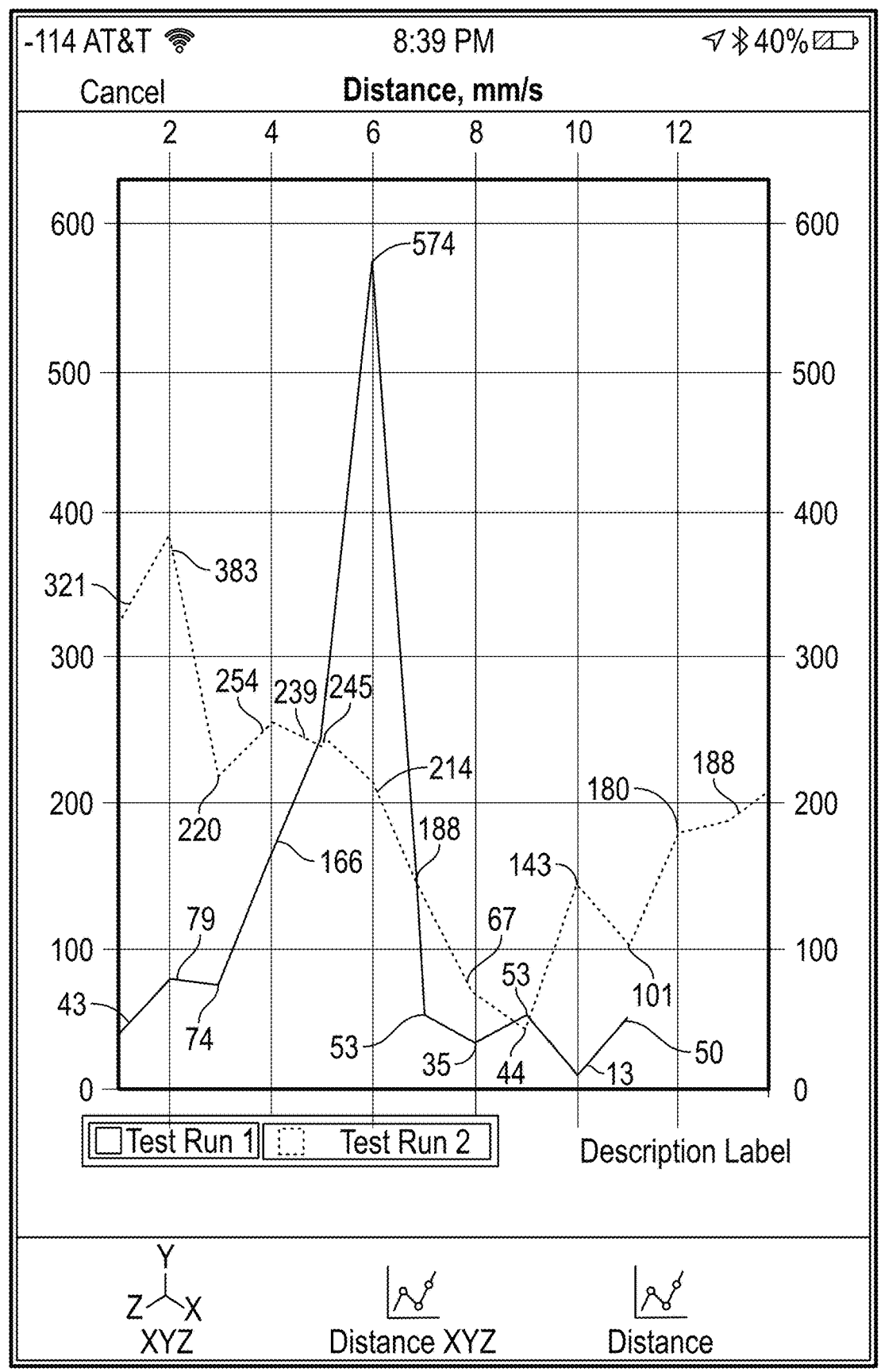
FIG. 30 shows a graphical representation of movement data from two wrists, while using a zoom feature of an application on a computing device.
Figure 31:
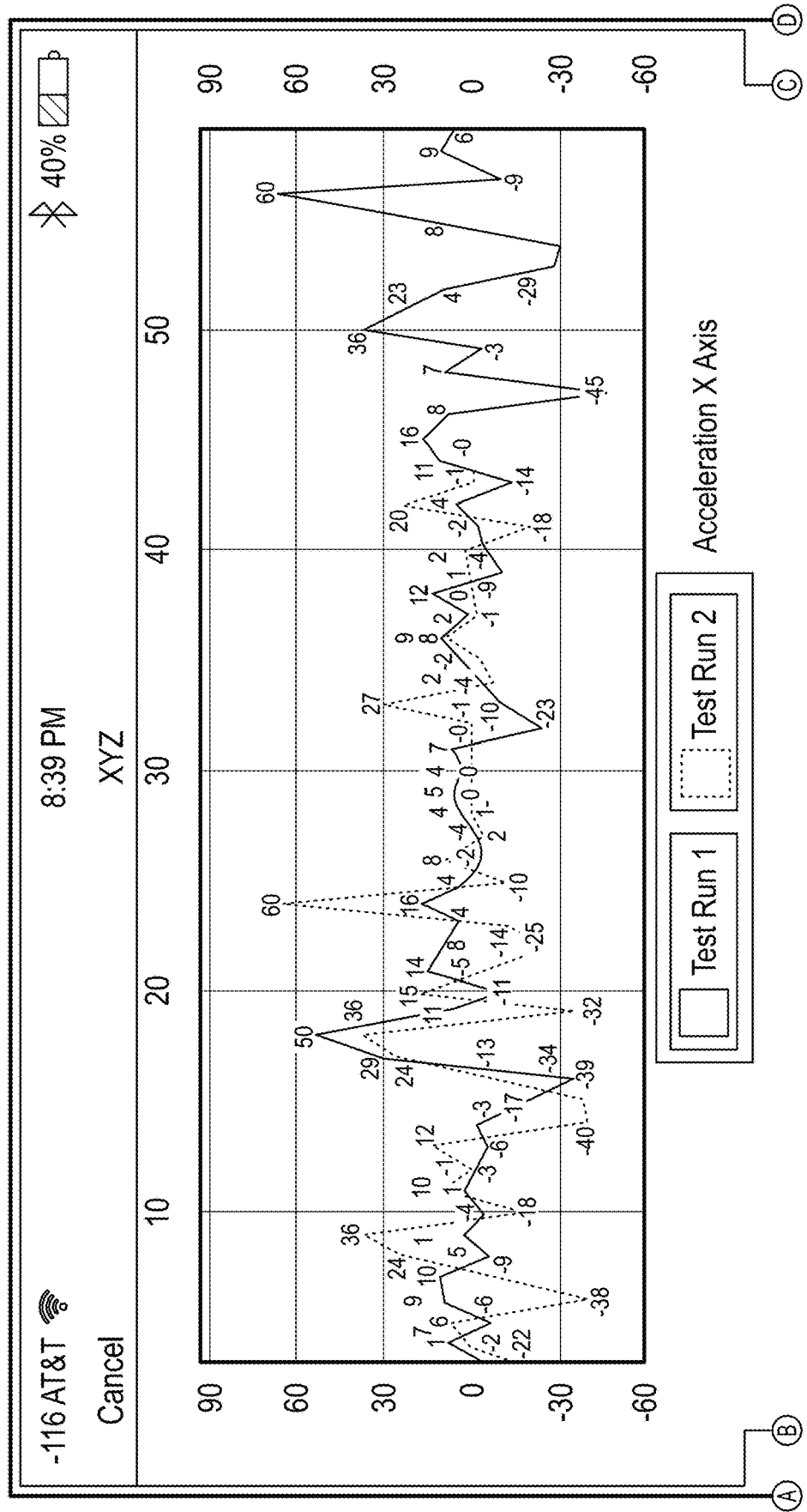
FIG. 31 shows a graphical representation of distance data from two wrists.
Figure 31:
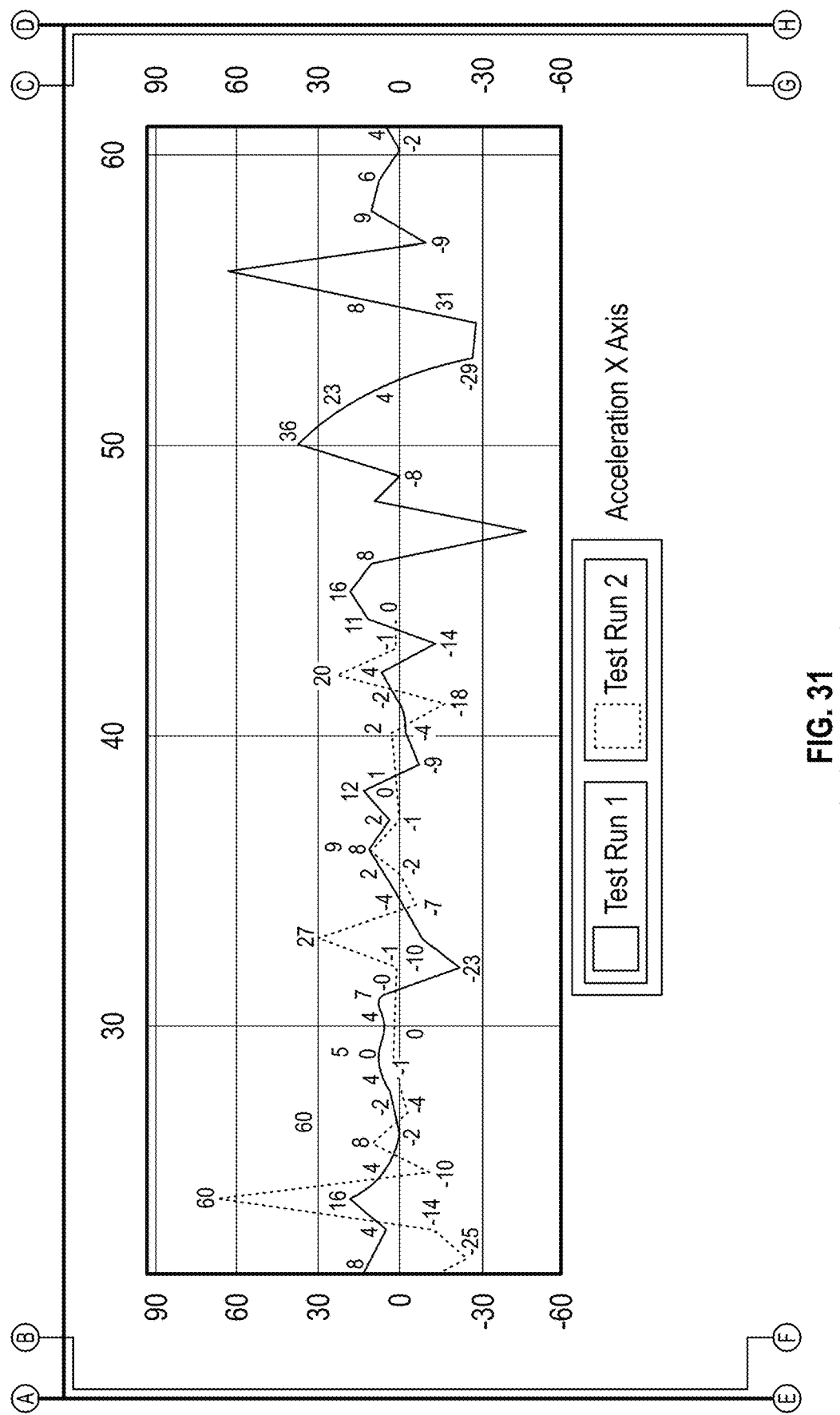
Figure 31:
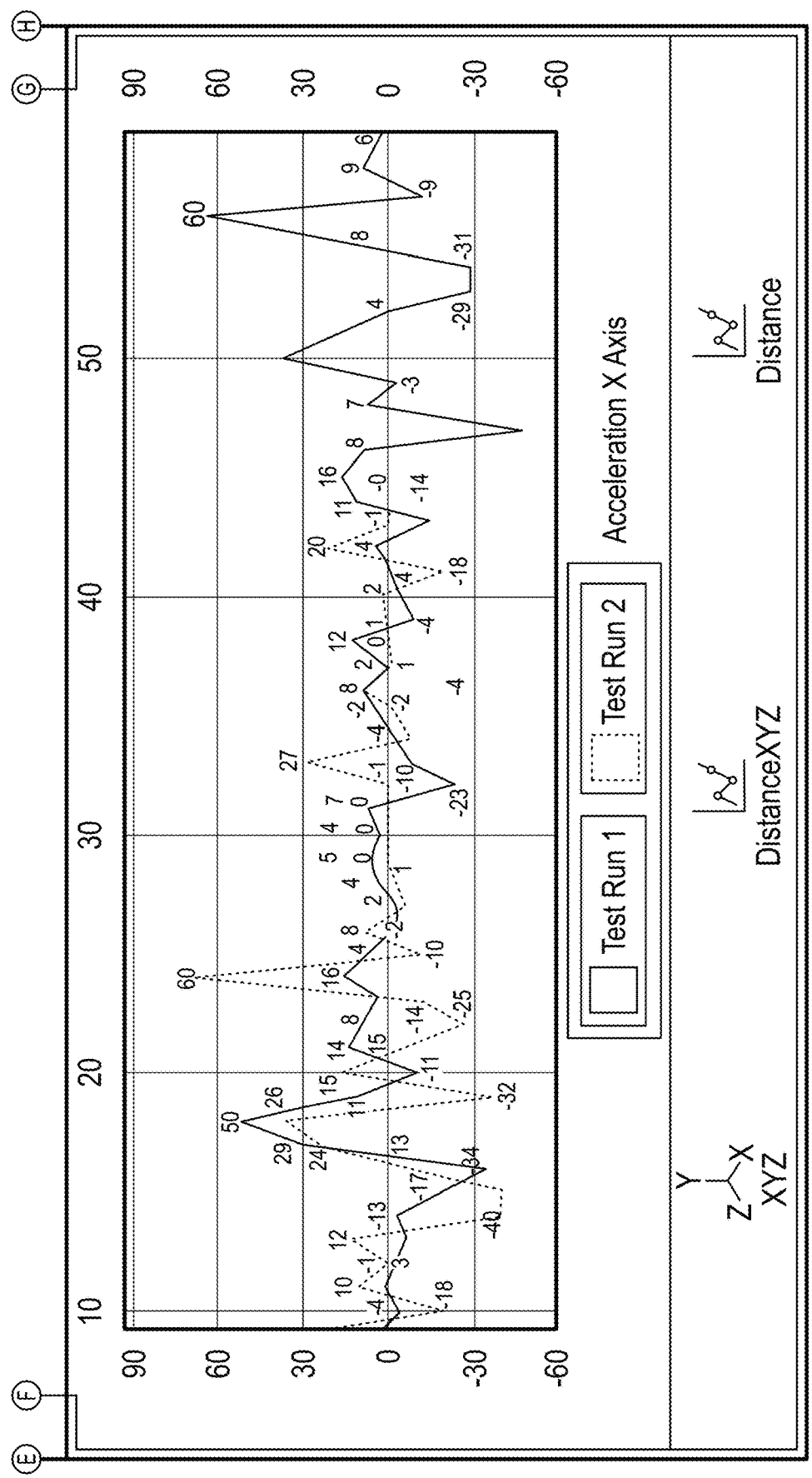
Figure 32:
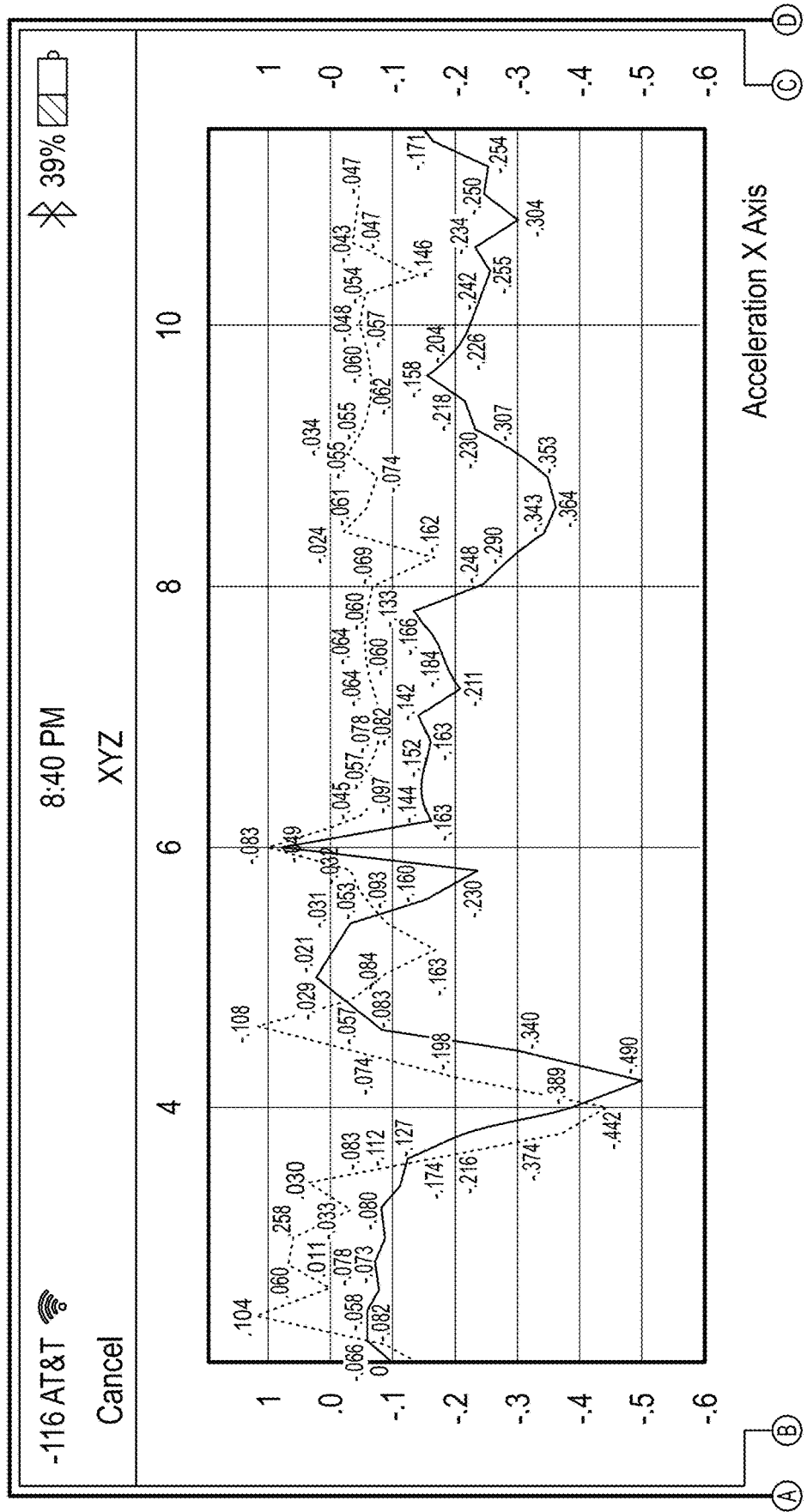
FIG. 32 shows a graphical representation of acceleration data from two wrists.
Figure 32:
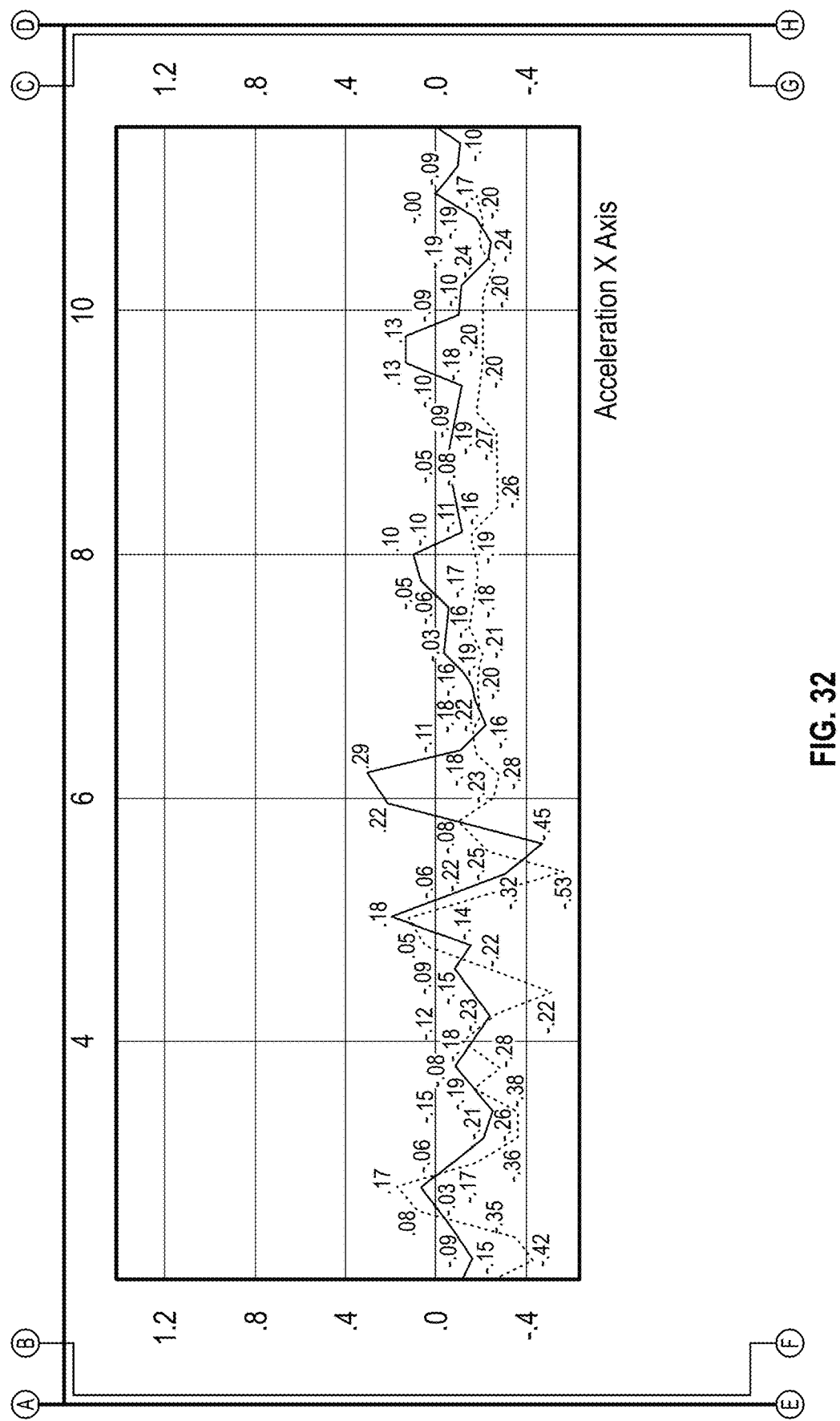
Figure 32:
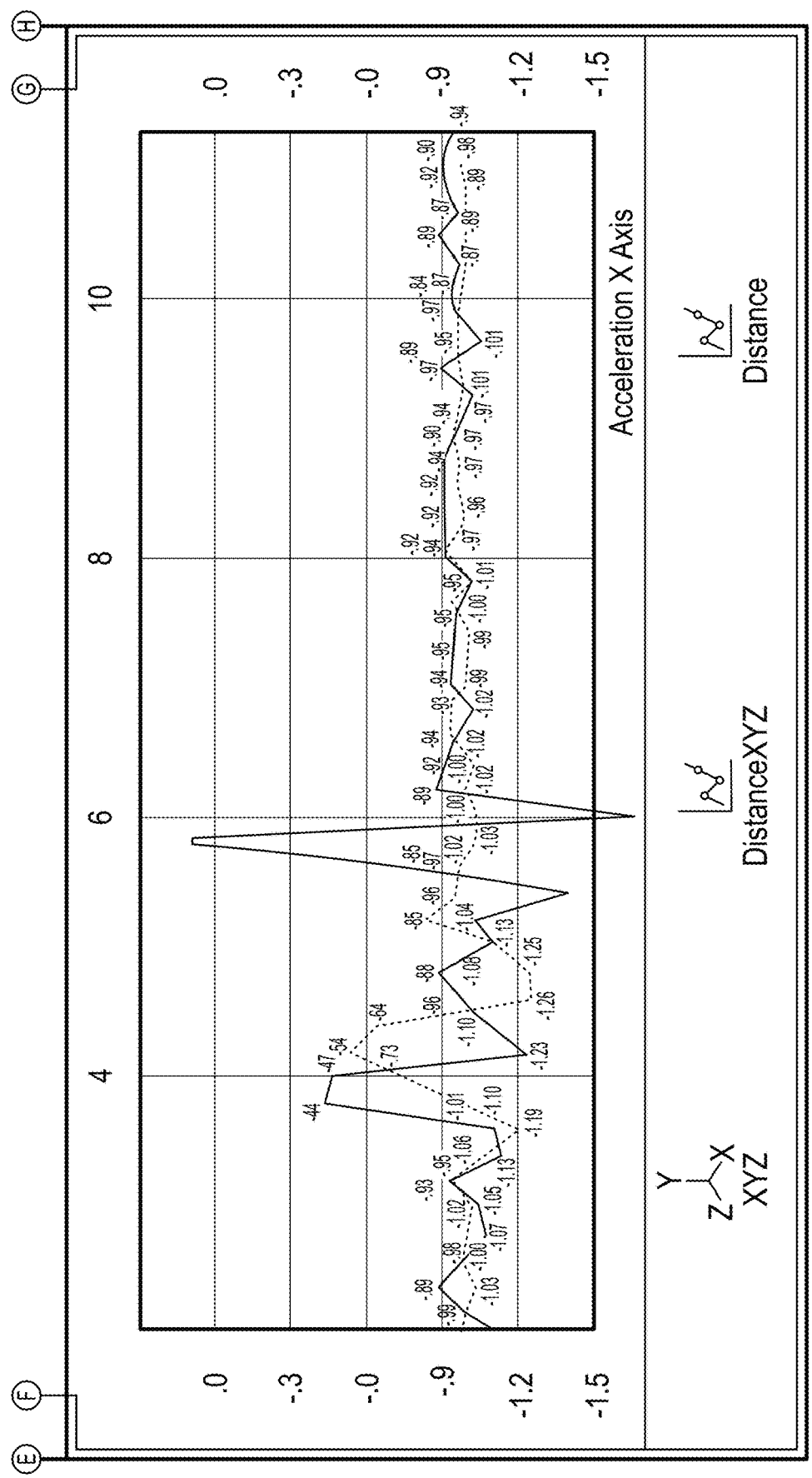

As shown in FIG. 26, an application downloaded and/or stored on a hardware component of a stroke detection system or a computing device collates and analyzes acceleration and distance data sensed by a sensor, for example an accelerometer. The comparison of two data sets (i.e., Test Run 1 and Test Run 2) derived from devices located on the two limbs (e.g., wrists) of the user is shown in FIG. 26. For example, an application on a computing device may be configured to compare two acceleration data sets (FIGS. 27, 32); two distance data sets (FIGS. 28, 31); and two movement data sets (FIGS. 29, 30) from devices positioned on two wrists of a user. As shown in FIGS. 29-30, an application on a computing device may further include a zoom feature, for example, for viewing a subset of the total data collected during a period of time (e.g., overnight, during a tremor instance, etc.).

In some embodiments of a device for detecting tremors or asymmetrical motion, the device may include a feedback mechanism (e.g., visual, haptic, or audio) when a threshold has been reached or surpassed or various comparison criteria have been met, for example when a current movement pattern matches a previously identified tremor pattern for the individual. In some embodiments, a mobile computing device communicatively coupled to a movement sensor or wearable device generates a vibration signal in the wearable device, sensor, and/or computing device if the comparison between the two signals exceeds a predefined threshold.

To determine which embodiments would be best for stroke detection, several factors may be considered: alert 911 capability; passive monitoring; detection when patient is alone; and detection when patient is sleeping. Additional factors may include, but not be limited to: fully mobile; patient specific algorithm; active patient engagement after a passive alert; detection for the cognitively impaired patient; detection for prior stroke patient; detection of all strokes including posterior; diagnose type of stroke; passive monitor that wakes the patient up; and commence stroke treatment. For example, if a possible stroke event is detected, a wearable system may initiate a tactile, auditory, and/or visual alert to determine whether the user is conscious, unconscious, experiencing other stroke symptoms, etc. If the patient does not respond in a predetermined time window, a caregiver, emergency services, physician, etc. may be alerted to the stroke event. The wearable system can be linked to a clinician computing system. The alert can be transmitted directly to the clinician computing system that may prompt a telemedicine assessments. The clinician may work up an NIH Stroke Score assessment in response to the alert and/or data received from the wearable system. In some instances, the wearable system can by itself or in conjunction with a personal computing system enable self-assessment by walking the person and/or available witnesses through a FAST (Facial drooping, Arm weakness, Speech difficulties and Time) assessment.

In some instances, the wearable system can transmit a signal to the user's home automation system or to at least one electronically enabled door lock to unlock at least one door and/or disable the user's home alarm system in response to an alert for the stroke event. The wearable system can also initiate transmission of a floor plan access pathway leading from an access point of entry to the location of the patient, in the home or facility where the user has had indicium of a potential stroke. The location of the patient can be determined based on a local area network or differential GPS. In some embodiments, a stroke detection device or system may trigger an audible alarm to alert a patient or caretaker, for example while sleeping, that a stroke event has occurred. The audible alarm can also enable emergency services to locate patient when they enter home. All of these measures can help to reduce the time it takes for the emergency services or caregivers to reach the patient.

The home automation system can also include smart displays and smart speakers. These smart displays and speakers can be used to convey information to emergency medical response personnel, such as the identification of which medications the patient should be taking and, if available, information about whether they are compliant with prescribed regimens. Information such as the identity of physicians, medical history, allergies, and the existence of medical care power of attorney or advance directives associated with the patient may also be conveyed.

Furthermore, when alerting emergency services or physicians, data including medical history may be transmitted directly to emergency services or physician computing systems, either directly from the wearable system or from a remote memory, initiated by a signal from the wearable system. In addition to alerts, the wearable system can also instruct a user to undertake or automatically activate certain stroke treatments. Stroke treatments can include inducing hypothermia to provide a neuro-protectant for the patient. The wearable system can trigger inhalation of cooling gases, activation of a cooling helmet, activation of an ultrasonic helmet to break up cloths, or ingestion or triggering administration of a drug patch or pill. The trigger can be instructions to the patient or medical responder, or automatic activation. In some instances, for Ischemic strokes, the wearable system can trigger mechanisms to increasing blood pressure and vasodilate blood vessels (through some of the mechanisms discussed above).

Treatments responsive to the detection of a potential stroke can be initiated by the patient if they are conscious and able, or by the medical response personnel via the home automation system. Patients in a particular high risk category may have previously been fitted with a wearable treatment device which can be activated automatically in response to a signal indicating the detection of a potential stroke, or activated by medical personnel following clinical examination which was initiated by an alert from the wearable system.

In some embodiments, a stroke detection device or system may trigger an audible alarm to alert a patient or caretaker, for example while sleeping, that a stroke event has occurred. The audible alarm can also enable emergency services to locate patient when they enter home.

In any of the embodiments described herein, a stroke detection device or system may record an onset of a stroke event and/or provide a "last known well" indicator to help inform treatment decisions.

In some embodiments, a system for detecting stroke includes a data processing module. The data processing module may be configured to extract a pattern. The pattern may suggest any ischemic or hemorrhagic episode very early, possibly imminently prior to an actual stroke event. In some embodiments, the pattern may be empirically determined, for example based on a population wide analysis, cohort analysis, and/or individual analysis of signals, which are analyzed for parameters and/or patterns indicative of stroke onset. In some embodiments, signal processing may employ signal processing tools, for example filtering, extracting, digitizing, data de-convolution, machine learning, and/or other methods known in the art. Specifically, the signal processing may use higher order statistics to ascertain hidden patterns in data. Use of higher order statistics, known as cumulants, and their Fourier spectra, often termed poly spectra, not only reveal the amplitude information in the higher order (such as those carried by power spectra or auto correlation) but may also include phase information. Phase information can reveal salient features of the data, otherwise unattainable from simple harmonic analysis. Another important feature of the polyspectra is the fact that they are blind to Gaussian processes. As a result, they can automatically handle Gaussians processes and thus improve signal to noise ratio, allowing novel detection. In some embodiments, a number of spectrums and their manipulations may be selected in order to identify hidden patterns in the sensed signals, for example BP(t), ECG(t) etc.

Figure 53:
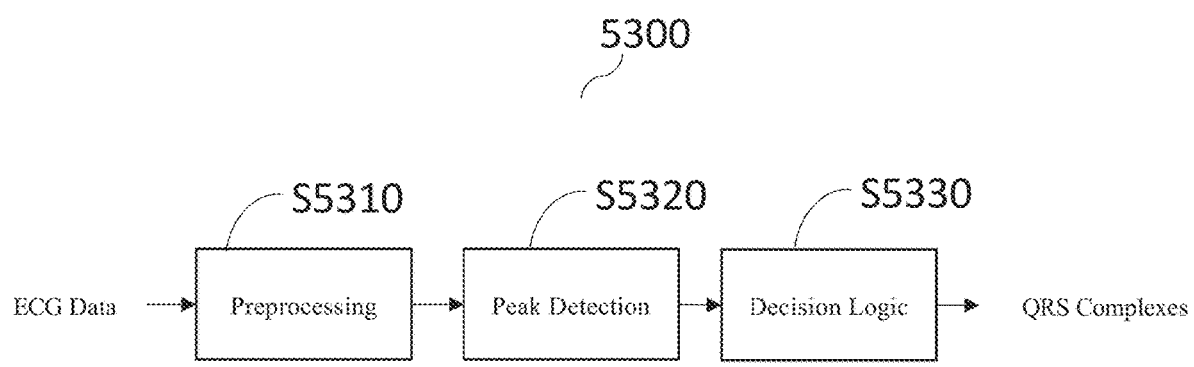
FIG. 53 illustrates a method of measuring heart rate variability of a user.
Figure 54:
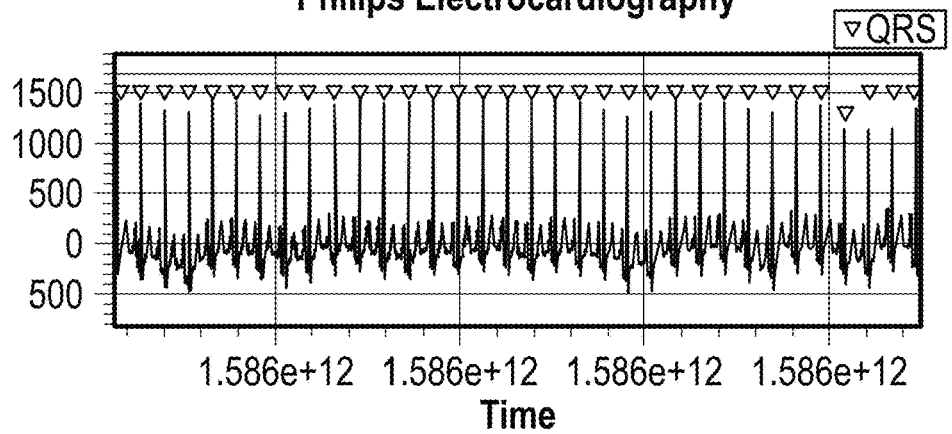
FIGS. 54-55 show graphs comprising electrocardiogram data for detecting an anomalous biologic event.
Figure 55:
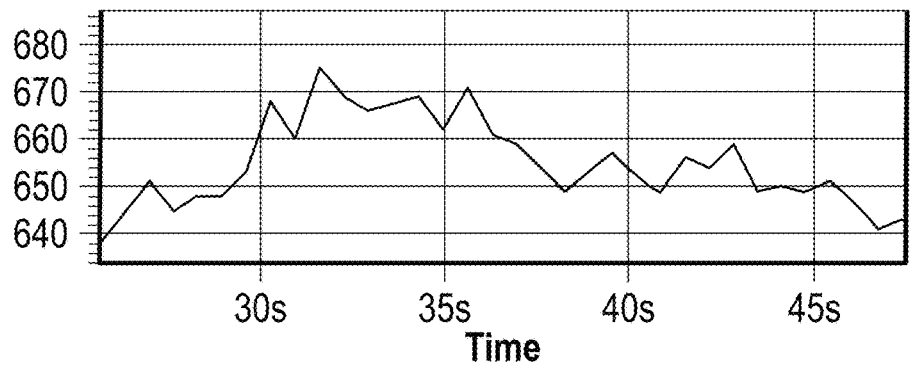

For example, as shown in FIGS. 53-55, a wearable system may collect electrocardiogram (ECG) data, pre-process the data, identify peaks in the data, and apply a decision logic to the data. FIG. 54 shows electrocardiogram data collected over time. FIG. 55 shows extracted R-R intervals from the electrocardiogram data (i.e., time between beats shown in milliseconds). The method 5300 shown in FIG. 53 may be used to calculate a heartbeat and/or a heart rate variability (i.e., specific changes in time between successive heart beats) of an individual. As shown in FIG. 53, ECG data is input into the method 5300, which detects QRS complexes (i.e., ventricular depolarization and the main spike in an ECG signal) in electrocardiographic signals. Preprocessing at block S5310 includes apply signal processing techniques for QRS feature extraction. For example, preprocessing may be applied to reduce the influence of muscle noise, powerline interference, baseline wander, and/or T-wave interference. Peak Detection at block S5320 includes QRS peak detection with adaptive threshold, for example. Each potential peak is compared to a baseline value. A baseline skin temperature is established by measuring unstimulated skin for a period of time. Once the baseline is determined, the stimulus (e.g., application of heat) can either reach a time limit or a temperature limit. The temperature limit can be absolute or relative to the baseline skin temperature. The baseline value is updated according to the amplitude of the detected peak. Decision Logic at block S5330 classifies the current peak as QRS, T-wave, or error beat, using the peak slope and/or peak-to-peak interval.

As shown in FIGS. 58-62, electrocardiogram data may be processed via several methods to extract various features, calculate one or more features (e.g., heart rate variability, heart rate, total power, etc.), etc. For example, a time domain analysis (FIG. 58), a geometrical analysis (FIG. 59), a frequency domain analysis (FIG. 60), and/or a nonlinear analysis (FIG. 61) analysis may be used.

Figure 58:
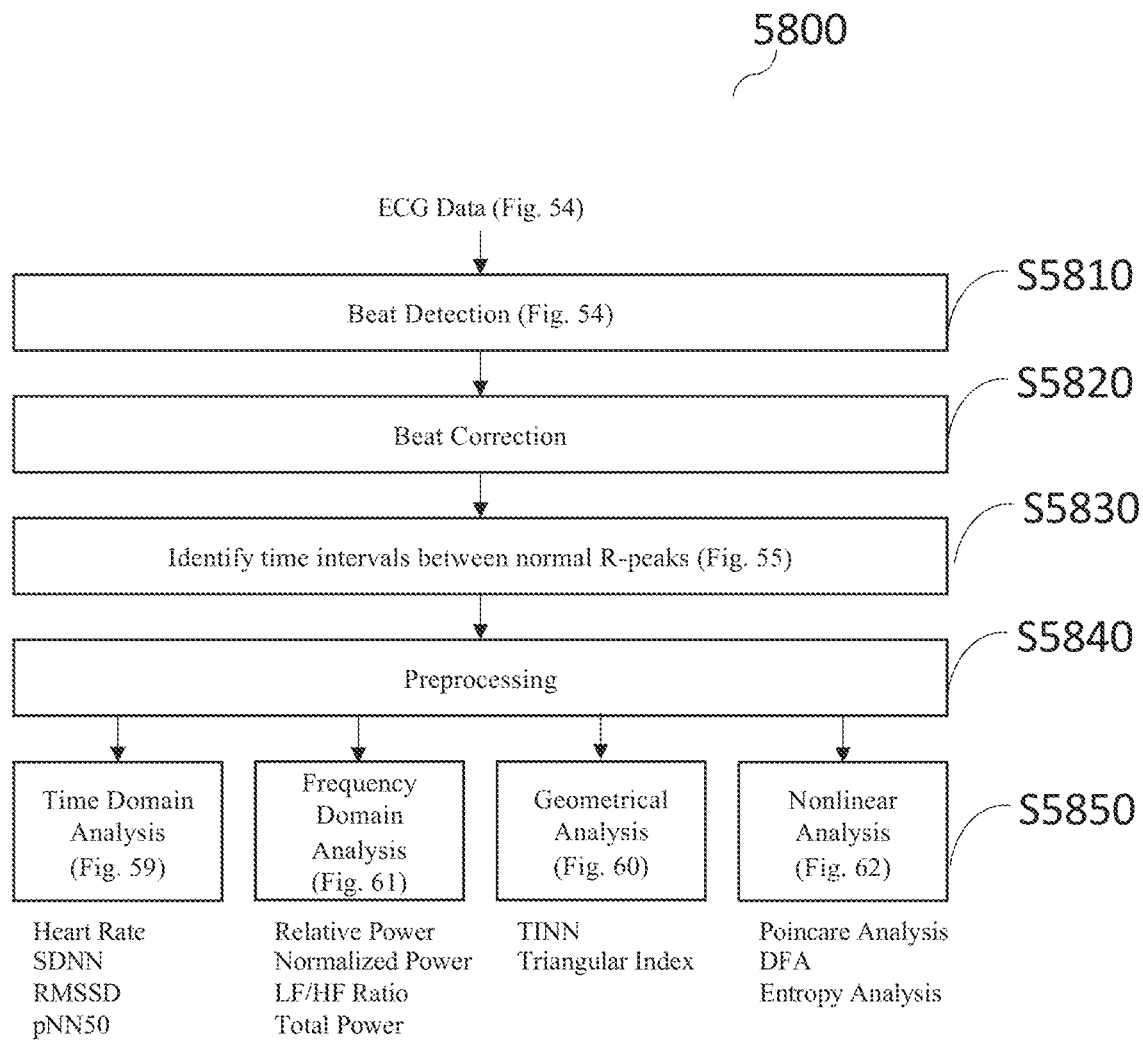
FIG. 58 shows a method for measuring heart rate variability of a user and various feature analyses.
Figure 59:
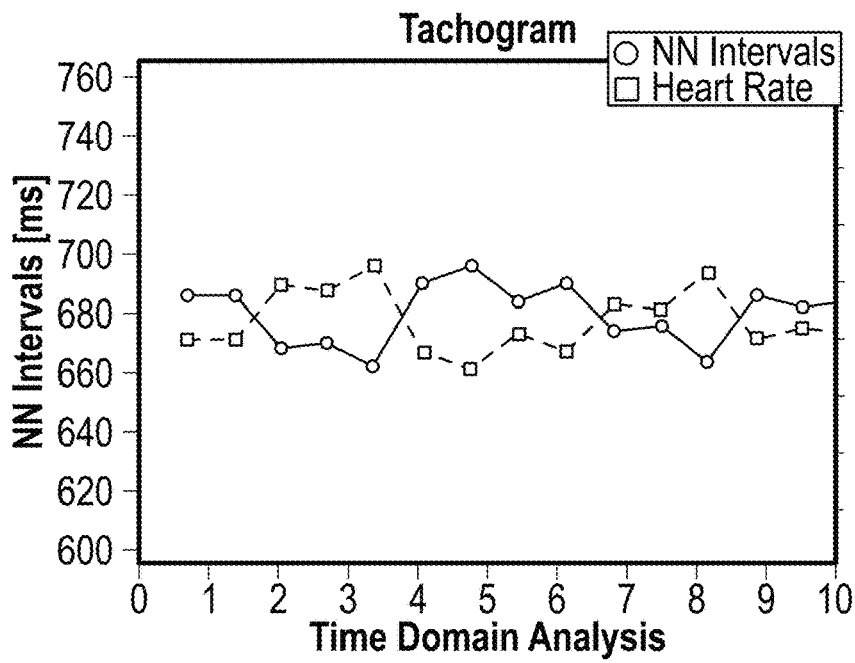
FIG. 59 shows a time domain analysis of heart rate variability data.
Figure 60:
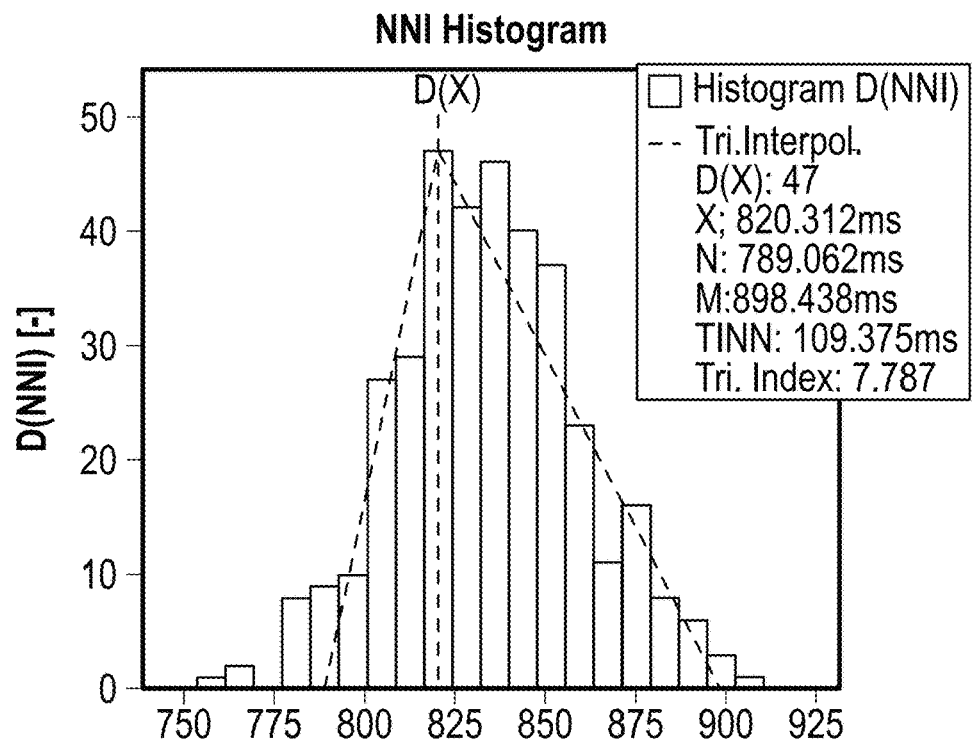
FIG. 60 shows a geometrical analysis of heart rate variability data.
Figure 61:
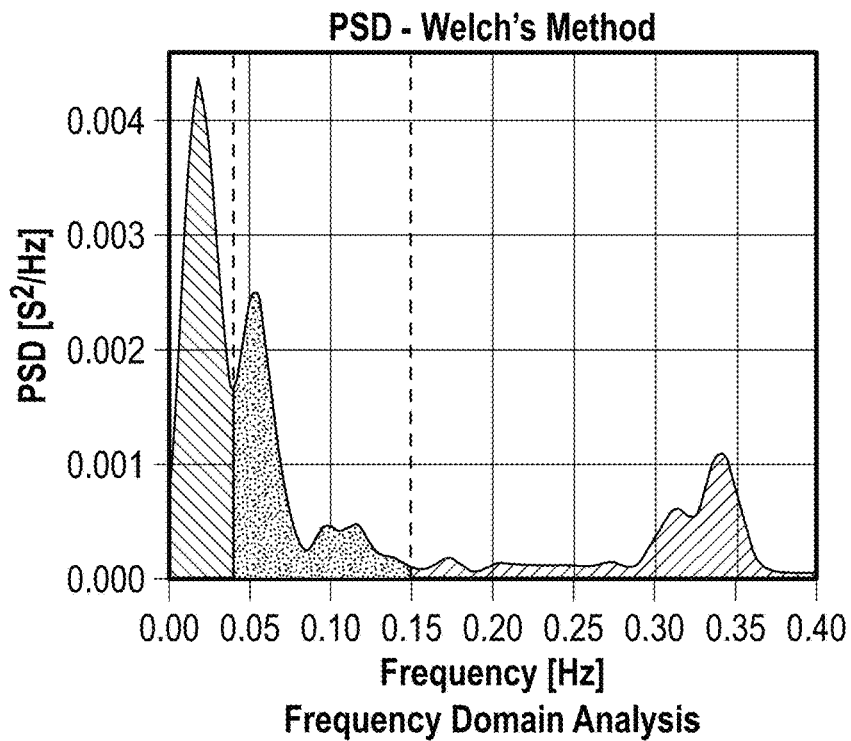
FIG. 61 shows a frequency domain analysis of heart rate variability data.
Figure 62:
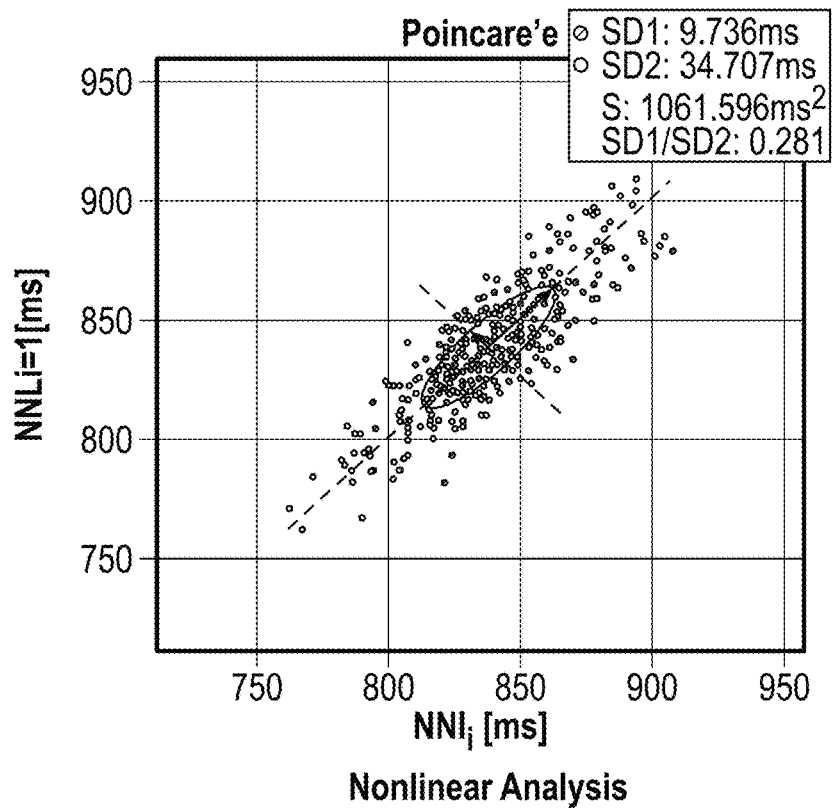
FIG. 62 shows a nonlinear analysis of heart rate variability data.

As shown in FIG. 58, ECG data (e.g., FIG. 54) is fed into method 5800. The method includes: receiving ECG data of a user using an ECG; detecting beats in the ECG data (e.g., detect R-peaks in the ECG data) S5810; identifying and correcting irregular beats (e.g., missed, extra, and ectopic beats; uses neighboring beats to correct each beat) S5820; identifying intervals between normal R-peaks (i.e., NN Interval Time Series (NNIs) S5830; preprocessing the data (e.g., corrects outliers of NNIs) S5840; and performing one or more analyses S5850. For example, a time domain analysis, as shown in FIG. 59 may be used to calculate heart rate (e.g., 60 divided by the mean of NNIs); the standard deviation of NNIs (SDNN); the root mean square of successive differences (RMSSD); and the percentage of adjacent NNIs that differ from each other by more than 50 ms (pNN50). Further, for example, a frequency domain analysis, as shown in FIG. 61, may be used to calculate a relative power (e.g., relative power of each frequency band (VLF/Total, LF/Total, HF/Total)); a normalized power (e.g., normalized powers of the LF and HF frequency bands (LF/(LF+HF), HF/(LF+HF)); an LF/HF Ratio (e.g., LF power/HF power); and/or a total power (e.g., total power over all frequency bands). Further, for example, a geometrical analysis, as shown in FIG. 60, may be used to calculate a baseline width of the interpolated triangle (TINN); and/or the ratio between the total number of NNI and the maximum of the NNI histogram distribution (i.e., triangular index). Further, for example, as shown in FIG. 62, a nonlinear analysis may be used to perform a Poincare Analysis (i.e., analyze Poincare plot of NNIs—SD1, SD2, SD Ratio, Ellipse Area); a DFA (Detrended Fluctuation Analysis (i.e., short and long-term fluctuations of NNIs); and/or an Entropy Analysis (i.e., computes approximate entropy, sample entropy, and fuzzy entropy of NNIs).

In some embodiments, the data processing module may use the continuously monitored or intermittently monitored physiological signals to differentiate changes from healthy "learned" or individualized baseline data. For example, the module may continuously learn the signals coming from an individual patient rather than using a statistical average taken from many patients. A custom reference signal may significantly improve minute changes in the physiological signals for an individual patient. In some embodiments, the physiological parameters may be processed as a function of time that includes the shape of the curve changes, including hidden harmonics, changes in higher order derivatives, etc.

Figure 33:
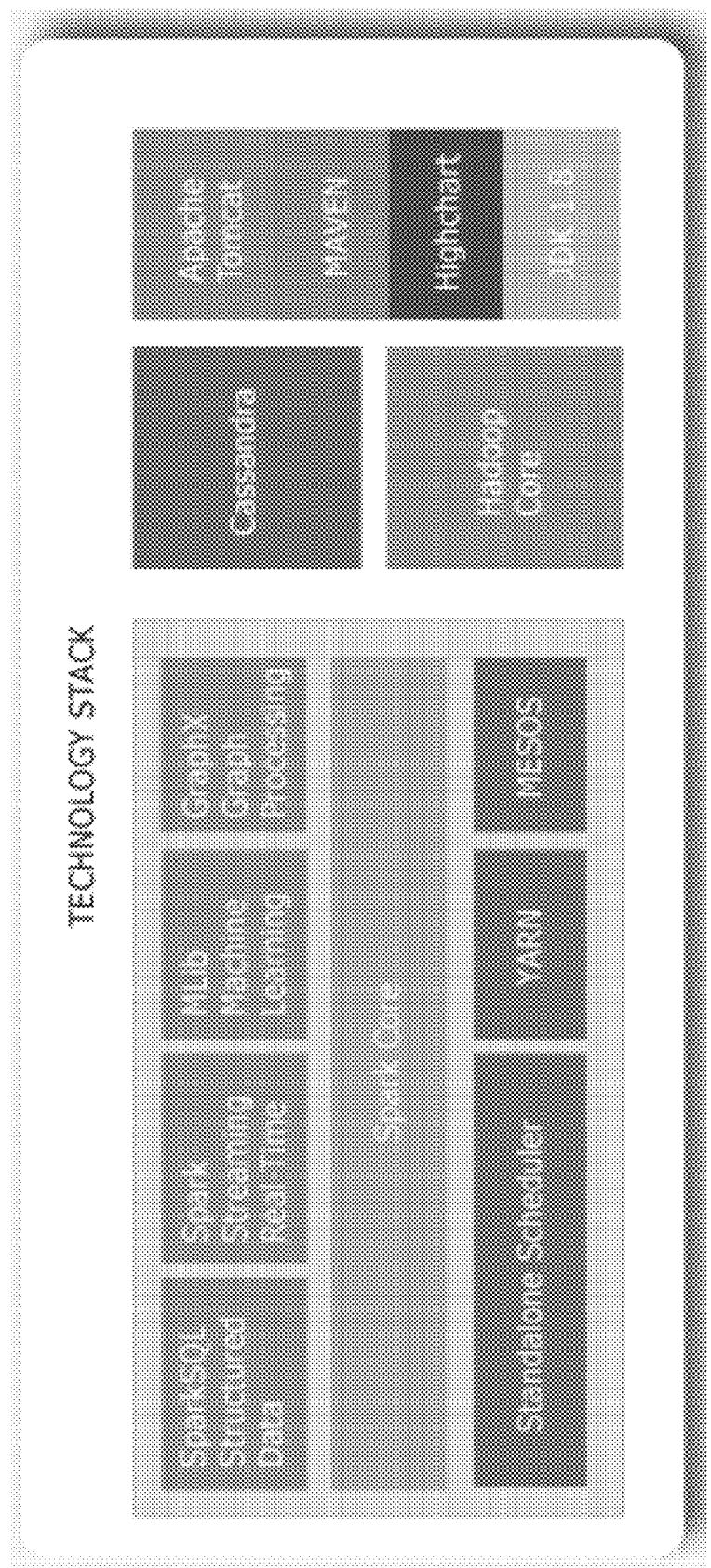
FIG. 33 illustrates one embodiment of an architecture of a data processing module.

FIG. 33 shows one embodiment of various components of a data processing module. The core engine for one embodiment of the data processing module may include one or more of the following parameters: fast processing, support for sophisticated analytics, real time stream processing, integration with both NoSQL and RDBMS, and integration with Hadoop.

Figure 34:
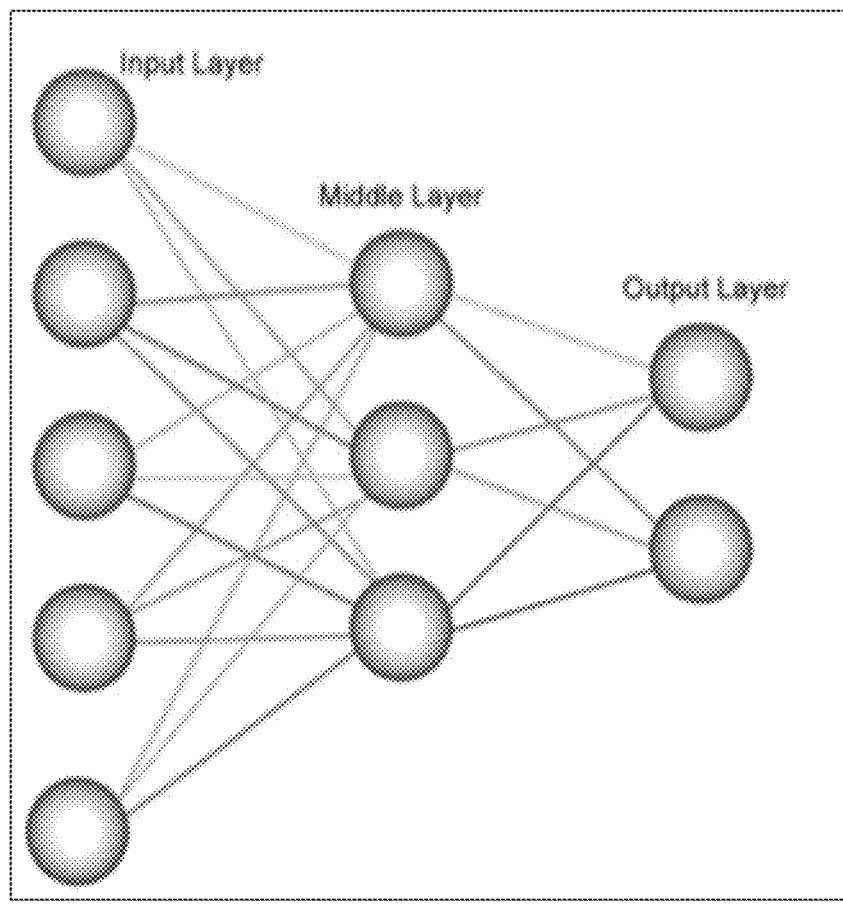
FIG. 34 illustrates one embodiment of machine learning model used to model movement patterns of a person, for example while sleeping.
Figure 35:
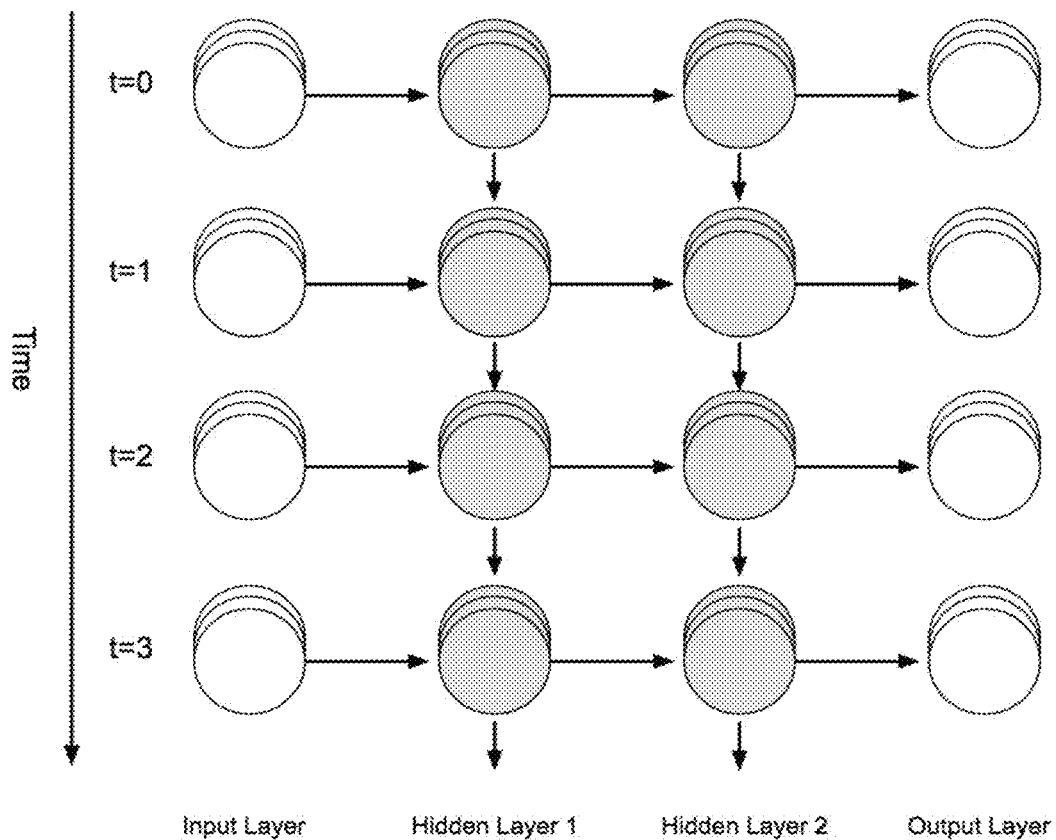
FIG. 35 illustrates another embodiment of machine learning model used to model movement patterns of a person.
Figure 36:
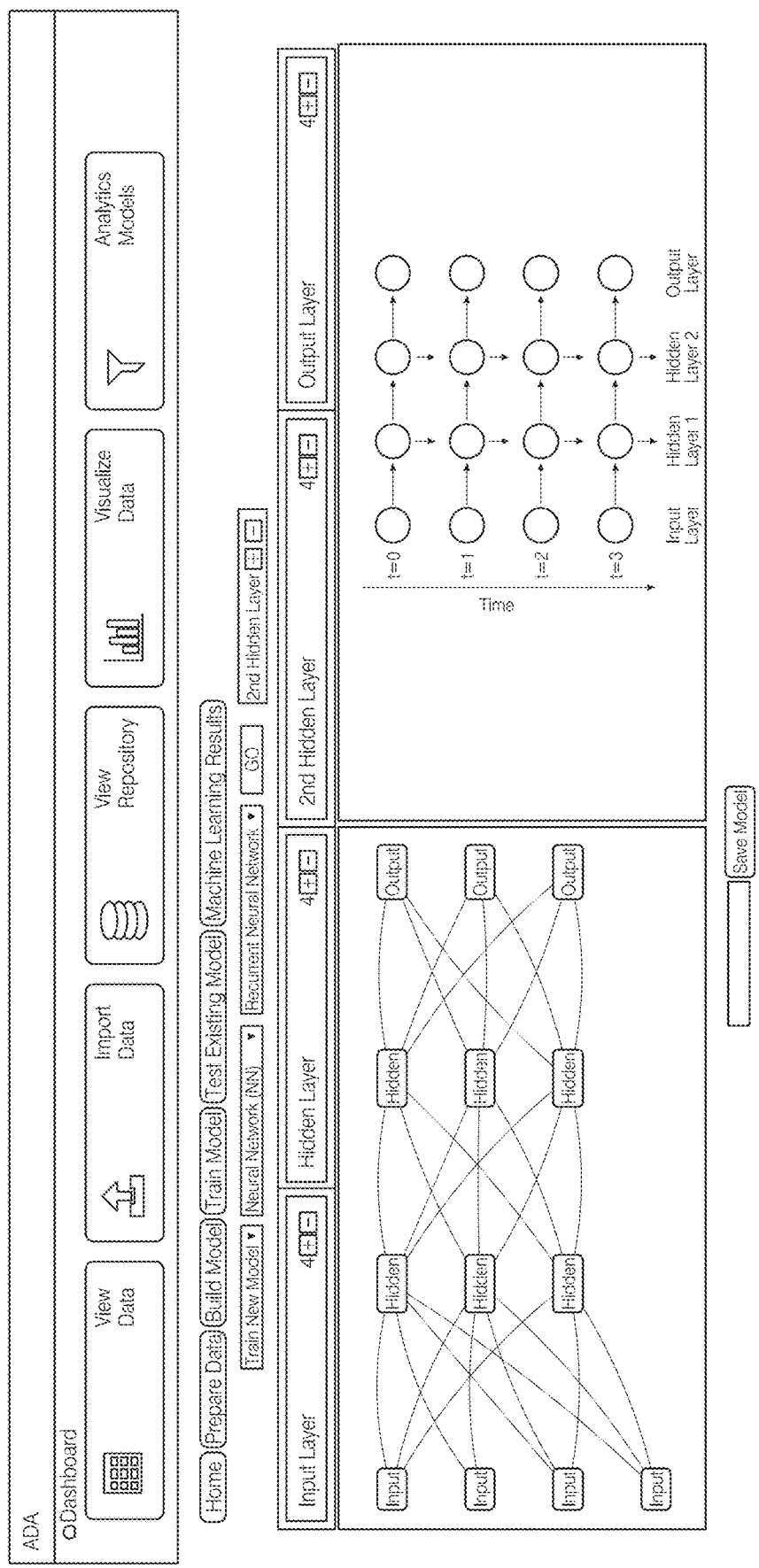
FIG. 36 illustrates another embodiment of machine learning model used to model movement patterns of a person.

The data processing module may employ various machine learning methods to identify patterns, extract patterns, identify parameters indicative of stroke onset, etc. Machine learning can be broadly defined as the application of any computer-enabled algorithm that can be applied against a data set to find a pattern in the data. A machine-learning algorithm is used to determine the relationship between a system's inputs and outputs using a learning data set that is representative of all the behavior found in the system. This learning can be supervised or unsupervised. For example, a simple neural network called a Multilayer Perceptron (MLP), as shown in FIG. 34, may be used to model various parameters or patterns of an individual, for example while sleeping. Each node is a neuron that uses a nonlinear activation function. Such a simple neural network may be used to distinguish data that are not linearly separable. In some embodiments, as shown in FIG. 35, a deep learning network may be used. A deep learning network may comprise a Leverage Recurrent Neural Networks (RNN) implementation, as shown in FIG. 36. The system creates layers of interconnected networks, where each layer corresponds to a time slice. RNN are proven highly effective in handling time series data, assumes training inputs are time dependent, capable of accurately modeling/predicting changes through time, capable of generating an actual output value for a data point versus giving just a range, and each time slice is its own feed forward network—specified by a user.

In some embodiments, a system for providing comprehensive stroke care comprises one or more of: educational resources tailored to the patient based on demographics, type of stroke, co-morbidities, medications, etc; management tools to assist with the dramatic changes in lifestyle, such as reminders (e.g., medications, rehabilitation appointments, etc.), collaborative care resources (e.g., for spouse, doctor, physical therapist, caretaker, etc.), activity tracking with continuous data collection via a wearable, fitness tracking and guided meditation, stroke risk level assessment, etc.; community with others as part of the first national stroke survivor network where stroke survivors can give and receive support and encouragement connecting both patients and caregivers, "check in" with others in your group to make sure they are making progress towards their goals and are doing well mentally, share stories and relate to others, receive telemedicine/rehab resources with a speech therapist or mental health counselor; patient rehab and monitoring, or other enabling technologies; set recovery goals and track progress, cognitive evaluation tools, etc.; stroke Detection to alert caretakers via call/message, communication tools for patients with aphasia, etc.

Example 1

Various functional symptoms, quantitative markers, and blood/fluid products were scored for their ability to detect stroke. The scoring criteria were the following: should be grounded in scientific rationale, should be highly sensitive (>90%), should only have very few false positives (<10%), and stroke detection should be passive (automatic). Each of these parameters were scored from 0 to 5, except for passive detection which was scored on a scale of 0 (active detection) to 1 (passive detection). The score was then multiplied by a weight factor, shown in Table 1 below, and all the weighted factors summed to yield a total score.

As shown below in Tables 2 and 5, the functional symptoms with the highest total score were facial muscle weakness, unilateral weakness, limited visual field, gaze altered, and speech change. Of these functional symptoms, only facial muscle weakness, unilateral weakness, and speech change can be detected passively.

TABLE 1

Analyzed Factors and Associated Weights

| Factor (score each on (0-5)) | Weighting Factor |
|---|---|
| Should be grounded in scientific rationale | 5 |
| Should be highly sensitive (>90%) | 5 |
| Should only have very few FPs (<10%) | 2 |
| Stroke detection should be passive (automatic) | 4 |

TABLE 2

Analysis of Functional Symptoms of Stroke

| Functional Symptom | Time Period | Sample Embodiment | Scientific rationale | Detection passive? (passive = 1, active = 0) | Sensitivity | Specificity | Total Score |
|---|---|---|---|---|---|---|---|
| Speech Change | During, after | Amazon Alexa devices, Smart speakers, Smartwatch, external microphone coupled to 3$^{rd}$ party device | 5 | 1 | 4 | 3 | 55 |
| Speech Comprehension | During, after | Amazon Alexa devices, Smart speakers, Smartwatch | 5 | 0 | 4 | 2 | 49 |
| Text Comprehension | During, after | Phone App, Tablet App | 3 | 0 | 4 | 2 | 39 |
| Consciousness | During | Camera, Wearable, Smartwatch | 4 | 1 | 3 | 2 | 43 |
| Coordination/ Directions | During | Camera, Wearable, Smartwatch | 3 | 0 | 3 | 2 | 34 |
| Facial Muscle Weakness | During, after | Camera, Wearable | 5 | 1 | 5 | 4 | 62 |

TABLE 2-continued

Analysis of Functional Symptoms of Stroke

| Functional Symptom | Time Period | Sample Embodiment | Scientific rationale | Detection passive? (passive = 1, active = 0) | Sensitivity | Specificity | Total Score |
|---|---|---|---|---|---|---|---|
| Arm Weakness | During | Camera, Wearable | 5 | 1 | 4 | 3 | 55 |
| Body Weakness - Grip | During | Camera, Wearable | 3 | 0 | 3 | 3 | 36 |
| Leg weakness | During | Camera, Wearable | 4 | 1 | 3 | 2 | 43 |
| Foot weakness | During | Camera, Wearable | 4 | 1 | 3 | 2 | 43 |
| Unilateral weakness | During | Camera, Wearable | 5 | 1 | 5 | 4 | 62 |
| Difficulty Walking | During, after | Camera, Wearable | 4 | 1 | 2 | 2 | 38 |
| Vertigo | During | Camera, Wearable | 4 | 0 | 4 | 2 | 44 |
| Sudden Vision Problems | During | Amazon Alexa devices, Phone app | 5 | 0 | 4 | 4 | 53 |
| Limited Visual Field | During | Amazon Alexa devices, Phone app | 5 | 0 | 5 | 3 | 56 |
| Gaze Altered | During | Camera, Phone app | 5 | 0 | 5 | 3 | 56 |
| Thunderclap Headache | Before, during, after | Amazon Alexa devices, Phone app | 5 | 0 | 4 | 3 | 51 |
| Nuchal rigidity (nape of neck) | | Amazon Alexa devices, Phone app | 5 | 0 | 3 | 3 | 46 |
| Respiration | Before, during | Wearable device, non-contact Doppler radar, Eulerian video processing techniques | 3 | 1 | 2 | 2 | 33 |
| Blood Pressure | Before, during | Wearable device (continuous use; periodic use) | 3 | 1 | 4 | 2 | 43 |

As shown in Tables 3 and 5, the quantitative markers with the highest total score were cerebral blood flow, EEG asymmetry, carotid artery stenosis, volumetric impedance spectroscopy, and limb asymmetry. Of these quantitative markers, all were considered to be detectable passively.

TABLE 3

Analysis of Quantitative Symptoms of Stroke

| Marker | Time Period | Sample Embodiment | Scientific rationale | Detection passive? (passive = 1, active = 0) | Sensitivity | Specificity | Total Score |
|---|---|---|---|---|---|---|---|
| Volumetric impedance spectroscopy | During, after | Wearable, implant | 5 | 1 | 3 | 4 | 52 |
| EEG asymmetry | During, after | Wearable, implant | 5 | 1 | 4 | 4 | 57 |
| Brain perfusion | During, after | Wearable | 4 | 1 | 3 | 4 | 47 |
| Skin temperature | After | Wearable, IR imaging | 4 | 1 | 3 | 2 | 43 |

TABLE 3-continued

Analysis of Quantitative Symptoms of Stroke

| Marker | Time Period | Sample Embodiment | Scientific rationale | Detection passive? (passive = 1, active = 0) | Sensitivity | Specificity | Total Score |
|---|---|---|---|---|---|---|---|
| Hyperhidrosis | After | Wearable | 3 | 1 | 4 | 2 | 43 |
| Limb asymmetry | During, after | Wearable, camera | 4 | 1 | 4 | 4 | 52 |
| Drift and pronation test | During, after | Camera | 4 | 0 | 4 | 4 | 48 |
| Cutaneous blood flow | After | Wearable, camera | 3 | 1 | 3 | 3 | 40 |
| Muscle tone | During, after | Wearable, camera | 3 | 1 | 4 | 3 | 45 |
| Heartrate variability | After | Wearable, implant, non-contact, Doppler radar | 3 | 1 | 3 | 3 | 40 |
| Facial surface EMG | During, after | Wearable, implant | 4 | 1 | 4 | 4 | 52 |
| Cerebral blood flow (CBF) | During, after | Wearable, implant | 5 | 1 | 5 | 5 | 64 |
| Carotid artery stenosis | During, after | Implant | 5 | 1 | 4 | 3 | 55 |
| Salivary cortisol | During, after | Wearable, implant | 3 | 1 | 2 | 2 | 33 |
| Neuron specific enolase (NSE) | During, after | Wearable, implant | 4 | 1 | 4 | 4 | 52 |
| Salivary NSE | During, after | Wearable, implant | 4 | 1 | 4 | 4 | 52 |

As shown in Tables 4 and 5, the products with the highest total score were Cornell University's products, SMART-Chip, and ReST. Of these, none were considered to be passive detection.

TABLE 4

Analysis of Products for Stroke Rapid Diagnosis

| Product | Time to Detect | Notes | Scientific rationale | Diagnosis passive? (passive = 1, active = 0) | Sensitivity | Specificity | Total Score |
|---|---|---|---|---|---|---|---|
| CoaguCheck (Roche) | <1 min | To shorten door-needle time; determine to start TPA faster | 2 | 0 | 2 | 2 | 24 |
| HemoChron (ITC) | ~few mins | To shorten door-needle time; determine to start TPA faster | 2 | 0 | 2 | 2 | 24 |
| ISTAT (Abbott) | <2 mins | To shorten door-needle time; determine to start TPA faster | 2 | 0 | 2 | 2 | 24 |
| Cornell University | not known | Distinguish stroke from stroke mimics | 4 | 0 | 3 | 5 | 45 |
| ReST (Valtari Bio Inc) | <10 mins | Initial stroke vs no stroke diagnosis | 3 | 0 | 3 | 3 | 36 |
| SMARTChip (Sarissa Biomedical) | ~few mins | Stroke vs no stroke using one drop of blood | 3 | 0 | 4 | 2 | 39 |

TABLE 5

| Results | | |
|---|---|---|
| Functional | Total Score | Symptom |
| #1 | 62 | Facial Muscle Weakness |
| #2 | 62 | Unilateral weakness |
| #3 | 56 | Limited Visual Field |
| #4 | 56 | Gaze Altered |
| #5 | 55 | Speech Change |
| Quantitative | Total Score | Symptom |
| #1 | 64 | Cerebral blood flow (CBF) |
| #2 | 57 | EEG asymmetry |
| #3 | 55 | Carotid artery stenosis |
| #4 | 52 | Volumetric impedance spectroscopy |
| #5 | 52 | Limb asymmetry |
| Blood | Total Score | Organization |
| #1 | 45 | Cornell University |
| #2 | 39 | SMARTChip (Sarissa Biomedical) |
| #3 | 36 | ReST (Valtari Bio Inc) |

Example 2

Symmetrical and asymmetrical acceleration and distance were measured using an Apple® Watch and displayed in a graphic representation (FIGS. 9-11, 27-32) in an application on a computing device. For this example, the implementation also measures the resolution of the Apple® Watch accelerometer sensor and existing API capabilities.

For this example, the device was worn on a user's wrist. Any acceleration of the wrist was recoded and saved in the onboard database, including acceleration in x-, y- and z-axes. The computing device has a "sync" function that allows the data to be transferred to a computing device for analysis. Tables 6-8 show acceleration data, distance data, and calculated movement data (i.e., distance traveled), respectively, acquired using an Apple® Watch worn on each wrist of a user. Data values were recorded at various time points, as shown in FIGS. 9-11, 27-32.

TABLE 6

| Acceleration (XYZ) of a Wrist | | | | | |
|---|---|---|---|---|---|
| | 30 | 60 | 90 | 120 | 150 |
| Acceleration X axis | ~10 | ~0 | ~0 | ~15 | ~0 |
| Acceleration Y axis | ~10 | ~0 | ~0 | ~15 | ~0 |
| Acceleration Z axis | ~10 | ~0 | ~0 | ~15 | ~0 |

TABLE 7

| Distance Measurement of a Wrist | | | | | |
|---|---|---|---|---|---|
| | 30 | 60 | 90 | 120 | 150 |
| Acceleration X axis | ~10 | ~0 | ~0 | ~15 | ~0 |
| Acceleration Y axis | ~10 | ~0 | ~0 | ~15 | ~0 |
| Acceleration Z axis | ~10 | ~0 | ~0 | ~15 | ~0 |

TABLE 8

| Movement Calculation of a Wrist | | | | |
|---|---|---|---|---|
| | 10 | 20 | 30 | 40 |
| Description Label | 143 | 51 | 247 | 207 |

Taken together, a system for stroke detection may include detecting one or more of: acceleration in x-, y- and/or z-axes; and/or distance in x-, y- and/or z-axes; and, in some embodiments, calculating a distance traveled (i.e., movement) to determine asymmetrical limb movement, gait, etc. possibly indicative of a stroke event.

The systems and methods of the preferred embodiment and variations thereof can be embodied and/or implemented at least in part as a machine configured to receive a computer-readable medium storing computer-readable instruction. The instructions are preferably executed by computer-executable components preferably integrated with the system and one or more portions of the hardware processor on the device for detecting stroke and/or computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific hardware processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "signal" may include, and is contemplated to include, a plurality of signals. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Example Embodiments

A wearable system for detecting an anomalous biologic event in a person, comprising one or more of the following:
- a body having a first surface opposite a second surface in contact with a skin surface of a person;
- a heat source in communication with the skin surface, wherein the heat source is configured to heat the skin surface to a target temperature;
- a skin temperature sensor positioned on the second surface and configured to measure a temperature of the skin surface in contact with the heat source;
- a blood volume sensor positioned on the second surface and configured to measure a blood volume of the skin surface; and
- a hardware processor communicatively coupled to the heat source, the blood volume sensor, the skin temperature sensor, and an environmental temperature sensor configured to measure a temperature of the environment around the wearable system, wherein the hardware processor is configured to:
- receive a baseline blood volume signal from the blood volume sensor,
- output a heating signal to the heat source to initiate a heating cycle, wherein the heating cycle comprises heating the skin surface to the target temperature,
- receive a second blood volume signal from the blood volume sensor in response to the skin surface reaching the target temperature,
- compare the second blood volume signal to the baseline blood volume signal, and
- determine whether an anomalous biologic event has occurred based on the comparison.

The wearable system of any embodiment disclosed herein, wherein the second blood volume signal comprises a set of blood volume signals, such that the blood volume of the skin surface is measured repeatedly before, during, and after a heating cycle of the heat source.

The wearable system of any embodiment disclosed herein, wherein the second blood volume signal comprises a plurality of blood volume signals, such that the blood volume of the skin surface is measured continuously before, during, and after a heating cycle of the heat source.

The wearable system of any embodiment disclosed herein, wherein hardware processor is further configured to receive the second blood volume signal after the target temperature is reached, after a predetermined length of time has expired, or after one or more heating cycles have concluded.

The wearable system of any embodiment disclosed herein, wherein comparing comprises calculating a baseline ratio of alternating current (AC) to direct current (DC) for the baseline blood volume signal and a second ratio of AC to DC for the second blood volume signal and comparing the baseline ratio to the second ratio.

The wearable system of any embodiment disclosed herein, wherein the environmental temperature sensor is positioned on the first side of the body of the wearable system.

The wearable system of any embodiment disclosed herein, further comprising a remote computing device communicative coupled to the wearable system and comprising the environmental temperature sensor.

The wearable system of any embodiment disclosed herein, wherein the remote computing device comprises one of: a laptop, cellular device, a workstation, a server, a desktop computer, a personal digital assistant, a second wearable system or device, or a netbook.

The wearable system of any embodiment disclosed herein, wherein the heat source is positioned on the second surface of the body.

The wearable system of any embodiment disclosed herein, wherein the hardware processor is further configured to:
- receive baseline temperature signals from the skin temperature sensor and the environmental temperature sensor,
- determine the target temperature based on the baseline temperature signals, and
- determine whether the target temperature is below a maximum temperature value.

The wearable system of any embodiment disclosed herein, wherein the hardware processor is further configured to cycle the heat source to maintain the target temperature.

The wearable system of any embodiment disclosed herein, further comprising one or more electrodermal activity sensors positioned on the second surface.

The wearable system of any embodiment disclosed herein, wherein the one or more electrodermal activity sensors are spaced apart from the heating element by about 0.25 inches to about 4 inches.

The wearable system of any embodiment disclosed herein, further comprising one or more motion sensors configured to measure a motion of a body portion to which the wearable system is coupled.

The wearable system of any embodiment disclosed herein, wherein the first and second surfaces define a cavity therebetween to provide airflow between the first and second surfaces.

The wearable system of any embodiment disclosed herein, wherein the hardware processor resides on or within the first surface.

The wearable system of any embodiment disclosed herein, wherein the cavity defined by the first and second surfaces physically separates the heat source from the hardware processor on or within the first surface.

The wearable system of any embodiment disclosed herein, wherein the cavity defined by the first and second surfaces has sufficient volume to facilitate cooling of the heat source in between heating cycles.

The wearable system of any embodiment disclosed herein, wherein the anomalous biologic event comprises a stroke event.

The wearable system of any embodiment disclosed herein, wherein the wearable system is positioned on a left limb of a user and a second wearable system is positioned on a right limb of the user, wherein the second wearable system comprises a second heating element, a second skin temperature sensor, and a second blood volume sensor, wherein the hardware processor is further configured to compare right side blood volume signals to left side blood volume signals to determine whether the anomalous biologic event has occurred.

The wearable system of any embodiment disclosed herein, wherein the hardware processor is further configured to:
synchronize the signals received from the left limb and the right limb in time; and
compare the synchronized signals from the left limb and the right limb to determine whether the anomalous biologic event occurred.

The wearable system of any embodiment disclosed herein, wherein the comparison takes into account a baseline difference between the left limb and the right limb.

The wearable system of any embodiment disclosed herein, further comprising a tensionable band coupled to the body.

The wearable system of any embodiment disclosed herein, wherein the tensionable band further comprises a visual indicator to indicate when one or more of: the heating element, the skin temperature sensor, the blood volume sensor, or a combination thereof is sufficiently coupled to the skin surface to enable accurate sensor readings.

The wearable system of any embodiment disclosed herein, wherein one or more ends of the tensionable band are coupled to the body at a position that is centered with respect to one or more sensors positioned on the second surface.

The wearable system of any embodiment disclosed herein, wherein the heat source is positioned concentrically about one or both of the blood volume sensor and the skin temperature sensor.

The wearable system of any embodiment disclosed herein, wherein the blood volume sensor comprises a photoplethysmography sensor or an impedance plethysmographic sensor.

The wearable system of any embodiment disclosed herein, wherein the skin temperature sensor comprises a thermocouple, a resistance temperature detector, a thermistor, or an infrared temperature sensor.

The wearable system of any embodiment disclosed herein, further comprising a support structure coupled to the heat source and configured to couple the heat source to the second surface and at least partially expose the heat source to the cavity.

The wearable system of any embodiment disclosed herein, wherein the blood volume sensor is further configured to measure one or more of: heart rate, heart rate variability, or oxygen saturation.

The wearable system of any embodiment disclosed herein, wherein the target temperature is individualized to the user.

The wearable system of any embodiment disclosed herein, wherein individualization of the target temperature comprises receiving a user input related to perceived temperature of the skin surface.

The wearable system of any embodiment disclosed herein, wherein individualization of the target temperature is based on signals received from the blood volume sensor.

The wearable system of any embodiment disclosed herein, wherein the heat source comprises one of: a heating element or an environmental temperature.

The wearable system of any embodiment disclosed herein, wherein the hardware processor is configured to transmit an electronic message to a first electronic system responsive to the determination of the anomalous biologic event, said first electronic system configured to electronically manage a home automation system.

The wearable system of any embodiment disclosed herein, wherein the home automation system comprises a door lock and wherein said electronic message is configured to instruct the first electronic system to unlock the door lock.

The wearable system of any embodiment disclosed herein, wherein the home automation system comprises a home alarm system and wherein said electronic message is configured to instruct the first electronic system to disable the home alarm system.

The wearable system of any embodiment disclosed herein, wherein the home automation system comprises a display and wherein said electronic message is configured to instruct the first electronic system to display user's medical information.

The wearable system of any embodiment disclosed herein, wherein the medical information comprises medication information and/or medication regimen compliance.

The wearable system of any embodiment disclosed herein, wherein the home automation system comprises a display and wherein said electronic message is configured to instruct the first electronic system to display stroke treatment user interface.

The wearable system of any embodiment disclosed herein, wherein the home automation system comprises a speaker system and wherein said electronic message is configured to instruct the first electronic system to trigger an audible alarm with the speaker system.

The wearable system of any embodiment disclosed herein, wherein the hardware processor is further configured to alert a third party computing system responsive to the determination of the anomalous biologic event.

The wearable system of any embodiment disclosed herein, wherein the third party computing system comprises an emergency service system.

The wearable system of any embodiment disclosed herein, wherein the third party computing system comprises a clinician computing system.

The wearable system of any embodiment disclosed herein, wherein the hardware processor is further configured to initiate treatment protocol responsive to the detection of anomalous biologic event.

The wearable system of any embodiment disclosed herein, further comprising a wearable treatment system and said treatment protocol is configured to activate the wearable treatment system.

The wearable system of any embodiment disclosed herein, wherein the wearable treatment system comprises an ultrasonic helmet.

The wearable system of any embodiment disclosed herein, wherein the wearable treatment system comprises a cooling gas delivery system.

The wearable system of any embodiment disclosed herein, wherein the wearable treatment system comprises a cooling helmet.

A wearable system for detecting an anomalous biologic event in a person, comprising one or more of the following:
a body having a first surface opposite a second surface in contact with a skin surface of a person, the first and second surfaces defining a cavity therebetween to provide airflow between the first and second surfaces;
a heating element positioned on the second surface and configured to heat the skin surface for a predetermined length of time;

a skin temperature sensor positioned on the second surface and configured to measure a temperature of the skin surface in contact with the heating element;

a blood volume sensor positioned on the second surface and configured to measure a blood volume of the skin surface;

a hardware processor communicatively coupled to the heating element, the blood volume sensor, the skin temperature sensor, and an environmental temperature sensor configured to measure a temperature of the environment around the wearable system, wherein the hardware processor is configured to:

receive a baseline blood volume signal from the blood volume sensor, output a heating signal to the heating element to initiate a heating cycle, wherein the heating cycle comprises heating the skin surface to a target temperature, receive a second blood volume signal from the blood volume sensor in response to the skin surface reaching the target temperature, compare the second blood volume signal to the baseline blood volume signal, and determine whether an anomalous biologic event has occurred based on the comparison.

A wearable system for detecting an anomalous biologic event in a person, comprising one or more of the following:

a body having a first surface opposite a second surface in contact with a skin surface of a person;

a heat source in communication with the skin surface, wherein the heat source is configured to heat the skin surface to a target temperature;

a skin temperature sensor positioned on the second surface and configured to measure a temperature of the skin surface in contact with the heat source;

a sensor positioned on the second surface and configured to measure a parameter of interest of the person; and a hardware processor communicatively coupled to the heat source, the sensor, the skin temperature sensor, and an environmental temperature sensor configured to measure a temperature of the environment around the wearable system, wherein the hardware processor is configured to:

receive a baseline sensor signal from the sensor, output a heating signal to the heat source to initiate a heating cycle, wherein the heating cycle comprises heating the skin surface to the target temperature, receive a second sensor signal from the sensor in response to the skin surface reaching the target temperature, compare the second sensor signal to the baseline sensor signal, and determine whether an anomalous biologic event has occurred based on the comparison.

The wearable system of any embodiment disclosed herein, wherein the sensor is selected from the group consisting of: a stretch sensor, an electrodermal activity sensor, an electrocardiogram sensor, a camera, or a blood volume sensor.

The wearable system of any embodiment disclosed herein, wherein the parameter of interest includes one or more of: a blood pressure, a heart rate, a heart rate variability, a gaze, a facial expression, a skin conductance response, a vasodilation response, or a dilation response.

A wearable system for detecting an anomalous biologic event in a person, comprising one or more of the following:

a body having a first surface opposite a second surface in contact with a skin surface of a person;

a stimulus source in communication with the skin surface, wherein the stimulus source is configured to apply a stimulus to the skin surface;

a blood volume sensor positioned on the second surface and configured to measure a blood volume of the skin surface; and a hardware processor communicatively coupled to the stimulus source and the blood volume sensor, wherein the hardware processor is configured to:

receive a baseline blood volume signal from the blood volume sensor, output a stimulus signal to the stimulus source to initiate a stimulus cycle, receive a second blood volume signal from the blood volume sensor in response to the initiation of the stimulus cycle, compare the second blood volume signal to the baseline blood volume signal, and determine whether an anomalous biologic event has occurred based on the comparison.

The wearable system of any embodiment disclosed herein, wherein the stimulus source comprises a heat source.

The wearable system of any embodiment disclosed herein, wherein the stimulus source comprises an electrical source.

The wearable system of any embodiment disclosed herein, wherein the comparison comprises determining a change in vasodilation response.

The wearable system of any embodiment disclosed herein, wherein the stimulus source comprises a Peltier cooler.

The wearable system of any embodiment disclosed herein, wherein the second blood volume signal comprises a set of blood volume signals, such that the blood volume of the skin surface is measured repeatedly before, during, and after the stimulus cycle.

The wearable system of any embodiment disclosed herein, wherein the second blood volume signal comprises a plurality of blood volume signals, such that the blood volume of the skin surface is measured continuously before, during, and after the stimulus cycle.

The wearable system of any embodiment disclosed herein, wherein hardware processor is further configured to receive the second blood volume signal after a target stimulus is reached, after a predetermined length of time has expired, or after one or more stimulus cycles have concluded.

The wearable system of any embodiment disclosed herein, wherein comparing comprises calculating a baseline ratio of alternating current (AC) to direct current (DC) for the baseline blood volume signal and a second ratio of AC to DC for the second blood volume signal and comparing the baseline ratio to the second ratio.

The wearable system of any embodiment disclosed herein, wherein the blood volume sensor is positioned on the first side of the body of the wearable system.

The wearable system of any embodiment disclosed herein, further comprising a remote computing device communicative coupled to the wearable system and comprising the blood volume sensor.

The wearable system of any embodiment disclosed herein, wherein the remote computing device comprises one of: a laptop, cellular device, a workstation, a server, a desktop computer, a personal digital assistant, a second wearable system or device, or a netbook.

The wearable system of any embodiment disclosed herein, wherein the stimulus source is positioned on the second surface of the body.

The wearable system of any embodiment disclosed herein, wherein the hardware processor is further configured to:
  receive baseline blood volume signals from the blood volume sensor,
  determine the target blood volume based on the baseline blood volume signals, and
  determine whether the target blood volume is below a maximum blood volume value.

The wearable system of any embodiment disclosed herein, wherein the hardware processor is further configured to cycle the stimulus source to maintain the target blood volume.

The wearable system of any embodiment disclosed herein, further comprising one or more electrodermal activity sensors positioned on the second surface.

The wearable system of any embodiment disclosed herein, wherein the one or more electrodermal activity sensors are spaced apart from the stimulus source by about 0.25 inches to about 4 inches.

The wearable system of any embodiment disclosed herein, further comprising one or more motion sensors configured to measure a motion of a body portion to which the wearable system is coupled.

The wearable system of any embodiment disclosed herein, wherein the first and second surfaces define a cavity therebetween to provide airflow between the first and second surfaces.

The wearable system of any embodiment disclosed herein, wherein the hardware processor resides on or within the first surface.

The wearable system of any embodiment disclosed herein, wherein the cavity defined by the first and second surfaces physically separates the stimulus source from the hardware processor on or within the first surface.

The wearable system of any embodiment disclosed herein, wherein the cavity defined by the first and second surfaces has sufficient volume to facilitate cooling of the stimulus source in between stimulus cycles.

The wearable system of any embodiment disclosed herein, wherein the anomalous biologic event comprises a stroke event.

The wearable system of any embodiment disclosed herein, wherein the wearable system is positioned on a left limb of a user and a second wearable system is positioned on a right limb of the user, wherein the second wearable system comprises a second stimulus source and a second blood volume sensor, wherein the hardware processor is further configured to compare right side blood volume signals to left side blood volume signals to determine whether the anomalous biologic event has occurred.

The wearable system of any embodiment disclosed herein, wherein the hardware processor is further configured to:
  synchronize the signals received from the left limb and the right limb in time; and
  compare the synchronized signals from the left limb and the right limb to determine whether the anomalous biologic event occurred.

The wearable system of any embodiment disclosed herein, wherein the comparison takes into account a baseline difference between the left limb and the right limb.

The wearable system of any embodiment disclosed herein, further comprising a tensionable band coupled to the body.

The wearable system of any embodiment disclosed herein, wherein the tensionable band further comprises a visual indicator to indicate when one or more of: the stimulus source, the blood volume sensor, or a combination thereof is sufficiently coupled to the skin surface to enable accurate sensor readings.

The wearable system of any embodiment disclosed herein, wherein one or more ends of the tensionable band are coupled to the body at a position that is centered with respect to one or more sensors positioned on the second surface.

The wearable system of any embodiment disclosed herein, wherein the stimulus source is positioned concentrically about the blood volume sensor.

The wearable system of any embodiment disclosed herein, wherein the blood volume sensor comprises a photoplethysmography sensor or an impedance plethysmographic sensor.

The wearable system of any embodiment disclosed herein, further comprising a support structure coupled to the stimulus source and configured to couple the stimulus source to the second surface and at least partially expose the stimulus source to the cavity.

The wearable system of any embodiment disclosed herein, wherein the blood volume sensor is further configured to measure one or more of: heart rate, heart rate variability, or oxygen saturation.

The wearable system of any embodiment disclosed herein, wherein the stimulus cycle is individualized to the user.

The wearable system of any embodiment disclosed herein, wherein individualization of the stimulus cycle comprises receiving a user input related to perceived stimulus of the skin surface.

The wearable system of any embodiment disclosed herein, wherein individualization of the stimulus cycle is based on signals received from the blood volume sensor.

The wearable system of any embodiment disclosed herein, wherein the stimulus source comprises one of: a heating element or an environmental temperature.

The wearable system of any embodiment disclosed herein, wherein the hardware processor is configured to transmit an electronic message to a first electronic system responsive to the determination of the anomalous biologic event, said first electronic system configured to electronically manage a home automation system.

The wearable system of any embodiment disclosed herein, wherein the home automation system comprises a door lock and wherein said electronic message is configured to instruct the first electronic system to unlock the door lock.

The wearable system of any embodiment disclosed herein, wherein the home automation system comprises a home alarm system and wherein said electronic message is configured to instruct the first electronic system to disable the home alarm system.

The wearable system of any embodiment disclosed herein, wherein the home automation system comprises a display and wherein said electronic message is configured to instruct the first electronic system to display user's medical information.

The wearable system of any embodiment disclosed herein, wherein the medical information comprises medication information and/or medication regimen compliance.

The wearable system of any embodiment disclosed herein, wherein the home automation system comprises a display and wherein said electronic message is configured to instruct the first electronic system to display stroke treatment user interface.

The wearable system of any embodiment disclosed herein, wherein the home automation system comprises a speaker system and wherein said electronic message is configured to instruct the first electronic system to trigger an audible alarm with the speaker system.

The wearable system of any embodiment disclosed herein, wherein the hardware processor is further configured to alert a third party computing system responsive to the determination of the anomalous biologic event.

The wearable system of any embodiment disclosed herein, wherein the third party computing system comprises an emergency service system.

The wearable system of any embodiment disclosed herein, wherein the third party computing system comprises a clinician computing system.

The wearable system of any embodiment disclosed herein, wherein the hardware processor is further configured to initiate treatment protocol responsive to the detection of anomalous biologic event.

The wearable system of any embodiment disclosed herein, further comprising a wearable treatment system and said treatment protocol is configured to activate the wearable treatment system.

The wearable system of any embodiment disclosed herein, wherein the wearable treatment system comprises an ultrasonic helmet.

The wearable system of any embodiment disclosed herein, wherein the wearable treatment system comprises a cooling gas delivery system.

The wearable system of any embodiment disclosed herein, wherein the wearable treatment system comprises a cooling helmet.

A system for detecting an anomalous biologic event in a person, the system comprising one or more of the following:
- a first stimulus source configured to stimulate a first tissue site on a right side of the person's body at a first time;
- a second stimulus source configured to stimulate a second tissue site on a left side of the person's body at a second time; and
- one or more hardware processors configured to:
- determine a first vasodilation response based on the stimulation of the first tissue site;
- determine a second vasodilation response based on the stimulation of the second tissue site;
- determine one or more differences in the first vasodilation response and the second vasodilation response; and
- detect an anomalous biologic event based on the determined one or more differences in the first vasodilation response and the second vasodilation response.

The system of any embodiment disclosed herein, wherein the first stimulus source comprises at least one or more of the following: a heat source, a cooling source, or an electrical source.

The system of any embodiment disclosed herein, wherein the second stimulus source comprises at least one or more of the following: a heat source, a cooling source, or an electrical source.

The system of any embodiment disclosed herein, wherein the first time is synchronized with the second time.

The system of any embodiment disclosed herein, wherein the first vasodilation response is determined based on a parameter responsive to a measurement from a first blood volume sensor.

The system of any embodiment disclosed herein, wherein the second vasodilation response is determined based on a parameter responsive to a measurement from a second blood volume sensor.

The system of any embodiment disclosed herein, wherein the first vasodilation response is determined based on a parameter responsive to a measurement from an electrical activity sensor.

The system of any embodiment disclosed herein, wherein the second vasodilation response is determined based on a parameter responsive to a measurement from an electrical activity sensor.

The system of any embodiment disclosed herein, wherein the one or more hardware processors are further configured to determine a first baseline vasodilation response before the stimulation at the first tissue site and determine a second baseline vasodilation response before the stimulation at the second tissue site.

A wearable system for detecting a stroke event in a person, the wearable system comprising one or more of the following:
- a first wearable device configured to be in contact with a first skin surface of a person, said first wearable device configured to be secured to a left limb of the person, said first wearable device comprising:
- a first heat source in communication with the first skin surface, wherein the first heat source is configured to heat the first skin surface to a first target temperature;
- a first skin temperature sensor configured to measure a first temperature of the first skin surface; and
- a first blood volume sensor configured to measure a first blood volume at a first tissue site proximate to the first skin surface;
- a second wearable device configured to be in contact with a second skin surface of the person, said second wearable device configured to be secured to a right limb of the person, said second wearable device comprising:
- a second heat source in communication with the second skin surface, wherein the second heat source is configured to heat the second skin surface to a second target temperature;
- a second skin temperature sensor configured to measure a second temperature of the second skin surface; and
- a second blood volume sensor configured to measure a second blood volume at a second tissue site proximate to the second skin surface; and
- one or more hardware processors configured to:
- receive a first baseline blood volume signal from the first blood volume sensor;
- receive a second baseline blood volume signal from the second blood volume sensor;
- output a first heating signal to the first heat source to initiate a first heating cycle at a first time, wherein the first heating cycle comprises heating the first skin surface to the first target temperature;
- receive a first post stimulation blood volume signal from the first blood volume sensor in response to the first skin surface reaching the first target temperature;
- output a second heating signal to the second heat source to initiate a second heating cycle at a second time, wherein the second heating cycle comprises heating the second skin surface to the second target temperature;
- receive a second post stimulation blood volume signal from the second blood volume sensor in response to the second skin surface reaching the second target temperature; and determine a stroke event based on the first baseline blood volume signal, the second baseline blood volume signal, the first post stimulation blood volume signal, and the second post stimulation blood volume signal.

The wearable system of any embodiment disclosed herein, wherein the second post stimulation blood volume signal comprises a set of blood volume signals, such that the second blood volume of the second skin surface is measured repeatedly before, during, and after a heating cycle of the second heat source.

The wearable system of any embodiment disclosed herein, wherein the second post stimulation blood volume signal comprises a plurality of blood volume signals, such that the second blood volume of the second skin surface is measured continuously before, during, and after a heating cycle of the second heat source.

The wearable system of any embodiment disclosed herein, wherein the one or more hardware processors is further configured to calculate a first baseline ratio of alternating current (AC) to direct current (DC) for the first baseline blood volume signal and a second baseline ratio of AC to DC for the second blood volume signal and to compare the first baseline ratio to the second baseline ratio.

The wearable system of any embodiment disclosed herein, wherein the first wearable device further comprises an environmental temperature sensor.

The wearable system of any embodiment disclosed herein, further comprising a remote computing device communicative coupled to the first wearable device and the second wearable device.

The wearable system of any embodiment disclosed herein, wherein the remote computing device comprises one of: a laptop, cellular device, a workstation, a server, a desktop computer, a personal digital assistant, a second wearable system or device, or a netbook.

The wearable system of any embodiment disclosed herein, further comprising one or more electrodermal activity sensors.

The wearable system of any embodiment disclosed herein, wherein the one or more electrodermal activity sensors are spaced apart from at least one of the first heat source or the second heat source by about 0.25 inches to about 4 inches.

The wearable system of any embodiment disclosed herein, further comprising one or more motion sensors configured to measure a motion of a body portion to which at least one of the first wearable device or the second wearable device is coupled.

The wearable system of any embodiment disclosed herein, further comprising at least one tensionable band coupled to the body.

The wearable system of any embodiment disclosed herein, wherein the first heat source is positioned concentrically about one or both of the first blood volume sensor and the first skin temperature sensor.

The wearable system of any embodiment disclosed herein, wherein the second heat source is positioned concentrically about one or both of the second blood volume sensor and the second skin temperature sensor.

The wearable system of any embodiment disclosed herein, wherein the first blood volume sensor comprises a photoplethysmography sensor or an impedance plethysmographic sensor.

The wearable system of any embodiment disclosed herein, wherein the second blood volume sensor comprises a photoplethysmography sensor or an impedance plethysmographic sensor.

The wearable system of any embodiment disclosed herein, wherein the first skin temperature sensor comprises a thermocouple, a resistance temperature detector, a thermistor, or an infrared temperature sensor.

The wearable system of any embodiment disclosed herein, wherein the second skin temperature sensor comprises a thermocouple, a resistance temperature detector, a thermistor, or an infrared temperature sensor.

The wearable system of any embodiment disclosed herein, wherein the first blood volume sensor is further configured to measure one or more of: heart rate, heart rate variability, or oxygen saturation.

The wearable system of any embodiment disclosed herein, wherein the second blood volume sensor is further configured to measure one or more of: heart rate, heart rate variability, or oxygen saturation.

The wearable system of any embodiment disclosed herein, wherein at least one of the first target temperature or the second target temperature is individualized to the user.

What is claimed is:

1. A device configured to be secured to a person, said device responsive to one or more measurements on a skin surface of the person, the device comprising:
    a body comprising a first side configured to be in contact with the person, said first side including a first sub-portion configured to contact a first skin surface on a dorsal side of a wrist of the person, said first sub-portion comprising an outer perimeter;
    a strap configured to secure the body to the wrist of the person;
    a cutout in the first sub-portion, wherein said cutout comprises a shape including an inner perimeter and wherein said cutout is enclosed entirely within the outer perimeter;
    a thermal stimulus source in thermal communication with the first skin surface, wherein the thermal stimulus source comprises a surface area extending on a portion formed on the first sub-portion between the inner perimeter and the outer perimeter;
    an environmental temperature sensor configured to measure ambient temperature, said environmental temperature sensor positioned on a second side of the body opposite the first side including the thermal stimulus source;
    a skin temperature sensor configured to measure a temperature of the first skin surface, wherein the skin temperature sensor is positioned within the cutout;
    a hardware processor configured to couple with the environmental temperature sensor and the skin temperature sensor; and
    an interstitial gap within the body between the first side and the second side, wherein the interstitial gap is configured to separate the hardware processor and the environmental temperature sensor from the thermal stimulus source.

2. The device of claim 1, further comprising a remote computing device communicatively coupled to the device, the device transmitting data to the remote computing device.

3. The device of claim 2, wherein the remote computing device comprises one of: a laptop, a cellular device, a workstation, a server, a desktop computer, a personal digital assistant, a second system or device, or a netbook.

4. The device of claim 1, further comprising one or more hardware processors communicatively coupled to the device configured to detect a stroke event based on a temperature asymmetry determination responsive to measurements from the skin temperature sensor and a second skin temperature sensor.

5. The device of claim 1, further comprising an optical sensor configured to monitor a blood flow, wherein the optical sensor is positioned in an other cutout enclosed by the surface area.

6. The device of claim 5, wherein the thermal stimulus source is positioned concentrically about the optical sensor.

7. The device of claim 1, wherein the thermal stimulus source comprises a printed layer of resistive ink on polyimide film.

8. The device of claim 1, wherein the thermal stimulus source is positioned concentrically about the skin temperature sensor.

9. The device of claim 1, wherein the thermal stimulus source cycles between a target temperature and a deactivated or off state to maintain the target temperature.

10. The device of claim 1, further comprising a port, the port electrically coupling to a power source.

11. The device of claim 10, wherein the port electrically couples to an external or remote computing device.

12. The device of claim 1, further comprising a feedback mechanism for alerting the person after the detection of tremors or asymmetrical motion.

13. The device of claim 1, further comprising a blood volume sensor configured to measure a blood volume at the skin surface.

14. The device of claim 1, wherein the surface area extending on the portion formed on the first sub-portion between the inner perimeter and the outer perimeter and in contact with the first skin surface comprises a raised edge along a boundary of the surface area configured to be in contact with the first skin surface, wherein the cutout is enclosed within the raised edge.

15. The device of claim 1, further comprising an electrical based sensor positioned on a second sub-portion on the first side, said second sub-portion is separated from the first sub-portion and the thermal stimulus source, said electrical based sensor configured to contact a second skin surface of the person,
    wherein the second sub-portion is configured to be laterally spaced closer to the wrist than the first sub-portion when the strap with the body is secured to the person.

16. The device of claim 1, further comprising one or more hardware processors configured to determine a rate of change of temperature of the first skin surface in response to a heating stimulus and determine a stroke event based on the determination of the rate of change.

17. The device of claim 16, wherein the rate of change is compared to a second rate of change at an opposite wrist of the person and wherein the determination of the stroke event is further based on the comparison.

\* \* \* \* \*